(12) United States Patent
Aksimentiev et al.

(10) Patent No.: US 10,900,067 B2
(45) Date of Patent: Jan. 26, 2021

(54) NUCLEIC ACID NANOPARTICLES FOR ANALYTE DETECTION

(71) Applicants: The Board of Trustees of the University of Illinois, Urbana, IL (US); University of North Carolina-Charlotte, Charlotte, NC (US); Northeastern University, Boston, MA (US)

(72) Inventors: Aleksei Aksimentiev, Urbana, IL (US); Kirill A. Afonin, Charlotte, NC (US); Meni Wanunu, Boston, MA (US)

(73) Assignees: The Board of Trustees of the University of Illinois, Urbana, IL (US); University of North Carolina—Charlotte, Charlotte, NC (US); Northeastern University, Boston, MA (US)

( * ) Notice: Subject to any disclaimer, the term of this patent is extended or adjusted under 35 U.S.C. 154(b) by 15 days.

(21) Appl. No.: 16/110,545

(22) Filed: Aug. 23, 2018

(65) Prior Publication Data

US 2019/0062814 A1 Feb. 28, 2019

Related U.S. Application Data

(60) Provisional application No. 62/549,032, filed on Aug. 23, 2017.

(51) Int. Cl.
*C12Q 1/6869* (2018.01)
*C12Q 1/6809* (2018.01)
(Continued)

(52) U.S. Cl.
CPC ............ *C12Q 1/6809* (2013.01); *C12N 15/11* (2013.01); *C12N 15/113* (2013.01); *C12N 15/65* (2013.01);
(Continued)

(58) Field of Classification Search
CPC ........ C12Q 1/6809; C12N 15/11; B82Y 15/00
See application file for complete search history.

(56) References Cited

U.S. PATENT DOCUMENTS 7,052,854 B2    5/2006   Melker et al.
8,394,584 B2    3/2013   Timp et al.
(Continued)

FOREIGN PATENT DOCUMENTS

WO    WO 2013/016486 A1    1/2013
WO    WO 2015/171827    * 11/2015

OTHER PUBLICATIONS

Lo et al, Self-assembly of three-dimensional DNA nanostructures and potential biological applications, 2010, Current Opinion in Chemical Biology, 14:597-607 (Year: 2010).*
(Continued)

*Primary Examiner* — Narayan K Bhat
(74) *Attorney, Agent, or Firm* — Leydig, Voit & Mayer, Ltd.

(57) ABSTRACT

Provided is a highly multiplex approach to disease condition diagnostics that combines nanopore sensing and nucleic acid nanoparticle (NANP) design and synthesis to detect multiple biomarkers to diagnose diseases. The system works by taking a sample containing biomarkers that is mixed with a plurality of nucleic acid nanoparticle (NANP) populations, with each population designed and synthesized to be able to detect a particular biomarker. Upon incubation, the mixture is used with nanopore measurements, with recordings of the ionic current through the nanopore. The ionic current recordings are analyzed, which determines the presence and/or concentration of biomarkers in the sample.

28 Claims, 26 Drawing Sheets

Specification includes a Sequence Listing.

(51) Int. Cl.
| | |
|---|---|
| C12N 15/65 | (2006.01) |
| C12N 15/113 | (2010.01) |
| C12N 15/11 | (2006.01) |
| B82Y 5/00 | (2011.01) |
| B82Y 15/00 | (2011.01) |

(52) U.S. Cl.
CPC .............. *C12Q 1/6869* (2013.01); *B82Y 5/00* (2013.01); *B82Y 15/00* (2013.01); *C12N 2310/3181* (2013.01)

(56) References Cited

U.S. PATENT DOCUMENTS

| 8,748,091 | B2 | 6/2014 | Timp et al. |
|---|---|---|---|
| 2009/0018028 | A1* | 1/2009 | Lindsay .................. B82Y 5/00 506/9 |
| 2013/0240359 | A1 | 9/2013 | Turner et al. |
| 2016/0258939 | A1 | 9/2016 | Morin et al. |
| 2019/0127682 | A1 | 5/2019 | Aksimentiev et al. |

OTHER PUBLICATIONS

Ko et al, Synergistic self-assembly of RNA and DNA molecules, 2010, Nat. Chem, 2, 1050-1055 (Year: 2010).*
Ang et al, Rapid and Label-Free Single-Nucleotide Discrimination via an Integrative NanoparticleNanopore Approach, 2012, ACS Nanao, 6, 8815-8823 (Year: 2012).*
Alibakhshi et al (post art), Picomolar Fingerprinting of Nucleic Acid Nanoparticles Using Solid-State Nanopores, 2017, ACS Nano, 11,9701-9710, published Aug. 25, 2017. (Year: 2017).*
U.S. Appl. No. 16/179,214, filed Nov. 2, 2018.
Afonin et al. (2008) "Specific RNA Self-Assembly with Minimal Paranemic Motifs," J. Am. Chem. Soc. 130(1):93-102.
Afonin et al. (2010) "In Vitro Assembly of Cubic RNA-Based Scaffolds Designed in Silico," Nat. Nanotechnol. 5:676-682.
Afonin et al. (2011) "Design and Self-Assembly of siRNA-Functionalized RNA Nanoparticles for Use in Automated Nanomedicine," Nat. Protoc. 6:2022-2034.
Afonin et al. (2013) "Engineered RNA Nanodesigns for Applications in RNA Nanotechnology," DNA RNA Nanotechnol. 1(1):1-15.
Afonin et al. (2014) "Computational and Experimental Characterization of RNA Cubic Nanoscaffolds," Methods 67(2):256-265.
Afonin et al. (2014) "In Silico Design and Enzymatic Synthesis of Functional RNA Nanoparticles," Acc. Chem. Res. 47(6):1731-1741.
Afonin et al. (2014) "Multifunctional RNA Nanoparticles," Nano Lett. 14(10):5662-5671.
Aksimentiev et al. (2004) "Microscopic Kinetics of DNA Translocation through Synthetic Nanopores," Biophys. J. 87(3):2086-2097.
Alibakhshi et al. (publicly available Aug. 25, 2017) "Picomolar fingerprinting of nucleic acid nanoparticles using solid-state nanopores," ACS Nano (Oct. 2017) 11(10):9701-9710.
Andersen (1983) "Rattle: A 'Velocity' Version of the Shake Algorithm for Molecular Dynamics Calculations," J. Comput. Phys. 52(1):24-34.
Andersen et al. (2009) "Self-Assembly of a Nanoscale DNA Box with a Controllable Lid," Nature 459:73-76.
Bacri et al. (2011) "Discrimination of Neutral Oligosaccharides through a Nanopore," Biochem. Biophys. Res. Commun. 412(4):561-564.
Batcho et al. (2001) "Optimized Particle-Mesh Ewald/Multiple-Time Step Integration for Molecular Dynamics Simulations," J. Chem. Phys. 115(9):4003-4018.
Bayley (2015) "Nanopore Sequencing: From Imagination to Reality," Clin. Chem. 61(1):25-31.
Best et al. (2012) "Optimization of the Additive CHARMM All-Atom Protein Force Field Targeting Improved Sampling of the Backbone $\phi$, $\Psi$ and Side-Chain $X_1$ and $X_2$ Dihedral Angles," J. Chem. Theory Comput. 8(9):3257-3273.

Bhatia et al. (2009) "Icosahedral DNA Nanocapsules by Modular Assembly," Angew. Chem. Int. Ed. 48(23):4134-4137.
Bhatia et al. (Aug. 2016) "Quantum Dot-Loaded Monofunctionalized DNA Icosahedra for Single-Particle Tracking of Endocytic Pathways," Nat. Nanotechnol. 11:1112-1119.
Branton et al. (2008) "The Potential and Challenges of Nanopore Sequencing," Nat. Biotechnol. 26:1146-1153.
Bui et al. (Apr. 2017) "Versatile RNA Tetra-U Helix Linking Motif as a Toolkit for Nucleic Acid Nanotechnology," Nanomedicine: Nanotechnology, Biology and Medicine 13(3):1137-1146.
Bujold et al. (Oct. 2016) "Optimized DNA 'Nanosuitcases' for Encapsulation and Conditional Release of siRNA," J. Am. Chem. Soc. 138(42):14030-14038.
Cai et al. (2015) "Resistive-Pulse Measurements with Nanopipettes: Detection of Vascular Endothelial Growth Factor C (VEGF-C) Using Antibody-Decorated Nanoparticles," Anal. Chem. 87(12):6403-6410.
Carson et al. (2015) "Challenges in DNA Motion Control and Sequence Readout Using Nanopore Devices," Nanotechnology 26(7):074004, pp. 1-14.
Cassinelli et al. (2015) "One-Step Formation of 'Chain-Armor'-Stabilized DNA Nanostructures," Angew. Chem. Int. Ed. 54(27):7795-7798.
Chidchob et al. (Mar. 2016) "Synergy of Two Assembly Languages in DNA Nanostructures: Self-Assembly of Sequence-Defined Polymers on DNA Cages," J. Am. Chem. Soc. 138(13):4416-4425.
Comer et al. (2009) "Microscopic Mechanics of Hairpin DNA Translocation through Synthetic Nanopores," Biophys. J. 96(2):593-608.
Cruz-Chu et al. (2006) "Water—Silica Force Field for Simulating Nanodevices," J. Phys. Chem. B 110(43):21497-21508.
Dao et al. (2015) "Triggering RNAi with Multifunctional RNA Nanoparticles and Their Delivery," DNA RNA Nanotechnol. 2:1-12.
Darden et al. (1993) "Particle Mesh Ewald: An N•log(N) Method for Ewald Sums in Large Systems," J. Chem. Phys. 98(12):10089-10092.
Dekker (2007) "Solid-State Nanopores," Nat. Nanotechnol. 2:209-215.
Dibrov et al. (2011) "Self-Assembling RNA Square," Proc. Natl. Acad. Sci. U.S.A. 108(16):6405-6408.
Fennouri et al. (2012) "Single Molecule Detection of Glycosaminoglycan Hyaluronic Acid Oligosaccharides and Depolymerization Enzyme Activity Using a Protein Nanopore," ACS nano 6(11):9672-9678.
Firnkes et al. (2010) "Electrically Facilitated Translocations of Proteins through Silicon Nitride Nanopores: Conjoint and Competitive Action of Diffusion, Electrophoresis, and Electroosmosis," Nano Lett. 10(6):2162-2167.
Fologea et al. (2007) "Electrical Characterization of Protein Molecules by a Solid-State Nanopore," Appl. Phys. Lett. 91(5):053901, 3 pp.
Furey (2012) "ChIP-seq and beyond: new and improved methodologies to detect and characterize protein-DNA interactions," Nature Reviews Genetics 13:840-852.
Galas et al. (1978) "DNAase footprinting: a simple method for the detection of protein-DNA binding specificity," Nucleic Acids Research 5(9):3157-3170.
Garner et al. (1981) "A gel electrophoresis method for quantifying the binding of proteins to specific DNA regions: application to components of the *Escherichia coli* lactose operon regulatory system," Nucleic Acids Research 9(13):3047-3060.
Gershow et al. (2007) "Recapturing and Trapping Single Molecules with a Solid-State Nanopore," Nat. Nanotechnol. 2:775-779.
Goodman et al. (2005) "Rapid Chiral Assembly of Rigid DNA Building Blocks for Molecular Nanofabrication," Science 310(5754):1661-1665.
Grabow et al. (2011) "Self-Assembling RNA Nanorings Based on RNAI/II Inverse Kissing Complexes," Nano Lett. 11(2):878-887.
Grabow et al. (2014) "RNA Self-Assembly and RNA Nanotechnology," Acc. Chem. Res. 47(6):1871-1880.

(56) References Cited

OTHER PUBLICATIONS

Guo et al. (1998) "Inter-RNA Interaction of Phage Phi29 pRNA to Form a Hexameric Complex for Viral DNA Transportation," Mol. Cell 2(1):149-155.
Guo et al. (2005) "Specific Delivery of Therapeutic RNAs to Cancer Cells Via the Dimerization Mechanism of Phi29 Motor pRNA," Hum. Gene Ther. 16(9):1097-1109.
Guo et al. (2006) "Construction of Folate-Conjugated pRNA of Bacteriophage Phi29 DNA Packaging Motor for Delivery of Chimeric siRNA to Nasopharyngeal Carcinoma Cells," Gene Ther. 13:814-820.
Guo (2010) "The Emerging Field of RNA Nanotechnology," Nat Nanotechnol 5:833-842.
Guo et al. (2012) "Uniqueness, Advantages, Challenges, Solutions, and Perspectives in Therapeutics Applying RNA Nanotechnology," Nucleic Acid Ther. 22(4):226-245.
Halman et al. (publicly available Jan. 2017) "Functionally-Interdependent Shape-Switching Nanoparticles with Controllable Properties," Nucleic Acids Res. (Feb. 2017) 45(4):2210-2220.
Haque et al. (2013) "Solid-State and Biological Nanopore for Real-Time Sensing of Single Chemical and Sequencing of DNA," Nano today 8(1):56-74.
He et al. (2008) "Hierarchical Self-Assembly of DNA into Symmetric Supramolecular Polyhedra," Nature 452:198-201.
Heng et al. (2005) "Stretching DNA Using the Electric Field in a Synthetic Nanopore," Nano Lett. 5(10):1883-1888.
Holden et al. (2011) "Electrical Signature of the Deformation and Dehydration of Microgels During Translocation through Nanopores," Soft Matter 7(18):8035-8040.
Holden et al. (2011) "Resistive Pulse Analysis of Microgel Deformation During Nanopore Translocation," J. Phys. Chem. C 115(7):2999-3004.
Howorka et al. (2009) "Nanopore Analytics: Sensing of Single Molecules," Chem. Soc. Rev. 38(8):2360-2384.
Kasianowicz et al. (2008) "Nanoscopic Porous Sensors," Annu. Rev. Anal. Chem. 1:737-766.
Kim et al. (2006) "Rapid Fabrication of Uniformly Sized Nanopores and Nanopore Arrays for Parallel DNA Analysis," Adv. Mater. 18(23):3149-3153.
Kim et al. (2007) "Characteristics of Solid-State Nanometre Pores Fabricated Using a Transmission Electron Microscope," Nanotechnology 18(20):205302, pp. 1-5.
Kim et al. (Apr. 2016) "Generation of siRNA Nanosheets for Efficient RNA Interference," Sci. Rep. 6: 25146, pp. 1-7.
Kundu et al. (publicly available Apr. 2017) "Nucleic acid based polymer and nanoparticle conjugates: Synthesis, properties and applications," Progress in Materials Science (Jul. 2017) 88:136-185.
Larkin et al. (2014) "High-Bandwidth Protein Analysis Using Solid-State Nanopores," Biophys. J. 106(3):696-704.
Li et al. (2010) "The Distribution of DNA Translocation Times in Solid-State Nanopores," J. Phys.: Condens. Matter 22(45):454129, pp. 1-8.
Li et al. (Jun. 2016) "Controllable Self-Assembly of RNA Tetrahedrons with Precise Shape and Size for Cancer Targeting," Adv. Mater. 28(34):7501-7507.
Liu et al. (2015) "Self-Assembly of Responsive Multilayered DNA Nanocages," J. Am. Chem. Soc. 137(5):1730-1733.
Martyna et al. (1994) "Constant Pressure Molecular Dynamics Algorithms," J. Chem. Phys. 101(5):4177-4189.
Miyamoto et al. (1992) "SETTLE: An Analytical Version of the SHAKE and RATTLE Algorithm for Rigid Water Models," J. Comput. Chem. 13(8):952-962.
Ohno et al. (2011) "Synthetic RNA-Protein Complex Shaped Like an Equilateral Triangle," Nat. Nanotechnol. 6:116-120.
Osada et al. (2014) "Engineering RNA-Protein Complexes with Different Shapes for Imaging and Therapeutic Applications," ACS nano 8(8):8130-8140.
Pevarnik et al. (2013) "Particle Deformation and Concentration Polarization in Electroosmotic Transport of Hydrogels through Pores," ACS nano 7(4):3720-3728.
Phillips et al. (2005) "Scalable Molecular Dynamics with NAMD," J. Comput. Chem. 26(16):1781-1802.
Plesa et al. (2014) "Ionic Permeability and Mechanical Properties of DNA Origami Nanoplates on Solid-State Nanopores," ACS nano 8(1):35-43.
Reiner et al. (2012) "Disease Detection and Management Via Single Nanopore-Based Sensors," Chem. Rev. 112(12):6431-6451.
Renard et al. (2001) "Development of a sensitive multi-well colorimetric assay for active NFκB," Nucleic acids research 29(4):E21, 5 pp.
Roark et al. (Oct. 2016) "Fluorescence Blinking as an Output for Signal for Biosensing," ACS Sensors 1(11):1295-1300.
Rosenstein et al. (2012) "Integrated Nanopore Sensing Platform with Sub-Microsecond Temporal Resolution," Nat. Methods 9:487-492.
Saleh et al. (2003) "Direct Detection of Antibody—Antigen Binding Using an on-Chip Artificial Pore," Proc. Natl. Acad. Sci. U.S.A. 100(3):820-824.
Santangelo et al. (2006) "Nanostructured Probes for RNA Detection in Living Cells" Annals of Biomed. Eng. 34(1):39-50.
Shlyakhtenko et al. (2003) "Silatrane-Based Surface Chemistry for Immobilization of DNA, Protein-DNA Complexes and Other Biological Materials," Ultramicroscopy 97(1-4):279-287.
Squires et al. (2017) "Chapter Fourteen-Single-Molecule Characterization of DNA-Protein Interactions Using Nanopore Biosensors," Methods Enzymol. 582:353-385.
Stewart et al. (Sep. 2016) "Programmable RNA Microstructures for Coordinated Delivery of siRNAs," Nanoscale 8(40):17542-17550.
Talaga et al. (2009) "Single-Molecule Protein Unfolding in Solid State Nanopores," J. Am. Chem. Soc. 131(26):9287-9297.
Tyagi et al. (2012) "Molecular Beacons in Diagnostics" F1000 Medicine Reports 4:10, pp. 1-6.
Van Beest et al. (1990) "Force Fields for Silicas and Aluminophosphates Based on Ab Initio Calculations," Phys. Rev. Lett. 64(16):1955-1958.
Venkatesan et al. (2011) "Nanopore Sensors for Nucleic Acid Analysis," Nat. Nanotechnol. 6:615-624.
Waduge et al. (May 2017) "Nanopore-Based Measurements of Protein Size, Fluctuations, and Conformational Changes," ACS nano 11(6):5706-5716.
Wang et al. (2011) "Nanopore-Based Detection of Circulating MicroRNAs in Lung Cancer Patients," Nat. Nanotechnol. 6:668-674.
Wang et al. (2013) "Engineered Nanopore of Phi29 DNA-Packaging Motor for Real-Time Detection of Single Colon Cancer Specific Antibody in Serum," ACS nano 7(11):9814-9822.
Wang et al. (2013) "Resistive-Pulse Measurements with Nanopipettes: Detection of Au Nanoparticles and Nanoparticle-Bound Anti-Peanut IgY," Chem. Sci. 4(2):655-663.
Wanunu et al. (2008) "DNA Translocation Governed by Interactions with Solid-State Nanopores," Biophys. J. 95(10):4716-4725.
Wanunu et al. (2010) "Electrostatic Focusing of Unlabelled DNA into Nanoscale Pores Using a Salt Gradient," Nat. Nanotechnol. 5:160-165.
Wanunu et al. (2010) "Rapid Electronic Detection of Probe-Specific MicroRNAs Using Thin Nanopore Sensors," Nat. Nanotechnol. 5:807-814.
Wanunu et al. (2011) "Nanopore Analysis of Individual RNA/Antibiotic Complexes," Acs Nano 5(12):9345-9353.
Wanunu (2012) "Nanopores: A Journey Towards DNA Sequencing," Phys. Life Rev. 9(2):125-158.
Wu et al. (2014) "The Estimation of Field-Dependent Conductance Change of Nanopore by Field-Induced Charge in the Translocations of AuNPs-DNA Conjugates," J. Phys. Chem. C 118(46):26825-26835.
Yang et al. (2005) "Molecular Beacon Imaging of Tumor Marker Gene Expression in Pancreatic Cancer Cells" Cancer Biol Ther. 4(5):561-570.
Yingling et al. (2007) "Computational Design of an RNA Hexagonal Nanoring and an RNA Nanotube," Nano Lett. 7(8):2328-2334.
Yoo et al. (2012) "Competitive Binding of Cations to Duplex DNA Revealed through Molecular Dynamics Simulations," J. Phys. Chem. B 116(43):12946-12954.

(56) References Cited

OTHER PUBLICATIONS

Yu et al. (2015) "De Novo Design of an RNA Tile That Self-Assembles into a Homo-Octameric Nanoprism," Nat. Commun. 6:5724, pp. 1-6.

* cited by examiner

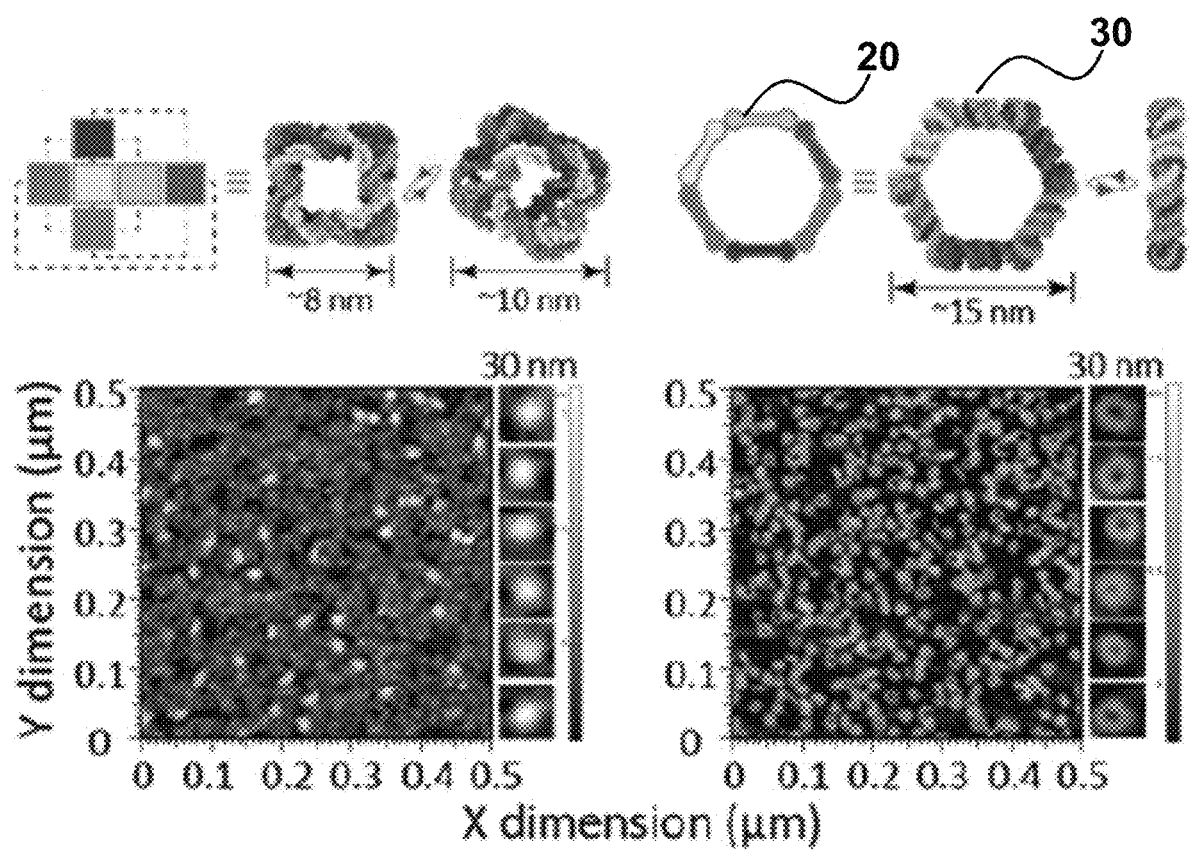
FIG. 1A
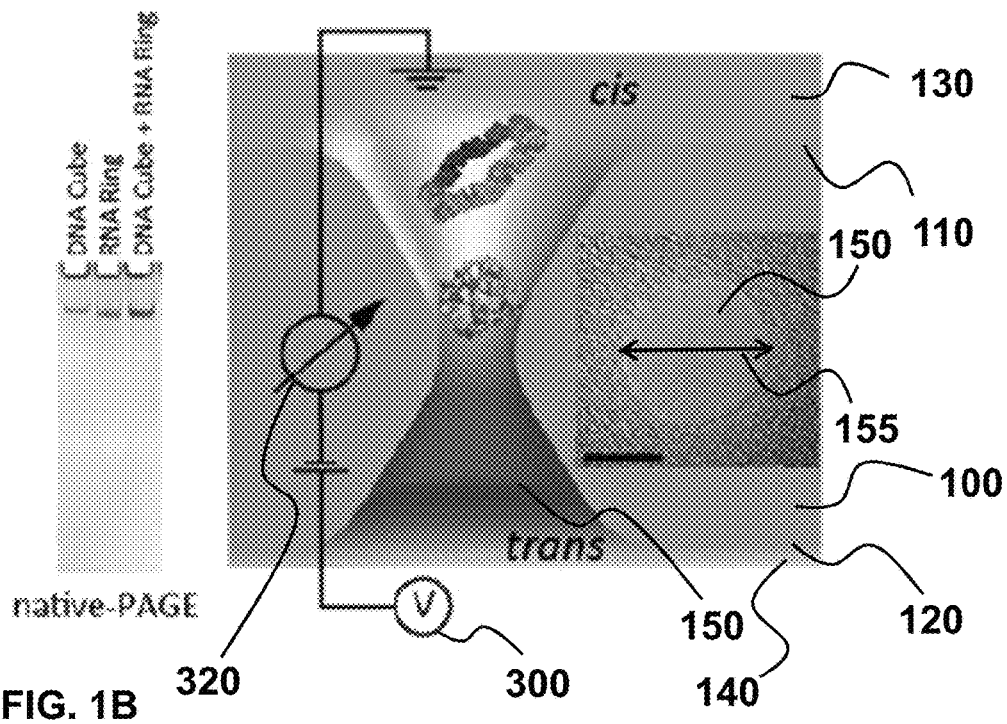
FIG. 1B
FIG. 1C

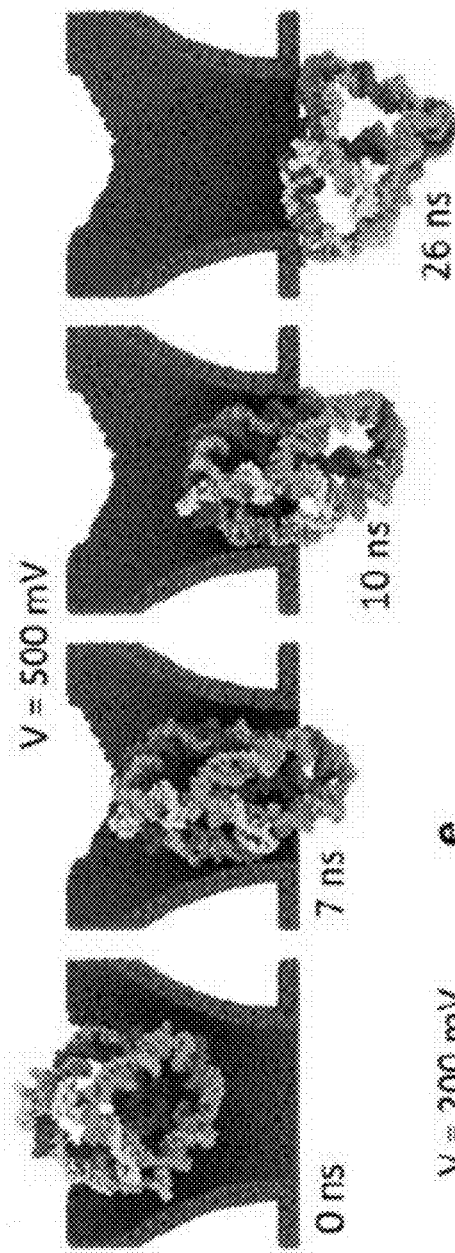
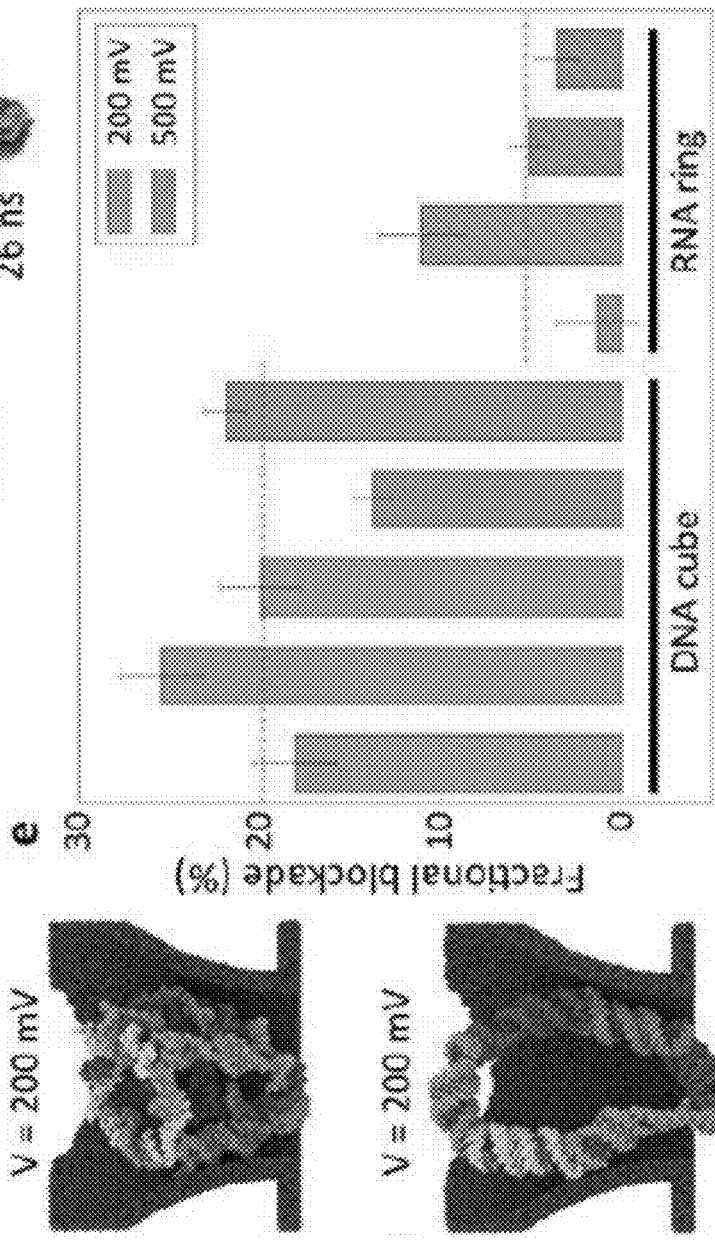
FIG. 5B
FIG. 5C
FIG. 5D
FIG. 5E

NUCLEIC ACID NANOPARTICLES FOR ANALYTE DETECTION

CROSS-REFERENCE TO RELATED APPLICATIONS

This application claims the benefit of priority to U.S. Provisional Patent Application No. 62/549,032, filed Aug. 23, 2017, which is hereby incorporated by reference in its entirety.

STATEMENT REGARDING FEDERALLY SPONSORED RESEARCH OR DEVELOPMENT

This invention was made with government support under GM114204, HG007406, and HG009186 awarded by National Institutes of Health, and DMR-1507985 awarded by the National Science Foundation. The government has certain rights in the invention.

REFERENCE TO A TABLE OF SEQUENCE LISTINGS

A sequence listing containing SEQ ID NOs:1-12 is submitted herewith and is specifically incorporated by reference. The table of sequence listings is specifically incorporated as part of the specification herein.

BACKGROUND

Timely detection of detrimental health conditions is paramount to efficient treatment. This is particularly true in the case of cancer, where early stage detection directly correlates with the long-term survival rate. It is not therefore surprising that early cancer diagnostics is the focus of considerable research efforts and investments from biomedical companies. The problem, however, is that various types of cancers present themselves differently at the molecular level and testing for all of them, known as liquid biopsy, is very elaborate and expensive. Although advances in DNA sequencing technology may soon permit affordable testing of patient's DNA, such tests alone are not sufficient to identify all type of cancers, in particular at early stages of development.

Detection of other molecular signatures, such as overexpression of specific proteins, antibodies, microRNAs, mRNAs and other biomarkers, has proven to be a more sensitive approach not only to cancer diagnostics but also to identification of general health conditions. However, detection of a particular biomarker requires a separate procedure, which in practice limits the number of tests that can be run at the same time and hence the number of decease conditions that can be probed.

The advent of nanopores as a single-molecule platform has advanced studies of a wide range of species such as proteins, drugs, nucleotides and polymers such as RNA, DNA, polypeptides, and polysaccharides.[1-7] Voltage-driven passage of analytes through a nanopore results in transient occlusion of the pore, which temporarily reduces the ionic current. The depth, duration and frequency of the current modulations contain information about size,[8-10] charge,[10-11] and structure[12-13] of biomolecules and their interactions with the nanopore.[3, 14] Deciphering such ionic current signals enables biophysical characterization of single molecule processes[15-16] and contributes to development of single molecule analytical methods[16-19] such as nanopore DNA sequencing.[2, 20-23] Alongside the development of nanopore-based sensing techniques, advances in nucleic acid nanotechnology have enabled design and programming of complex molecular structures for applications in nanomedicine and nano-biotechnology.

Nucleic acid nanoparticles (NANPs) are self-assembled nanostructures composed of multiple RNA or DNA molecules.[24] To date, a variety of distinct NANPs has been demonstrated differing from one another by their shape, size, internal connectivity, and physicochemical properties.[24-47] Ongoing development of NANPs is motivated by their potential applications in medicine and biotechnology, including their uses as carriers for RNAi inducers,[47-50] aptamers,[48, 51] fluorophores, and as customizable materials.[52-54] Striking features of these nanoparticles are their precisely defined molecular structures, chemical stability, and tunable physiochemical properties. Moreover, due to their size uniformity and biocompatibility, NANPs are expected to outperform their metal and polymeric nanoparticle counterparts previously used for biosensing through antibody-decoration, peptide coating, as well as DNA conjugation.[55-58]

The systems, kits and corresponding methods provided herein address the challenges associated with reliably and efficiently detecting markers of interest, including a plurality of biomarkers.

SUMMARY

Provided herein are specially configured NANPs that specifically bind a selected marker, such as an analyte or biomarker. Providing a plurality of NANP populations, wherein each population has a unique NANP electronic signature when transiting a nanopore under an applied electric field and unique biomarker target sequences, allows for electrical detection by NANP type and, therefore, corresponding biomarker. The NANPs are designed so that they are linkable, via analytes or biomarkers, such as in the form of a biomarker-linked linear chain of NANPs:

$NANP_1$-BiomarkerA-$NANP_2$-BiomarkerB-$NANP_3$-BiomarkerC-$NANP_4$ . . .

wherein NANPn refers to n unique populations of NANPs. In this manner, biomarkers can be identified by electrically monitoring an electrical parameter as the biomarker-linked linear chain of NANPs transits the nanopore. Unlinked individual NANPs provide a different electrical profile as they transit a nanopore and are readily distinguished from the corresponding linked NANPs in a linear chain of NANPs.

By providing a plurality of different biomarker target sequences on each NANP, the systems and methods provided herein are conducive for highly multiplexed detection of biomarkers, including a set of NANP populations that are capable of detecting a large number of disparate biomarkers. Alternatively, two biomarker target sequences on each NANP may be used to ensure more precise linear chain development as a plurality of different NANP's and a plurality of biomarkers are processed together.

As described herein, the invention includes NANP's, including a plurality of biomarker-linkable NANP populations, NANP kits, systems including such NANPs used with nanopore membranes and associated power and electrical monitoring across and/or through the nanopores, related methods of using such systems for detecting biomarkers, including for medical or health diagnostic applications.

Provided herein are a plurality of biomarker-linkable nucleic acid nanoparticle (NANP) populations for detecting one or more biomarkers in a sample. Each member of an NANP population may comprise a plurality of nucleic acid sequences that forms a core NANP structure; a biomarker target sequence extending from the core NANP structure, wherein the biomarker target sequence is configured to specifically bind to a biomarker; and a population-unique NANP electronic signature. In this manner, when a member of one NANP population is forced through a nanopore under an applied electric field, the specific NANP population (e.g., NANP type) can be identified by a measured electrical parameter, such as ionic current blockade, impendence or resistance, and time courses thereof. During use of the NANPs in the presence of a biomarker the biomarker binds to a first population of biomarkers at a first biomarker binding site and to a second population of biomarkers at a second biomarker binding site to form a linear chain of NANPs with an NANP sequence dependent on the biomarkers in the sample. The sequence can be determined by measuring a time course of an electrical parameter, wherein the value of the electrical parameter is determined by NANP type.

Each NANP may comprise a plurality of biomarker target sequences, such as two, three four, or more than four biomarker target sequences. The biomarker target sequences may be uniformly distributed over a NANP core structure, including at any corners for core structures having distinct edge surfaces (tetrahedron, cubes, hexagons, etc.), or uniformly spaced for NANP core structures having a continuous surface (e.g., spheres, rings) or at ends (e.g., cylinders). The target sequences may also number two and be arranged at opposing ends of the NANP, thereby ensuring a linear extension of linked NANPs.

The plurality of biomarker target sequences may each be unique to target a plurality of unique biomarkers. That is there is a one-to-one correspondence between a biomarker and a biomarker target sequence. Preferably, there are at least two different biomarker target sequences (BTS) on each NANP, so as to provide the capability of building longer-chain NANP sequences. The invention is, however, compatible with as few as one pair of NANP's linked by one biomarker, such as:

[$NANP_1$-$BTS_1$]-[Biomarker]-[$BTS_2$-$NANP_2$].

In that example, BTS1 can bind a physically distinct portion of the Biomarker sequence compared to the binding location of BTS2. Including additional different BTS with the NANP then allows for measure of additional biomarkers:

[$NANP_1$-$BTS_1$]-[Biomarker]-[$BTS_2$-$NANP_2$-$BTS_2$]-[Biomarker1]-[$BTS_3$-$NANP_3$-$BTS_4$]

The above illustrates use of three different NANP populations to detect two different biomarkers. In this example, it may be that the biomarker to-be-bound to BTS4 is not present, thereby cutting off that chain. Of course, a kit, systems or method having a higher number of NANP populations provides flexibility as to the sequence of the linear chain NANP. The specifics of a particular biomarker target sequence (BTS) depends on the biomarker of interest. Typically, the BTS will have a certain percentage and length of sequence identity to the biomarker binding sequence and, in turn, depends on the number and type of biomarker, including specified binding regions on the biomarker. Biomarkers having a high sequence similarity to other biomarkers may dictate that the BTS have high sequence complementarity, including to bind under stringent binding conditions. In contrast, if there are fewer biomarkers and/or greater dissimilarity, the sequence complementarity between the BTS and the biomarker binding region may be less, with corresponding less stringent binding conditions.

The core NANP structure may have one or more of a controllable shape, density, and/or effective size, so as to provide the unique NANP electronic signature. For example, larger size NANP may have a longer transit time in the nanopore compared to smaller sizes NANP. Similarly, denser less flexible NANP may have longer transit times. Charge density, total charge, or other charge variations between NANP may be detected by a difference in electrical parameter magnitude, including an ionic current blockade.

Each core NANP structure may have a preselected shape, size, charge and/or composition configured to provide an ionic current blockade contrast of at least 1%, 5%, or 10% compared to a next closest NANP during transit through a solid-state nanopore under an applied electric field. The devices and methods can accommodate various contrasts, with an important parameter that is the difference in measured current blockade for different NANP types is distinguishable given the baseline current and the sampling of the measurement. As desired, this contrast can be manipulated by varying the shape, size, charge and/or composition of an NANP population relative to other NANP populations, so as to achieve a desired contrast that may be matched to the nanopore membrane and attendant electrical parameter detector resolution.

Each population of NANPs is uniform, with a standard deviation of size and charge that is less than 10% of the average size and of the average charge to provide a substantially uniform ionic current blockade during transit through a solid-state nanopore under an applied electric field. Uniformity of an ionic current blockade for a given NANP population may be bolstered by use of a parachute or guiding particle connected to the NANP core. As discussed herein, the parachute or guiding particle may have the same charge as the NANP core structure to ensure appropriate extension and corresponding NANP alignment relative to a nanopore.

Any of the NANPs provided herein may have at least one NANP population that comprises at least one chemically-modified nucleotide; e.g., 2'-OMe. 2'-F, LNA, etc.

Any of the NANPs provided herein may have at least one NANP population comprises a mixture of RNA and DNA.

Any of the NANPs provided herein may have at least one NANP population comprises synthetic DNA.

Any of the NANPs provided herein may have at least one NANP population comprises RNA that is co-transcriptionally assembled, such as DNA and/or RNA made in a patient's cells, including for analysis of one or more cytoplasmic biomarkers.

The NANPs may have an effective diameter that is matched to a nanopore diameter so that the NANP deforms under an applied electric field to transit the solid-state nanopore. For example, the NANP may have a maximum effective diameter that is between 1 to 1.2 times the minimum nanopore diameter. In this manner, there must be some deformation of the NANP to transit the nanopore, thereby increasing dwell time and measured electrical parameter accuracy.

The NANPs may be further described in terms of one or more biomarker target sequences (BTS's), such as a length selected from the range of 4 to 100 or 10 nucleotides to 50 nucleotides; a complementary sequence of at least 80%, at least 90%, at least 95% or at least 98% to a target sequence; selected to specifically bind to a biomarker and/or a plurality of biomarker sequences spatially distributed over the NANP surface for multiplexed combinatorial analysis of a plurality of biomarkers.

Any of the NANPs provided herein may be provided as a kit for detection of a health condition. The kit may include instructions for processing a sample with the NANPs of the kit, including incubation times, temperatures, sample processing, electrical parameter detection and the like. The kit may include "read-out" instructions, where a detected electrical parameter and patterns thereof are associated with specific biomarkers. The presence/absence of biomarkers is then used to prove an assessment of a health condition, such as presence of a disease state, infection, contamination or genetic abnormality.

The NANPs provided herein may be used in a system for detection of biomarkers from a biological system. In addition to the NANPs, the system may further comprise a membrane comprising: a first surface and a second surface opposite said first surface, wherein said membrane separates a first fluid compartment comprising said first surface from a second fluid compartment comprising said second surface. A nanopore is positioned through said membrane and fluidically connects said first fluid compartment and said second fluid compartment. A power supply is in electrical contact with said membrane to provide an electric potential difference between said first fluid compartment and said second fluid compartment. A detector is configured to detect a time-varying electrical current through said nanopore as a linear chain of NANPs with a biomarker that links adjacent NANPs in the linear chain of NANPs transits said nanopore under an applied electric potential difference.

Depending on the application of interest, the nanopore may have a diameter that matches the nanopore effective diameter. For applications where it desired for transit velocity to be decreased, the nanopore may have a slightly smaller diameter than the nanopore, such as up to 10% smaller than the NANP effective diameter so that the NANP must deform at least slightly to transit the nanopore. Alternatively, if transit velocity is not a concern, the nanopore may have a slightly larger diameter than the nanopore, such as up to 10% larger than the NANP effective diameter. The nanopore may be described in term of an absolute value, such as an average nanopore diameter of between 5 nm and 100 nm. Any of the nanopores described herein may have a tapered shape, so that the nanopore diameter is described as the minimum diameter, including at a point of constriction located in the middle of the membrane through which the nanopore transits. In an embodiment, the nanopore may have an average nanopore diameter selected from the range of 5 nm to 100 nm.

Also provided herein is a method of detecting a plurality of biomarkers in a sample, the method comprising the steps of: mixing a sample with a plurality of unique NANPs and incubating the sample-NANPs mixture for an incubation time to form a chain of biomarker-linked NANPs. The linear chain of biomarker-linked NANPs is introduced to a first chamber formed by a first side of a nanopore-containing membrane, wherein the nanopore-fluidically connects the first chamber to a second chamber formed by a second side of the nanopore-containing membrane. Electrically energizing the nanopore-containing membrane drives the chain of biomarker-linked NANPs through the nanopore from the first chamber to the second chamber. An electrical parameter, such as an ionic current blockade is measured as a function of time as the chain of biomarker-linked NANPs transit the nanopore. The electrical parameter signature (e.g., time course), such as an ionic current blockade signature, identifies the NANP sequence of the chain of biomarker-linked NANPs, thereby detecting the plurality of biomarkers in the sample.

The step of measuring the ionic current blockade may comprise measuring the magnitude and/or duration of the current blockade.

The NANPs may be made by the steps of: providing a fixed number of DNA and/or RNA strands; and assembling the DNA and/or RNA strands in a prescribed shape so that each unique nanoparticle produces an ionic current blockade when passed through a nanopore that is different from every other unique NANP.

Each NANP may have a plurality of unique biomarker target sequences for targeting a plurality of different biomarkers so that a single set of NANP populations can detect a variety of health conditions. Optionally, each NANP has two biomarker target sequences, such as arranged in a generally opposed spatial configuration to ensure biomarker access remains when one of the biomarker target sequences is bound to the biomarker.

Any of the biomarkers described herein may comprise one or more of: a cancer marker; an autoimmune marker; a cardiac marker; an infectious marker; a genetic marker and biomarkers indicative of other diseases and infections.

Any of the methods, NANP's and systems described herein may use between two and ten NANP populations to detect between one and fifty unique biomarkers.

The NANP may be formed from any one or more nucleotide sequences, such as from any one or more of SEQ ID NOs: 1-12.

Also provided herein are analyte-linkable nucleic acid nanoparticle (NANP) comprising: a plurality of nucleic acid sequences that forms a core NANP structure having an NANP electronic signature during transit through a nanopore; an analyte target sequence configured to specifically bind to an analyte; a guidance particle connected to the core NANP structure to provide a reproducible orientation as the NANP approaches a nanopore under an applied electric field. In this context, reproducible orientation refers to an alignment of the NANP relative to a nanopore under a driving electric field such that the alignment and confirmation is maintained for the NANP population, as reflected by a highly specific and uniform electrical parameter, such as ionic current blockade, for NANPs that approach and enter the nanopore.

The guidance particle may be connected to the core NANP structure by a linker.

The analyte target sequence may be configured to specifically binds to a nucleic acid binding protein, including a transcription factor. The analyte target sequence may be configured to specifically binds to proteins, small molecules, metabolites, nucleic acids, etc.

The guidance particle may comprise a biomolecule, including a streptavidin protein, connected to the core NANP structure through a peptide nucleic acid linker. The guidance particle may comprise a bead or other synthetic material that exerts, for example, a hydrodynamic drag on the NANP as it migrates through a fluid under an applied electric field toward a nanopore. The guidance particle may be linked to the NANP, such as by a linker and/or or to an analyte bound to the analyte target sequence. In this manner, effect of guidance particle on the electrical parameter or signature as the NANP enters the nanopore is minimized.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

The features, objects and advantages other than those set forth above will become more readily apparent when consideration is given to the detailed description below. Such detailed description makes reference to the following drawings, wherein:

FIGS. 1A-1C. Assembly and visualization of nucleic acid nanoparticles (NANPs). Cartoon and 3D models (each strand colored differently) that define the structure of DNA cubes (FIG. 1A, top left panel) and RNA rings (FIG. 1A, top right panel). AFM images of the assembled structures are shown below each structure. FIG. 1B is an ethidium bromide total staining native-PAGE of rings, cubes, and mixture of rings and cubes. FIG. 1C is a schematic of a nanopore drawn approximately to scale with the two NANPs geometries illustrated in FIG. 1A. Inset: transmission electron micrograph of a 9 nm pore fabricated using electron beam irradiation of a 50-nm-thick silicon nitride membrane (scale bar: 5 nm).

FIG. 5B Snapshots illustrating a simulated translocation of a DNA cube under a 500 mV transmembrane bias. Water and ions are not shown for clarity. FIGS. 5C-5D Representative conformations of a DNA cube (FIG. 5C) and an RNA ring (FIG. 5D) trapped at the nanopore constriction under a 200 mV transmembrane bias. FIG. 5E. Percentage of the open-pore current reduced by the nanoparticles trapped in the nanopore. Several independent simulations were performed for each particle at each bias condition differing by the initial orientation of the particles with respect to the nanopore (see FIG. 11). The blockade currents were determined after the particles reached a stable conformation within the nanopore (see FIG. 12 and Table 1). The error bars represent the propagated standard error of 800-ps block averaging. A horizontal dashed line denotes the average blockade currents produced by DNA cubes and RNA rings.

Figure 13:
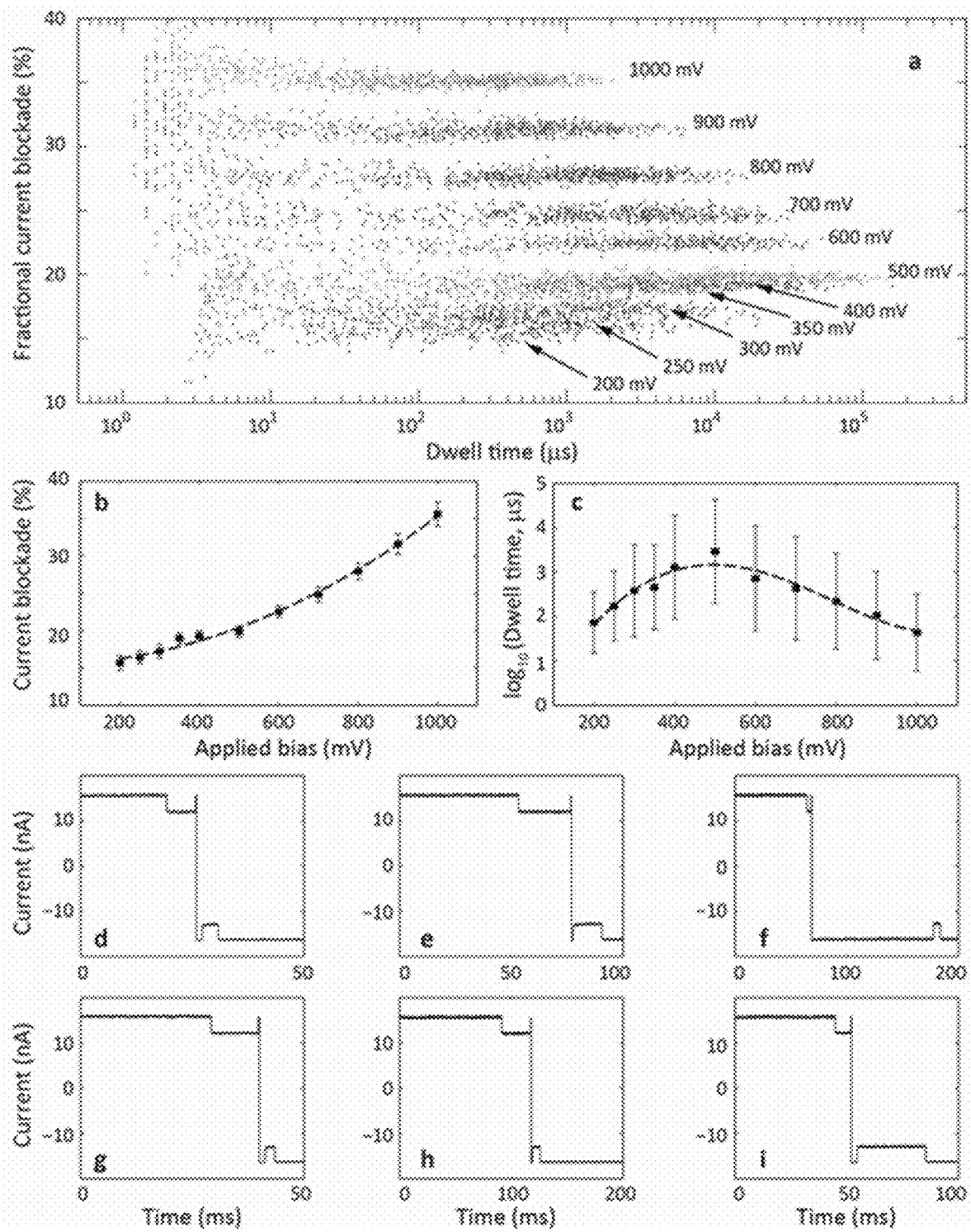

FIG. 13. Top panel is a scatter plot of fractional current blockade and dwell time for translocation of the DNA cubes at different voltages (labeled as "a"). The panels below are plots of fractional current blockade versus applied voltage (labeled as "b") and dwell time versus applied voltage (labeled as "c"). The remaining panels are recapture of DNA cubes after translocation at 800 mV. Experiments performed with 400 mM KCl (10 mM Tris, 2 mM MgCl$_2$, pH 7.9).

Figure 14:
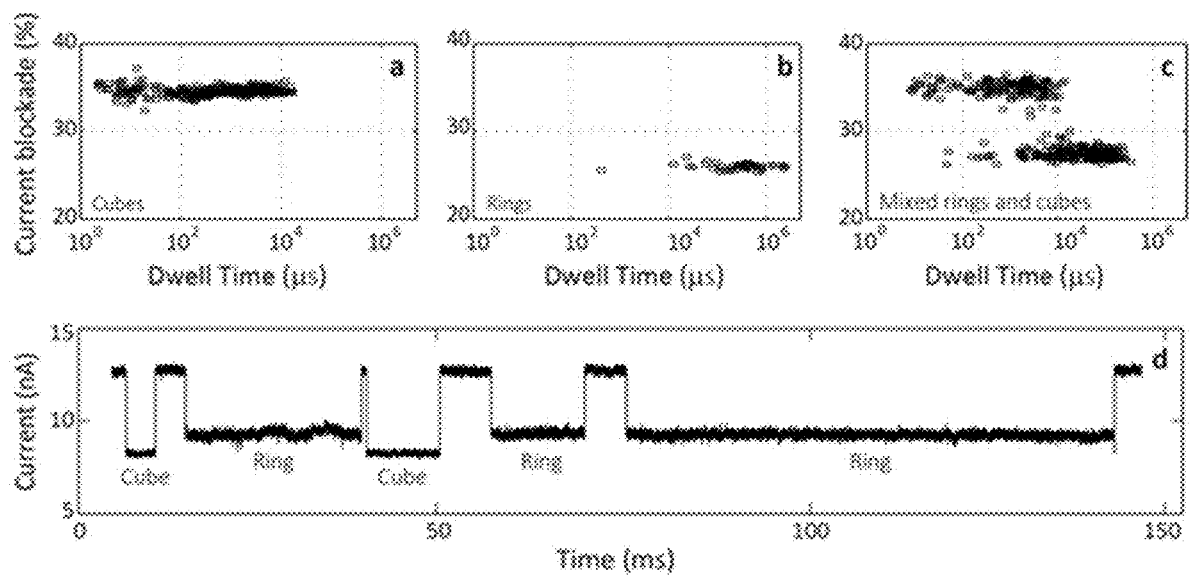

FIG. 14. Scatter plot of fractional current blockade and dwell time for translocation of (a) DNA cubes, (b) RNA rings, and (c) mixture of DNA cubes and RNA rings in a 9 nm-diameter nanopore at 1V. (d) Example of a current trace fragment recorded from a cube-ring mixture, the same system as in panel c. Experiments performed with 400 mM KCl (10 mM Tris, 2 mM MgCl$_2$, pH 7.9).

Figure 15:
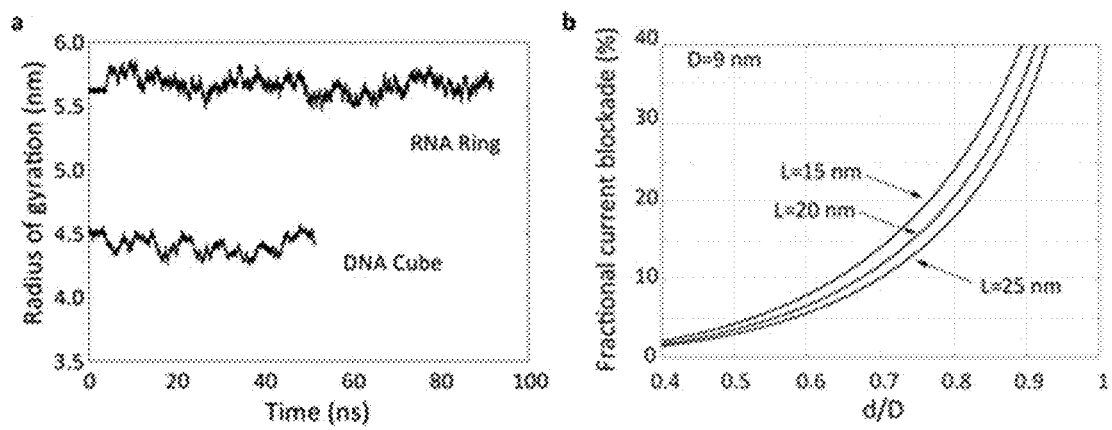

FIG. 15. (a) Fractional blockade of a D=9 nm cylindrical pore with different lengths. (b) Radius of gyration of the DNA cubes and the RNA rings obtained from MD simulations.

Figure 16:
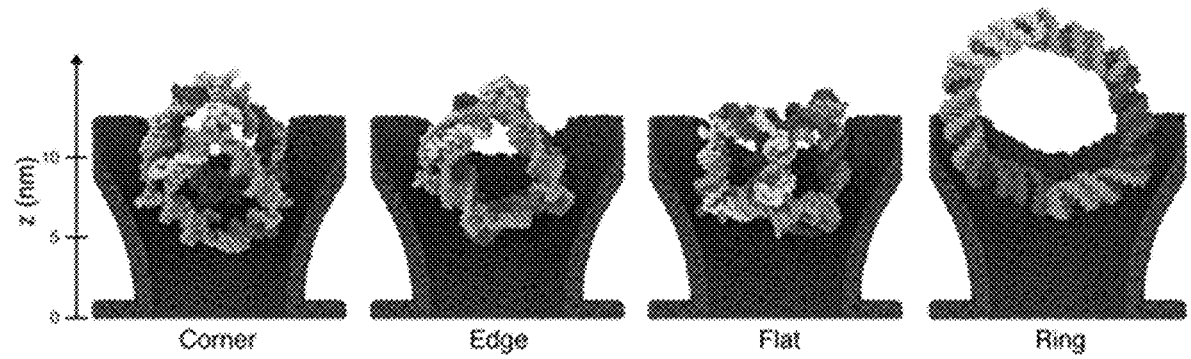

FIG. 16. Initial orientation of the NANPs in MD simulations of nanopore transport. The nanopore surface is shown in gray, separate strands of the NA nanoparticles are shown in different colors.

Figure 17:
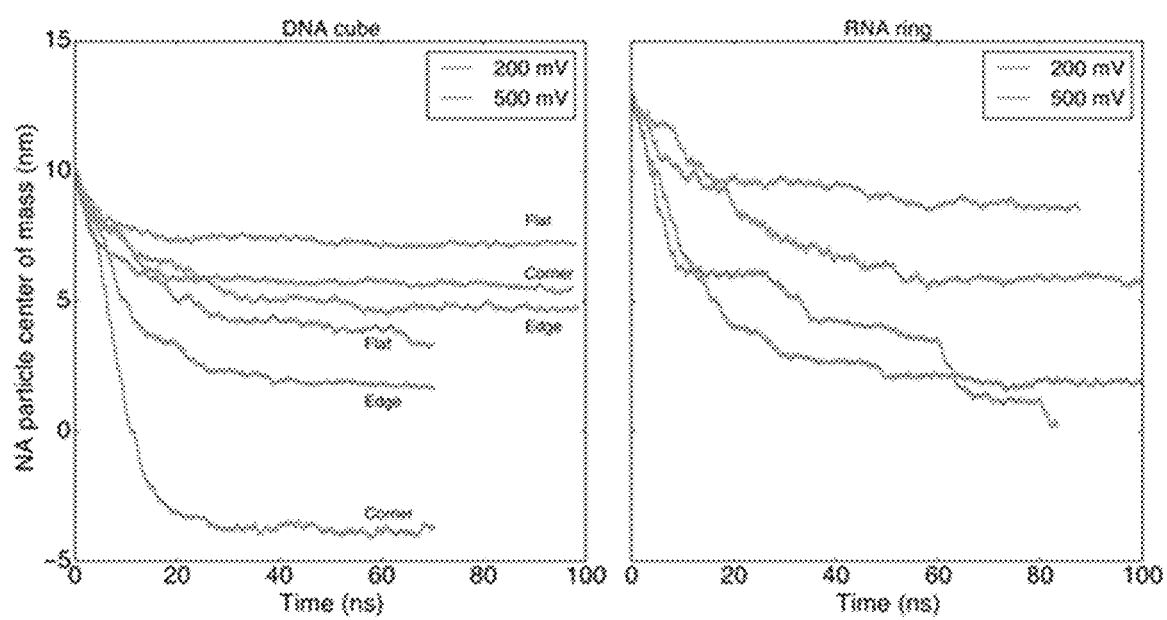

FIG. 17. Simulated displacement of NANPs through a solid-state nanopore. Z-coordinate of the particle's center of mass is plotted versus simulation time. The z-coordinate is aligned with the pore axis and attains zero at the trans end of the nanopore. Data shown in the left and right panels correspond to the simulations of the DNA cubes and RNA rings, respectively. In both panels, orange and blue lines indicate the outcomes of the simulations performed under 200 and 500 mV bias, respectively.

Figure 18:
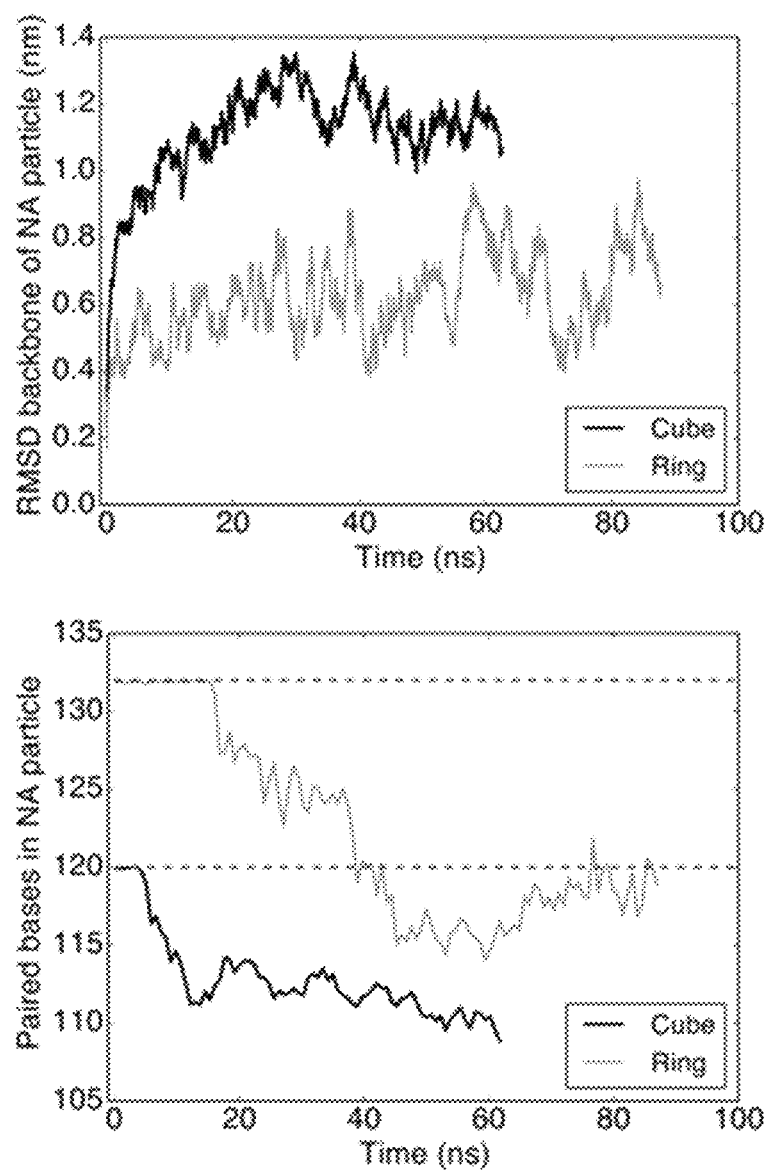

FIG. 18. Structural fluctuations of NANPs in bulk solution. (Top) RMSD of the NANPs from their idealized initial conformation during the few equilibration simulations. The RMSD was computed using coordinates of the NA backbone atoms. (Bottom) Number of bases paired in the NANPs during the free equilibration simulations. Horizontal dashed lines indicate the number of basepairs measured for the idealized geometry of the particles.

Figure 19:
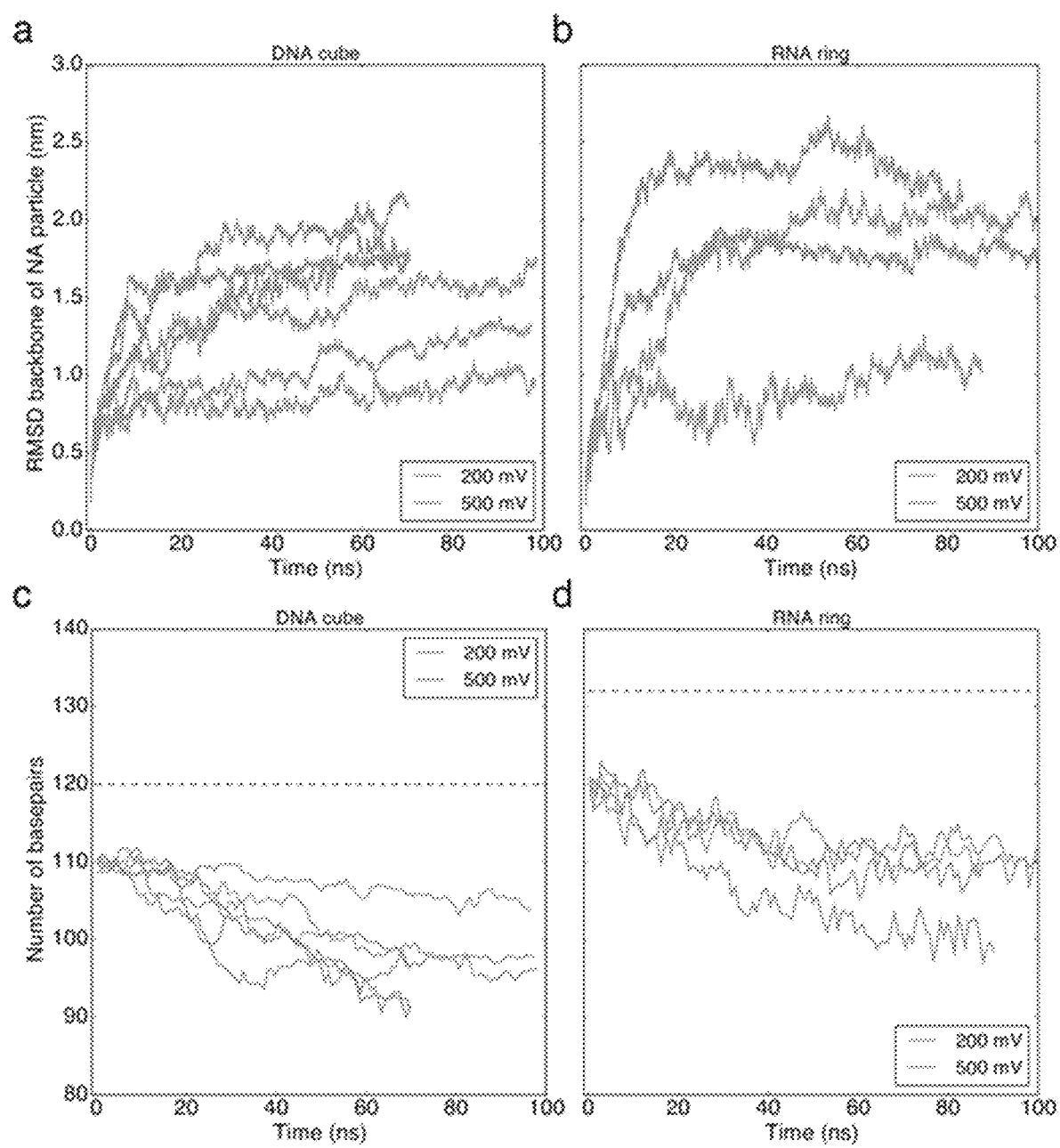

FIG. 19. Structural integrity of NANPs during simulated nanopore translocation. (top panels labeled as a,b) RMSD of the NANPs from their idealized initial conformations during the nanopore transport simulations. The RMSD was computed using coordinates of the NA backbone atoms. Data in the panels derived from the simulations of the DNA cubes and RNA rings, respectively. In both panels, orange and blue lines indicate the outcomes of the simulations performed under 200 and 500 mV bias, respectively. Bottom panels (labeled as c,d) Number of intact basepairs in NANPs during the nanopore transport simulations. Horizontal dashed lines indicate the number of basepairs measured for the idealized geometry of the particles.

Figure 20:
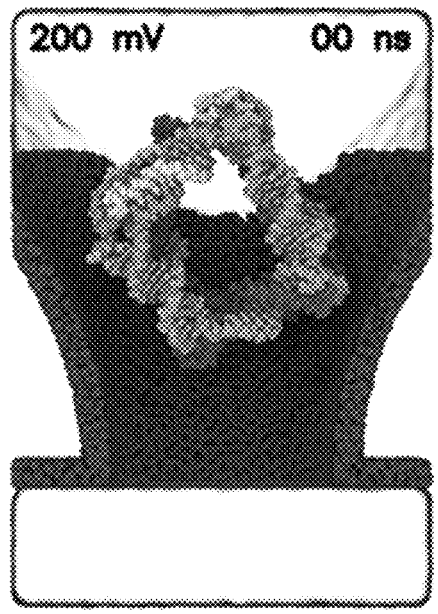

FIG. 20. Animation illustrating a 99 ns MD trajectory of a DNA cube translocation through a solid-state nanopore. The simulation begins with the edge of the DNA cube pointing toward the nanopore constriction. The simulation was performed under a 200 mV bias.

Figure 21:
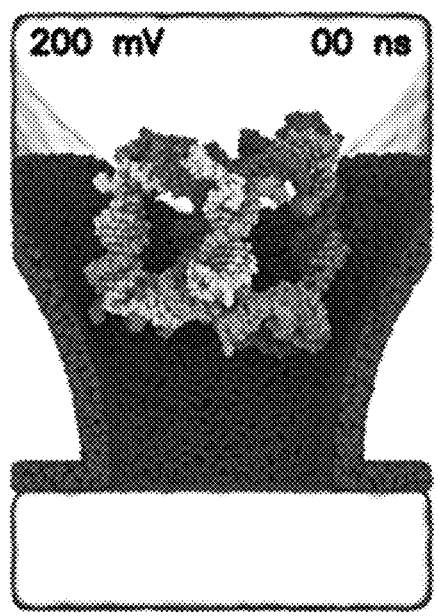

FIG. 21. Animation illustrating a 98 ns MD trajectory of a DNA cube translocation through a solid-state nanopore. The simulation began with a face of the DNA cube pointing toward the nanopore constriction. The simulation was performed under a 200 mV bias.

Figure 22:
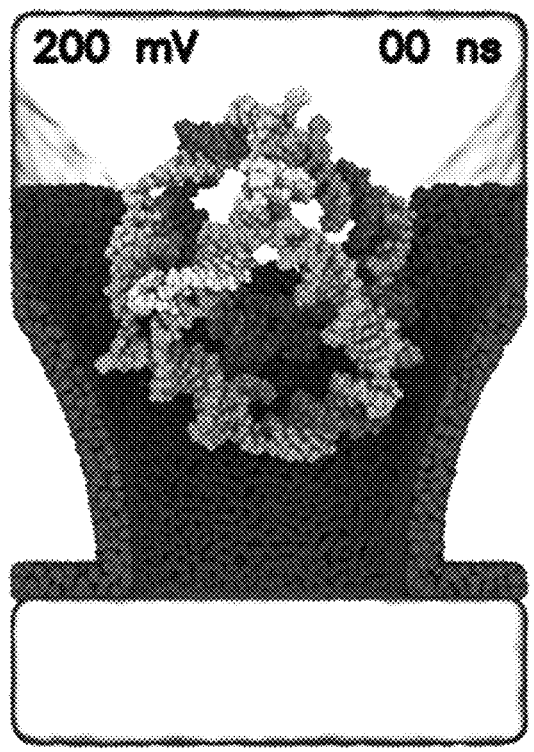

FIG. 22. Animation illustrating a 97 ns MD trajectory of a DNA cube translocation through a solid-state nanopore. The simulation began having a corner of the DNA cube pointing toward the nanopore constriction. The simulation was performed under a 200 mV bias.

Figure 23:
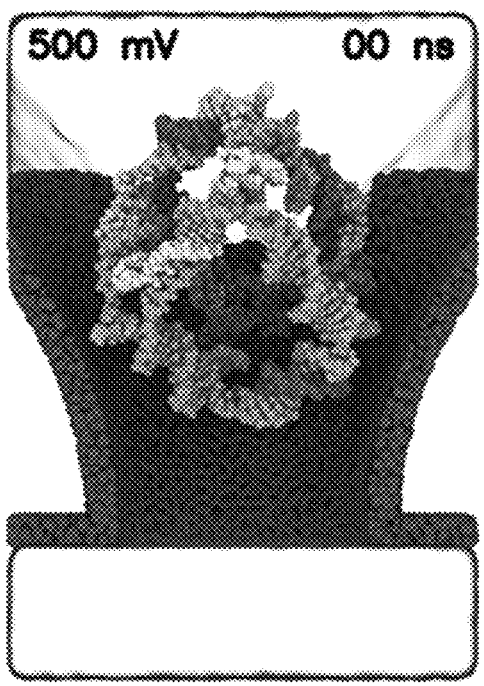

FIG. 23. Animation illustrating a 70 ns MD trajectory of a DNA cube translocation through a solid-state nanopore. The simulation began having a corner of the DNA cube pointing toward the nanopore constriction. The simulation was performed under a 500 mV bias.

Figure 24:
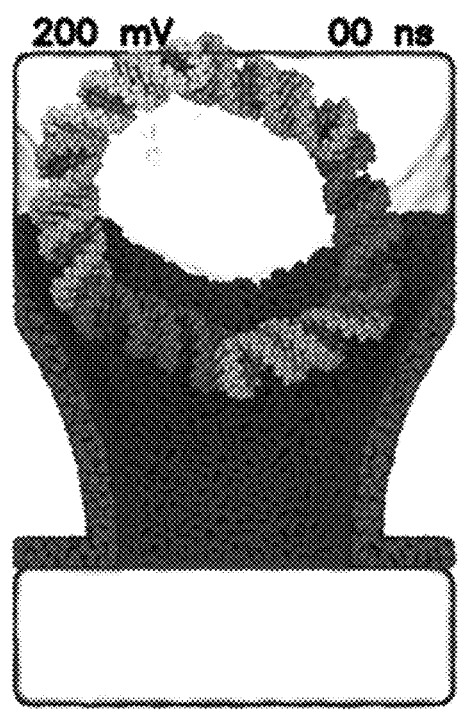

FIG. 24. Animation illustrating a 115 ns MD trajectory of an RNA ring translocation through a solid-state nanopore. The simulation began having the ring centered in the nanopore, and the axis of the nanopore in the plane of the ring. The simulation was performed under a 200 mV bias.

Figure 25:
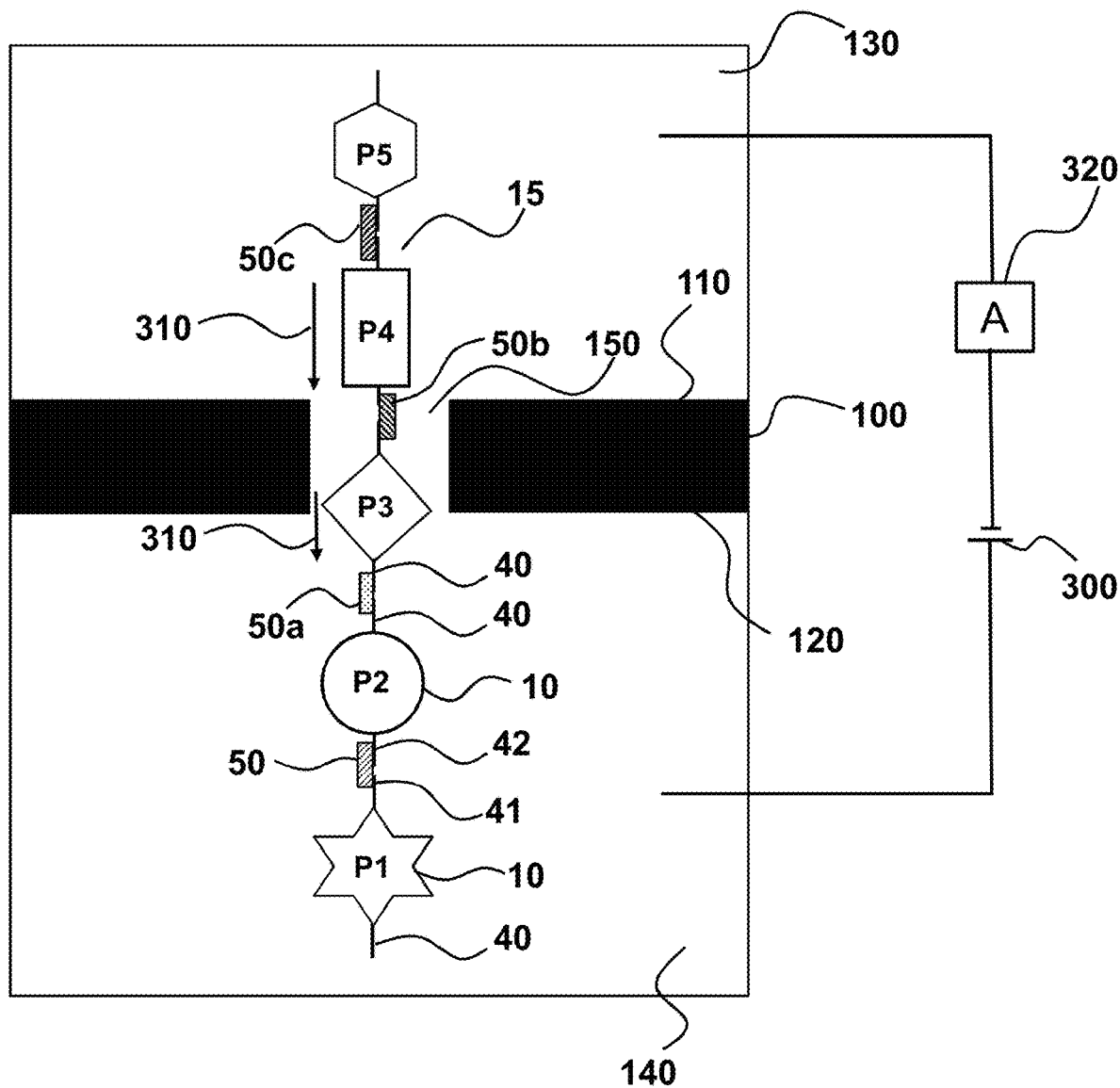

FIG. 25 is a schematic illustration of a system for multiplex detection of biomarkers, including biomarkers from a biological sample.

Figure 26:
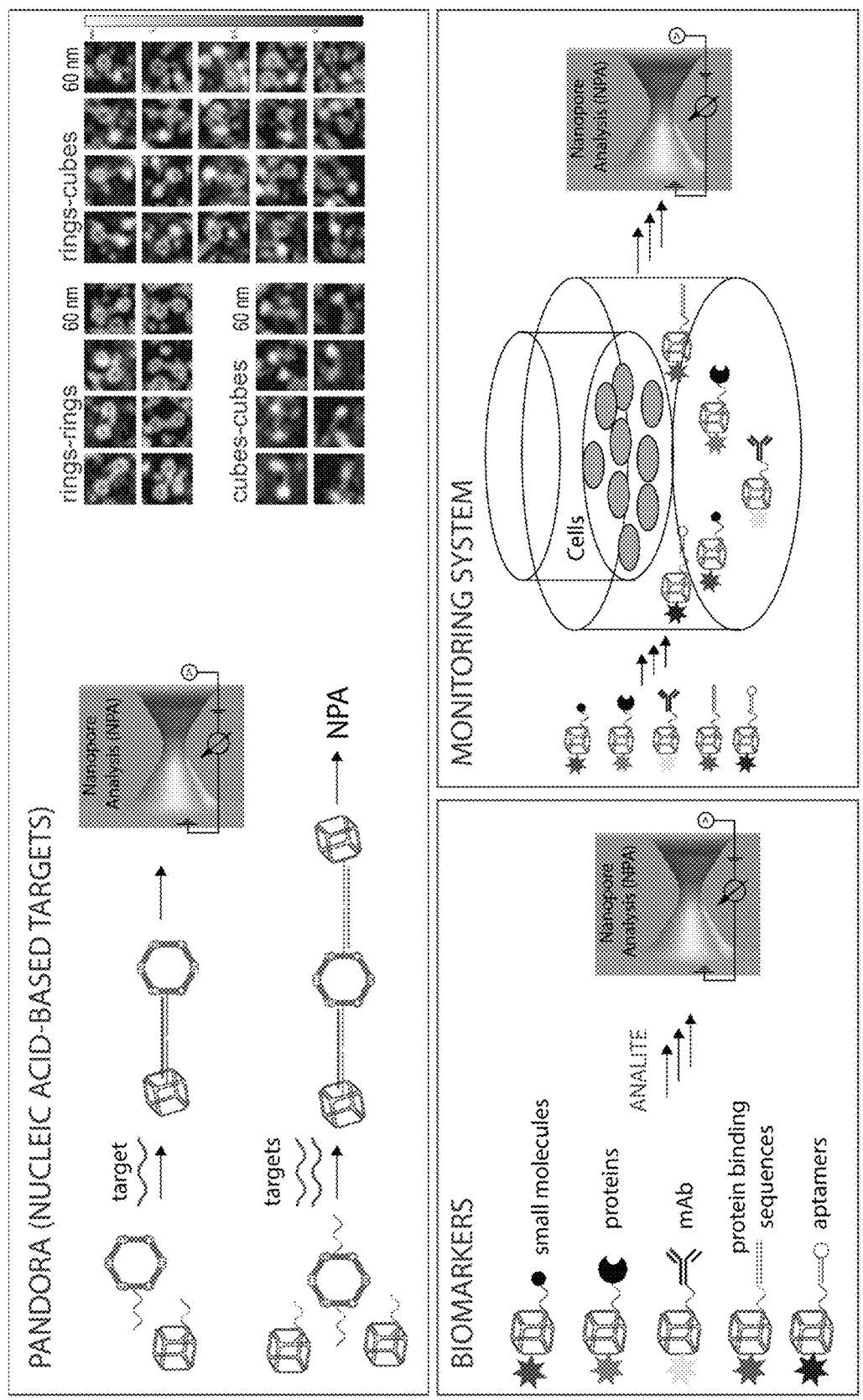

FIG. 26 is a summary of the various analytes or biomarkers the NANPs may specifically bind. The top panel illustrates various NANP linkages for two different NANP populations, including ring-ring, cube-cube and ring-cube. The bottom panels illustrates analytes that are biomarkers such as small molecules, proteins, mAb, protein binding sequences or aptamers, with nanopore system for measuring presence of analytes.

Figure 27:
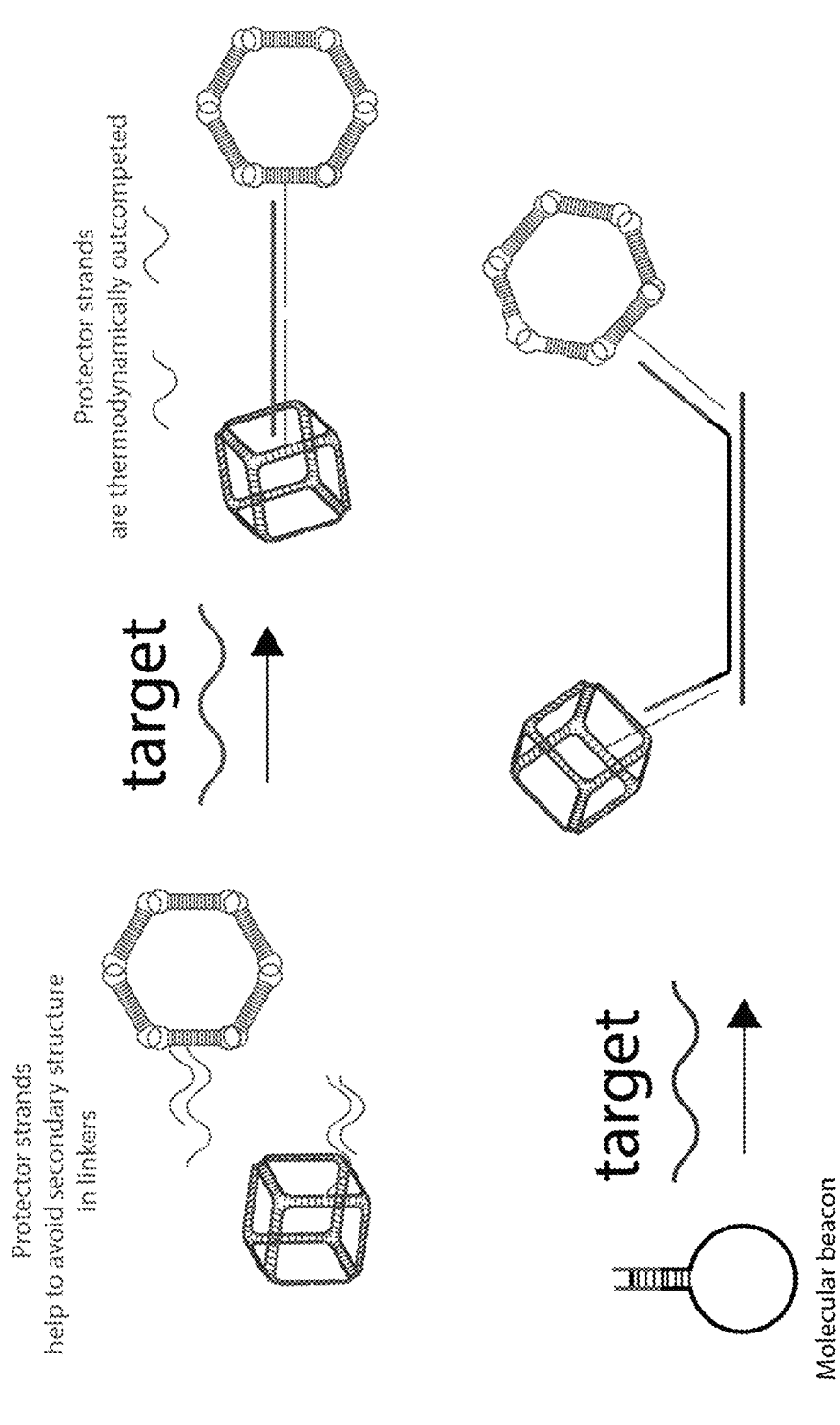

FIG. 27 is a schematic illustration of strand displacement to mimimize unwanted secondary structure in the analyte target sequence that could otherwise result in decreased binding (top panel). The bottom panel illustrates molecular beacon technology to facilitate analyte binding, including for detection of single nucleotide mutation.

Figure 28:
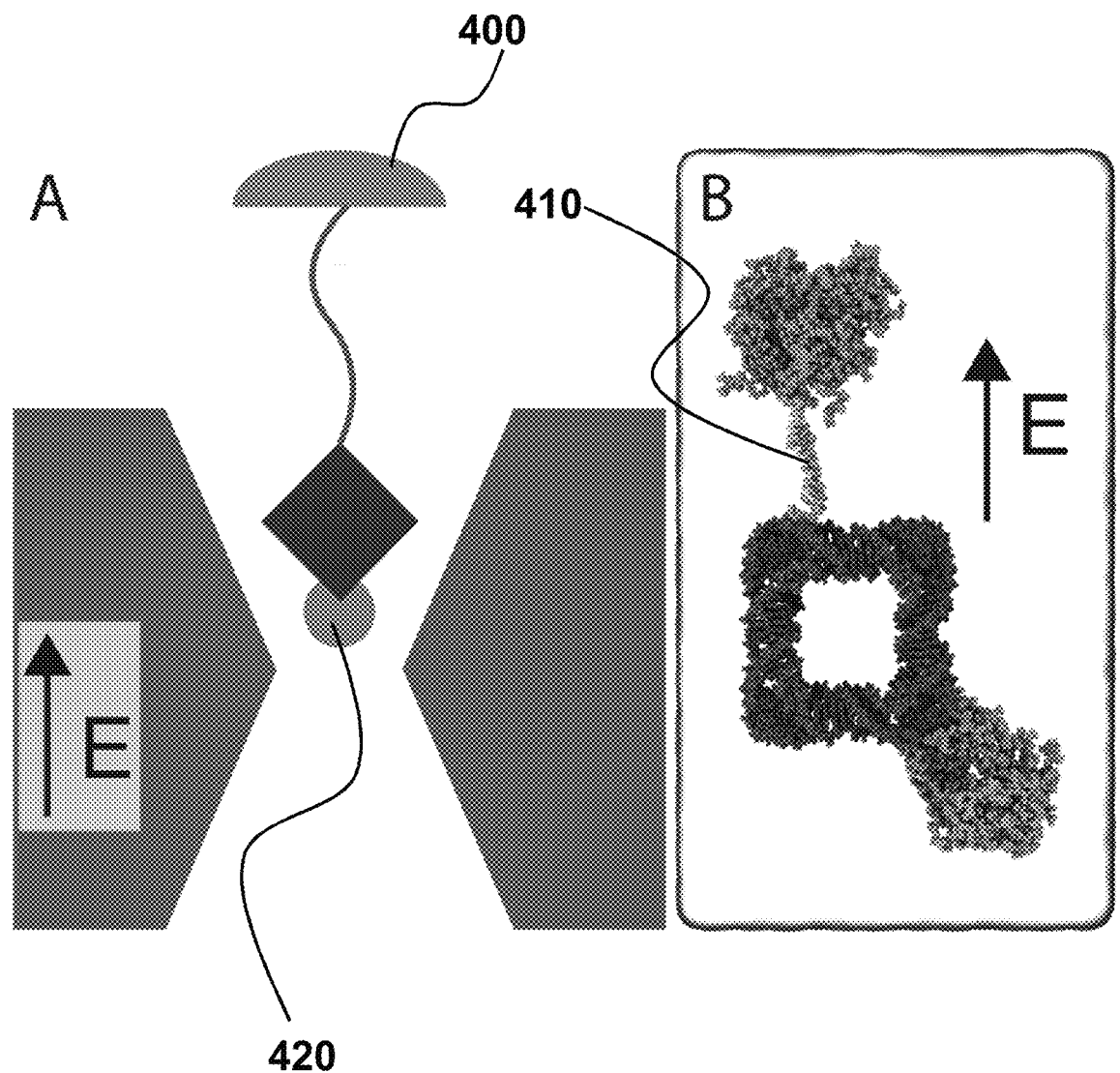

FIG. 28 illustrates nanopore detection of low abundance analytes, such as DNA and RNA binding proteins of low abundance. In the left panel, a NANP (illustrated as a square diamond) contains a protein (circle) bound directly to the NANP core structure that is driven toward a nanopore by an applied electric field E. As a NANP-protein complex approaches a nanopore, a guidance particle (the "parachute) bound to the NANP through a linker orients the complex to ensure its capture in a reproducible conformation. The right panel is a simulation system containing a transcription factor (bottom right) specifically bound to a DNA cube which in turn is bound to a guiding streptavidin protein ("parachute") through a peptide nucleic acid linker. A KCl solution is shown as a semitransparent surface.

Figure 29:
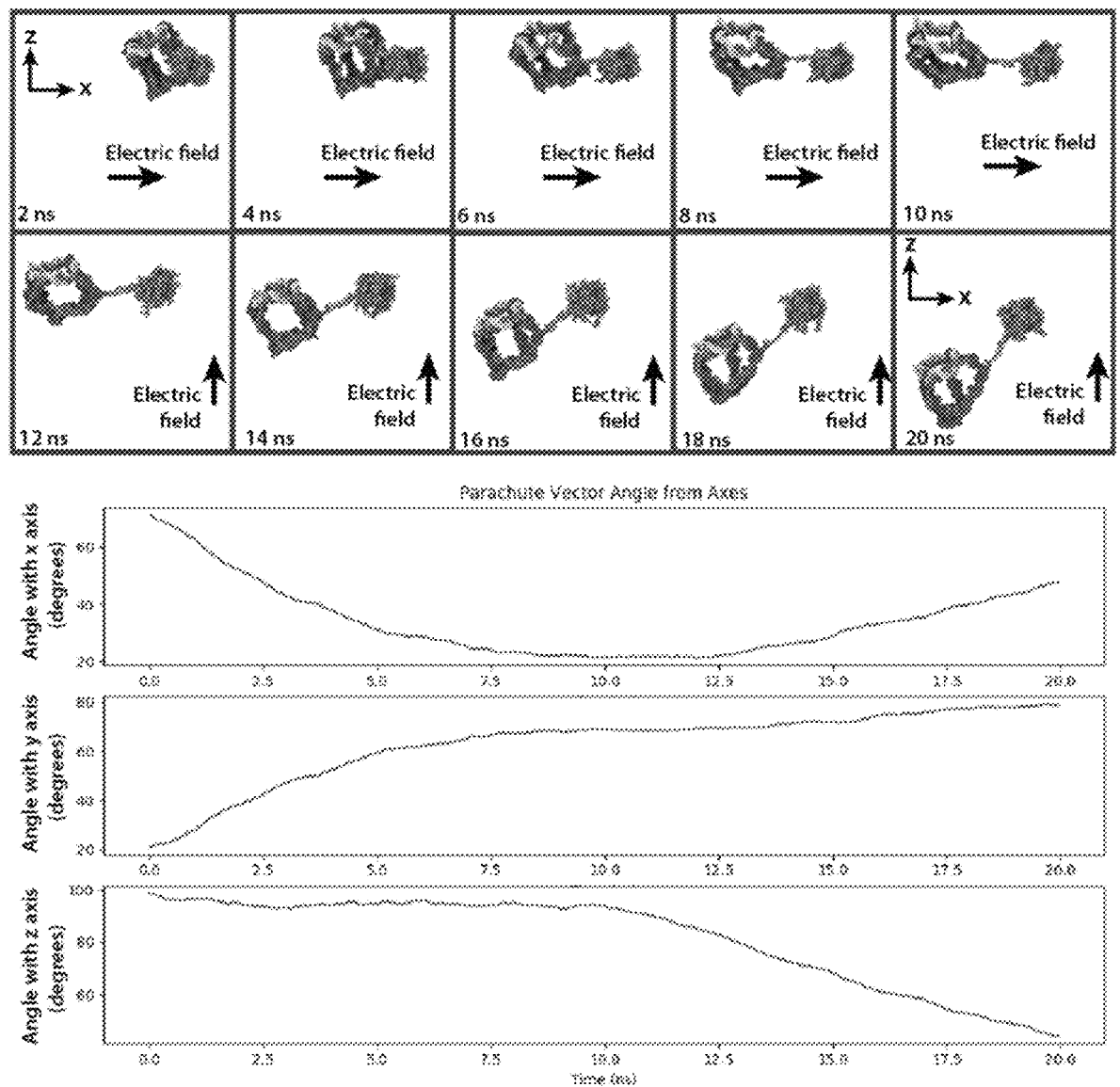

FIG. 29 provides molecular dynamics (MD) simulation of a NANP alignment in external electric field using auxiliary guiding (parachute) particle. (Top) Sequence of snapshots illustrating an MD simulation of a cubic NANP attached to a parachute particle (green) carried out under external electric field. The field was directed along the −x direction for the first 10 ns, and along the +z direction for the next 10 ns. Water and ions are not shown for clarity. The NANP-parachute assembly is seen to move in the direction opposite to the applied electric field as prescribed by the negative charge of the DNA. Under both field directions, the NANP-parachute assembly reorients to place the parachute particle at the trailing end of the assembly, controlling the orientation of the cube with respect to the applied electric field. (Bottom) the orientation of the NANP-Parachute particle with respect to the axes of the simulation system during the MD simulation.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

The system and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the system and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

"Nucleic acid nanoparticle" (NANP) refers to a particle having a characteristic cross-section or diameter that is less than or equal to 100 nm, including less than about 15 nm.

"Core NANP structure" refers to the central portion of the NANP formed by the nucleic acid sequence and corresponding structure of the assembled sequence. From the core NANP structure, a biomarker target sequence extends in a manner such that the corresponding biomarker may physically access and bind to the biomarker target sequence in a target specific manner. Accordingly, the biomarker sequence is configured so as to not bind to the nucleic acid sequence of the core NANP structure, but is able to bind to the specific biomarker target sequence. Such binding specificity may be described in terms of relative binding affinity, such as a binding affinity to a target biomarker that is at least 100-fold higher than non-specific binding. This can be achieved by designing the biomarker target sequence to have at least 90%, at least 95% or at least 99% sequence complementary to the target, including over a nucleotide number that is greater than or equal to 20, greater than or equal to 30, or greater than or equal to 50.

The present invention further includes nucleotide sequences that are biomarker target sequence extending from the core NANP structure, which hybridize under standard or stringent conditions to specified target binding regions of the biomarker. Hybridization procedures are useful for identifying polynucleotides with sufficient homology to the subject sequences to be useful as taught herein. The particular hybridization techniques are not essential to the subject invention. As improvements are made in hybridization techniques, they can be readily applied by one of ordinary skill in the art.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example in Keller, G. H., M. M. Manak (1987) *DNA Probes*, Stockton Press, New York, N.Y., pp. 169-170, hereby incorporated by reference. For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5 times Denhardt's solution, sonicated salmon sperm DNA (50 µg/ml), 0.1% sodium dodecylsulfate (SDS), and 10% dextran sulfate at 4° C., with washes at 42° C. in 0.2×SSC and 0.1% SDS.

An example of high stringency conditions is hybridizing at 68° C. in 5×SSC/5×Denhardt's solution/0.1% SDS, and washing in 0.2×SSC/0.1% SDS at room temperature. An example of conditions of moderate stringency is hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) supra or Ausubel et al. (1995) *Current Protocols in Molecular Biology*, John Wiley & Sons, NY, N.Y., for further guidance on hybridization conditions.

In general, salt and/or temperature can be altered to change stringency. For a DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

Other methods are readily available to one of ordinary skill in the art for obtaining analyte target sequences to specifically bind to an analyte binding region. Examples include strand displacement for biosensing, including equivalent to Roark et al. "Fluorescence Blinking as an Output for Signal for Biosensing" ACS Sensors 2016 1, 1295-1300 and molecular beacons, and schematically illustrated at FIG. 27. See, e.g., Tyagi and Kramer "Molecular Beacons in Diagnostics" F1000 Medicine Reports 2012, 4:10; Santangelo et al. "Nanostructured Probes for RNA Detection in Living Cells" Annals of Biomed. Eng. 34(1) January 2006, 39-50; Yang et al. "Molecular Beacon Imaging of Tumor Marker Gene Expression in Pancreatic Cancer Cells" Cancer Biol Ther. 2005 May; 4(5): 561-570, each of which are specifically incorporated by reference for use in linking NANPs by an analyte.

The NANP core structure may be further described in terms of a shape, density, effective size, or any other parameter that, in turn, impacts an electric parameter as the NANP transits a nanopore.

"NANP electronic signature" refers to the ability of an NANP to change an electrical parameter of a nanopore as the NANP is introduced to, and transits, the nanopore, such as ionic current. The NANP electronic signature may be measured over a time period, such as the time period during which the NANP biomarker-linked linear chains are forced to traverse the nanopore.

Accordingly, a "population-unique NANP electronic signature" refers to each NANP population affecting a change in an electrical parameter of the nanopore during transit. This recognizes that some variability within a population is to be expected, such as due to variability in nucleic acid self-assembly, orientation with respect to the pore, or even fluctuations in the immediate environment that can impact local electric field. On the whole, such as averaged over the population, the electronic signature is distinguishable from the next closest NANP electronic signature.

"Analyte" is used broadly herein to refer to a material or fragment of a material that is desired to be detected. Preferred analytes include a "biomarker", wherein the biomarker is associated with a health condition or state, including a disease state, an infection, or a contaminant. For example, the biomarker may be a protein, an antibody, a microRNA, a mRNA, DNA, and portions thereof, such as a polypeptide or a polynucleotide, including ranging from about 15 to 1000 residues in length, and any subranges thereof. The biomarker may be a biological material associated with one or more health states or conditions, such that detection of one or more biomarkers, or even the absence of biomarkers, provides a useful diagnosis. For example, the biomarker may be a small molecule, a nucleic acid, including DNA or RNA, a protein, including a nucleic acid binding protein, an antibody, including a monoclonal antibody, a protein binding sequence, a transcription factor, an aptamer, as well as fragments thereof. The biomarker may be associated with a type of cancer. In a similar manner, other disease states or conditions may be monitored by providing NANP biomarker target sequences that specifically bind to a biomarker associated with the disease state or condition. Depending on the specific analyte or biomarker type, an analyte target sequence part of or connected to the NANP is designed to specifically bind the respective analyte or biomarker as provided herein. The analyte target sequence may comprise one or more of a nucleotide, peptide, or synthetic construct. Representative examples are provided in FIG. 26.

The term "kit" is used broadly to refer to an assembly of components to be able to conduct a biomarker detection assay, including instructions for sample processing, analysis and read out.

"Multiplex detection" refers to the ability to measure a plurality of biomarkers.

"Nanopore" refers to a passage between a membrane having a diameter less than about 1 m, less than 100 nm, less than 12 nm, and preferably between about 7 nm and 12 nm, and any subranges thereof.

"Linear chain of biomarker-linked NANPs" refers to NANPs that are linked to other NANPs by a biomarker. A pair of NANPs may bind to a single biomarker but at different locations. In this manner, an NANP may have at least two different biomarker target sequences.

Referring to FIG. 25, a system to detect one or more biomarkers may comprise a plurality of NANPs 10, including a plurality of NANP populations, as illustrated by the different types of NANP core structures P1, P2 ... P5. Each NANP comprises a nucleic acid sequence 20 that assembles to provide a core NANP structure 30 (see, e.g., FIG. 1, where nucleic acid sequences 20 together form a hexagonal-shaped core structure 30). The presence of specific biomarkers allows for the formation of a linear chain 15 of NANPs 10, whose sequence is dependent on biomarker 50.

An analyte or biomarker target sequence 40 extends from the core (see, e.g., FIG. 8) or is part of the core (see, e.g., FIG. 28) and, as desired, a plurality of biomarker target sequences may be used. For clarity, in FIG. 25 each NANP 10 is illustrated with two biomarker target sequences 40, wherein the two biomarker target sequences specifically bind to different biomarkers 50 50a 50b 50c. The biomarker target sequences, depending on the application of interest, may be single stranded DNA (ssDNA) tails, RNA tails, or a combination thereof. Of course, the systems, kits and methods provided herein are compatible with a range of biomarker, types. For example, the NANP biomarker target sequences may correspond to any target that has a corresponding specific binding sequence 40 extending from the NANP 10. Accordingly, the biomarker-biomarker target sequence may correspond to any type of complementary ligand-receptor binding pair, including polypeptides.

Figure 8:
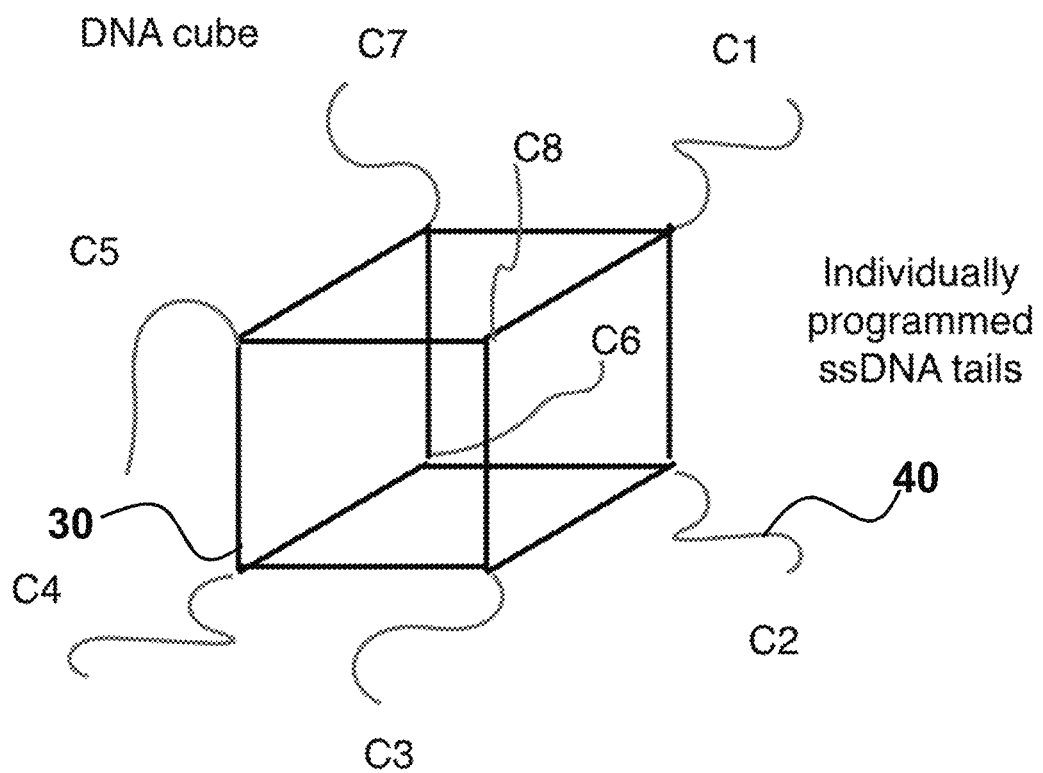
FIG. 8. Schematic representation of a cubic NANPs having eight different appendages, single DNA strands $C_1 \ldots C_8$, that each targets a different biomarker. As desired, the appendages can have any number of appendages, including one or greater than one, and may connect or extend from the core at an apex or corner (see, e.g., FIG. 9).
Figure 9:
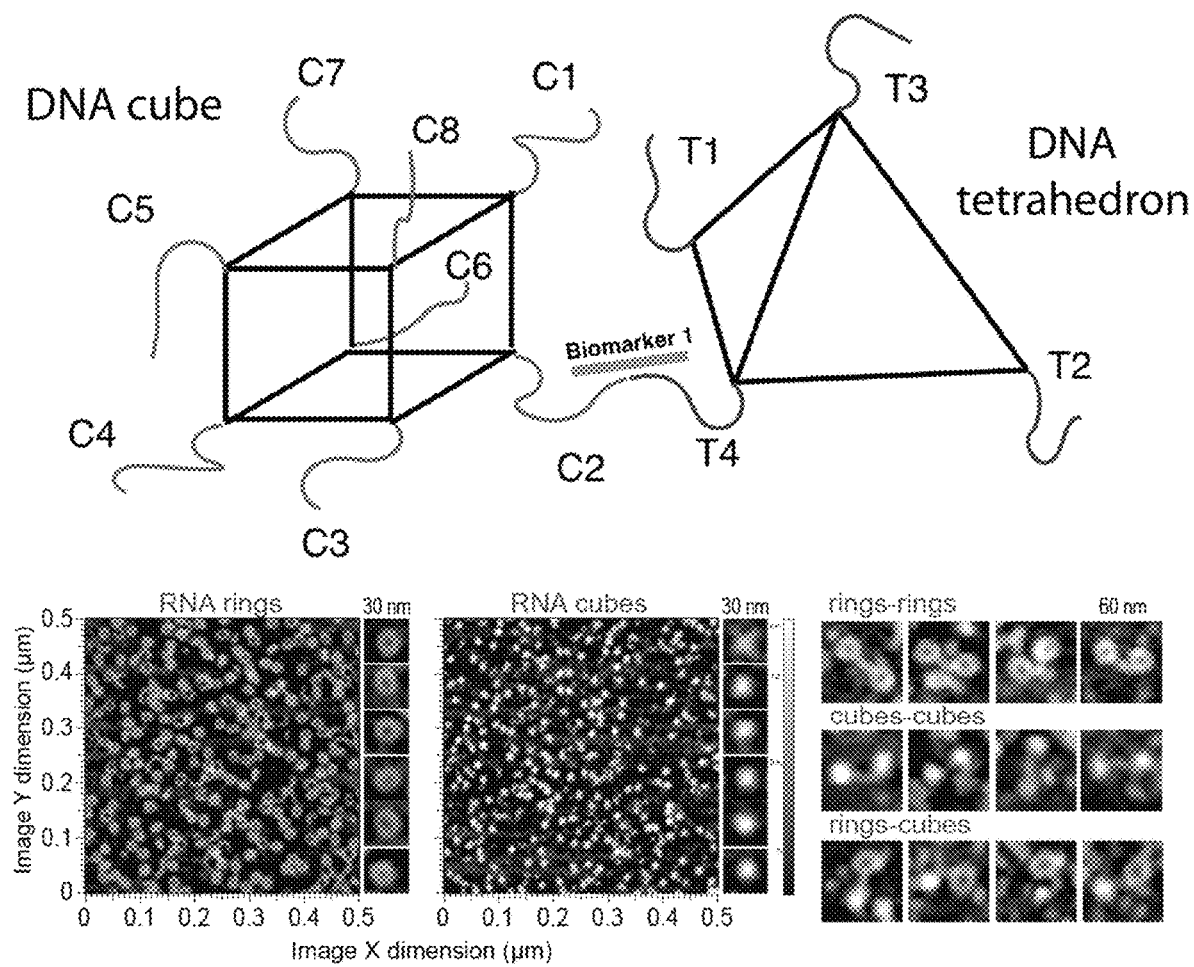
FIG. 9. Two NANPs connect into a linear chain in the presence of a biomarker, where the NANPs each target a specific sequence portion of the biomarker. (Top) Schematics of the assembly. A DNA cube is linked to a DNA tetrahedron in the presence of a biomarker that binds to both appendage C2 of the cube and appendage T4 of the tetrahedron. (Bottom) AFM images experimentally illustrating connection of two nanoparticles by a linker.
Figure 10:
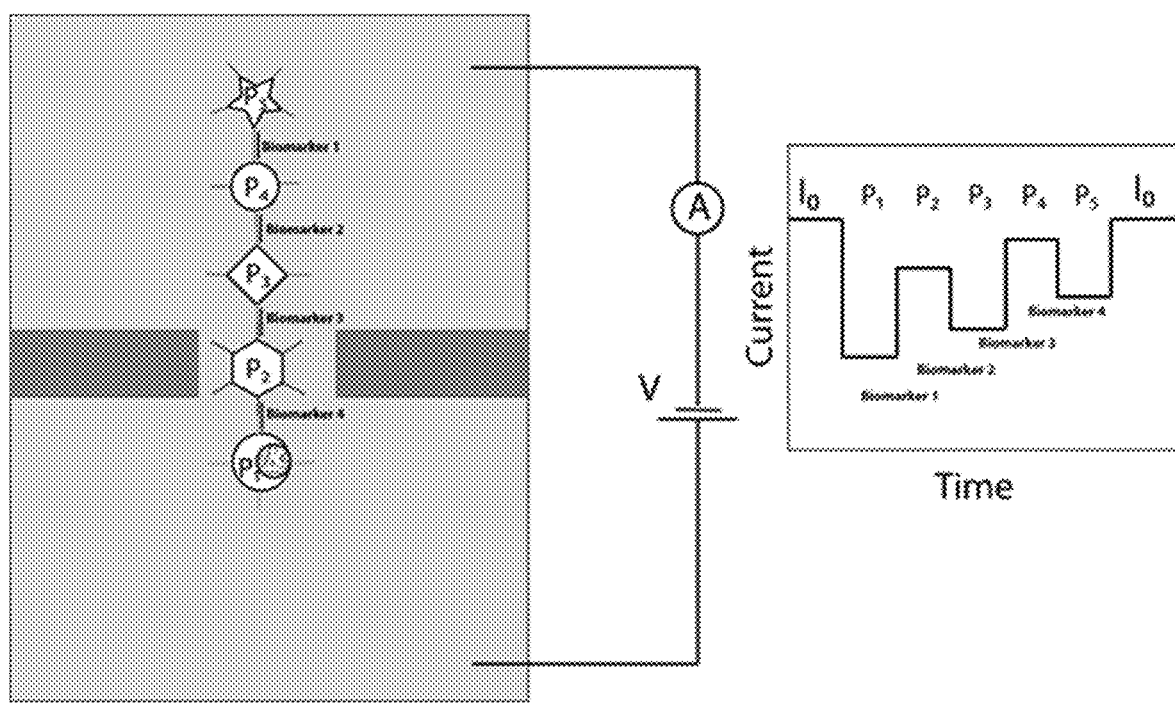
FIG. 10. Nanopore readout of biomarkers. Upon incubation, biomarkers 1-4 link nanoparticles in a particular order. As the chain of nanoparticles passes through the nanopore, the ionic current blockades produced by the biomarkers reveal the order in which the NANPs are connected, which in turn report on the presence of a specific set of biomarkers, as appendages of NANPs are selected to specifically bind to specific biomarkers.

A biomarker 50 may bind to its specific biomarker target sequence 40. For additional specificity, reliability, and sensitivity, there may also be configured a second binding event to a second population of NANPs. For example, the biomarker target sequences 40 of P1 and P2 may both be designed to be specific to one biomarker, but at different locations, such that P1 binds at one biomarker location 41 and P2 binds at a second biomarker location 42. Combinatorial systems may be readily designed by incorporating additional biomarker target sequences to NANP 10, including as illustrated in FIGS. 8-10.

An example of a system useful for reading out the sequence of NANPs is illustrated in FIGS. 1B and 25. The membrane 100 has a nanopore 150 that extends between a membrane first surface 110 and a membrane second surface 120. The nanopore may have a shape such that there is a minimum diameter toward a midpoint between the membrane surfaces and a maximum diameter positioned at the membrane surfaces. The nanopore may be described as having a characteristic diameter 155. The membrane surfaces 110 and 120 may define a surface of a first fluid compartment 130 (cis) and a second fluid compartment 140 (trans). A power supply 300 provides an applied electric potential between the fluid compartments to thereby drive a linear chain of NANPs through the nanopore, as indicated by arrows 310 in FIG. 25. A detector 320 detects an electrical parameter as the NANPs transit the nanopore from the first to the second compartment. A time course of electrical parameter as a linear chain of NANPs connected by biomarkers provides the ability to distinguish, in a sequence-specific manner, the NANPs. That time course, in turn, provides the ability to identify specific biomarkers, as the biomarker target sequence are biomarker-specific so that the order of the NANPs in a sequence can identify biomarker presence.

The systems and methods described herein provides a highly multiplex approach to disease condition diagnostics that combines advances from two separate areas of nanobiotechnology: nanopore sensing and nucleic acid nanoparticle (NANP) design and synthesis. Just like in a game of scrabble, nanoparticles are used as a kind of letters that can be connected in a certain order to spell out words. However, any two letters can be connected only if a certain biomarker is present in the sample. Simultaneous presence of several biomarkers results in a formation of linear string of NANPs (e.g., words) made up of several NANPs (e.g., letters). These words themselves, i.e., the sequence in which different types of nanoparticles are connected together, spell out the diagnosis. The nanopore is used to read out the diagnosis: the string of nanoparticles connected by biomarkers is driven through the nanopore by an applied electric field, producing a modulation of an electronic parameter, such as the nanopore ionic current. Because each type of a nanoparticle produces a characteristic ionic current blockade, the order in which the nanoparticles are connected can be accurately determined from an electrical parameter trace, such as an ionic current trace.

This example demonstrates that solid-state nanopores can be used to detect and characterize NANPs with high efficiency and precision. Akin to nanopore transport of deformable hydrogels,[59-61] nanopore transport of hollow and flexible NANPs can be expected to depend on their mechanical properties. Furthermore, distinguishing individual types of NANPs via a nanopore measurement can enable multiplexed detection of biomarkers using functional NANPs. Here, we characterize nanopore translocation of ring-shaped RNA and cube-shaped DNA nanoparticles, and find that mechanical deformation of NANPs governs their passage through narrow pores. Next, we examine the detection limit of such nanopore measurements and demonstrate that individual particles from a binary mixture can be identified based on an ionic current pulse produced by a single nanopore passage of a nanoparticle. In this manner, any number of NANPs can be designed to have a unique electrical parameter, such as ionic current blockade, so that any number of NANPs can be readily and efficiently detected, including any number of NANPs, with adjacent NANPs linked together via a biomarker.

There are numerous advantages of the method over present state of the art. Because of the combinatorial nature of the approach, a small number of NANPs can probe a large number of possible biomarkers, making it possible to use the same kit of nanoparticles for detection of a variety of health conditions. In comparison to conventional nanoparticles, the shape, size, charge, and composition of NANPs is predetermined by their design, which permits adjustment of their properties to produce large ionic current contrast for nanopore detection and diverse functionalization for biomarker binding. Relatively inexpensive one-pot assemblies result in a high yield production of NANPs with a high batch-to-batch consistency. This enables economic industrial scale production of nanoparticles in a cell-free system. Thermal and chemical stabilities of NANPs can be fine-tuned by introducing chemically modified nucleotides or by simply mixing the RNA strands in their composition with cognate DNA. This will allow for direct sampling of biological fluids (liquid biopsy). The use of synthetic DNAs additionally lowers the price and allows to control the properties of NANPs for particular nanomedical applications. RNA nanoparticles can be co-transcriptionally assembled, thus potentially allowing their production in cells. This represents an important feature that makes the NANPs production possible in patients' cells and their further use as for analysis of cytoplasmic biomarkers. Because of the negative charge and biological function of nucleic acids, NANPs are water soluble and not prone to aggregation. Electronic sensing of the reaction product provides the convenience of real-time detection, minimal instrumentation setup and potential portability. RNA and DNA aptamers can be used to expand the list possible biomarkers. This approach is not limited to detection of DNA or RNA biomarkers but can also be applied to protein biomarker detection by using nucleic acid aptamers as the nanoparticles' functional elements. Different types of NANPs are inert and will not interact with each other, thus allowing their simultaneous use in the reaction mixture. Matching the physical dimensions of the NANPs and the nanopore can eliminate signals from biomarkers themselves and increase sensitivity of the measurement, thus allowing detection of biomarkers at low (picomolar) concentration. In addition to medical diagnostics applications, the encoding principle described in the invention description can be used in homeland security (encryption) and biodefense (threat reduction) applications.

Figure 6:
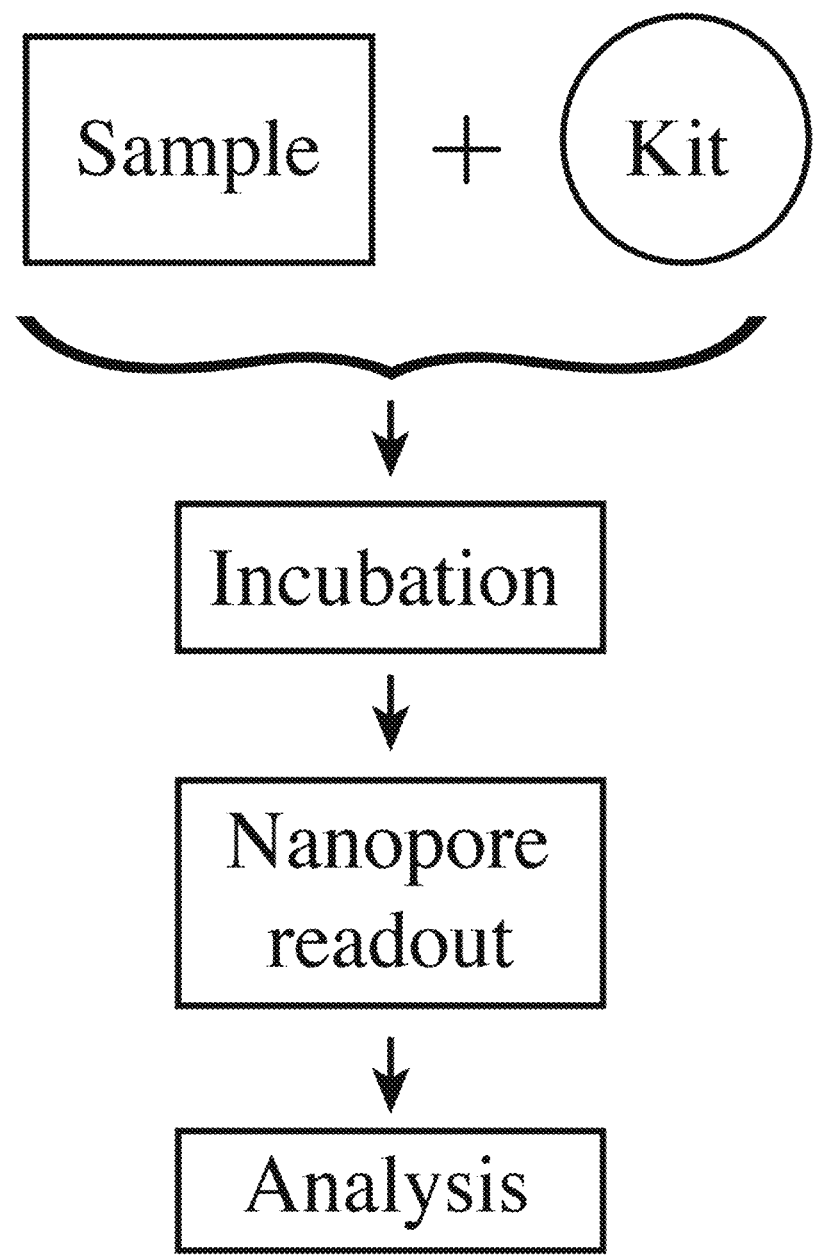
FIG. 6. Typical workflow for using the system for medical diagnostics.
Figure 7:
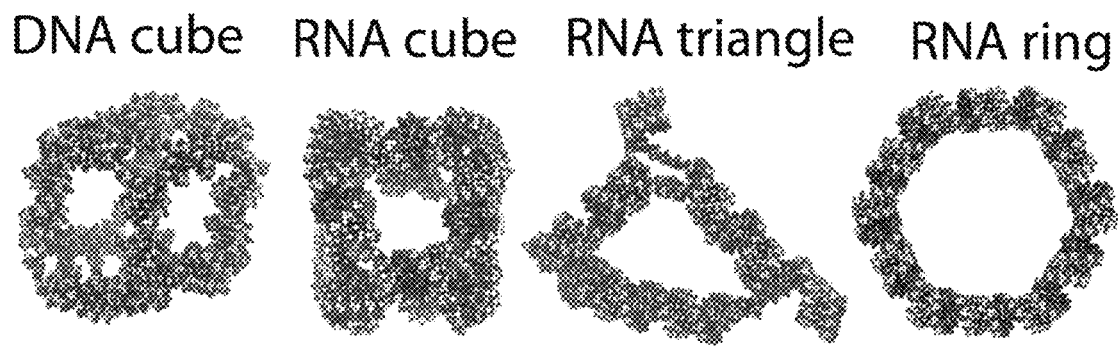
FIG. 7. Molecular models of exemplary synthesized DNA and RNA NANPs.

The system described herein can be used in the following way. A sample containing biomarkers is mixed with the detection kit comprising a plurality of nucleic acid nanoparticles (NANP) that are designed and synthesized to be able to detect particular biomarkers. Upon incubation, the mixture is used for nanopore measurements, producing recordings of the ionic current. The ionic current recordings are analyzed by the computer system, which determines the concentration of biomarkers in the sample. FIG. 6 schematically shows the typical workflow.

NANPs have shown promise as enablers of advanced biophysical studies and as probes for molecular sensing approaches. In this example, measurements of ionic current are used to characterize the process of NANPs transport through solid-state nanopores identifying conditions where deformability of the nanoparticles determines their transport characteristics. Specifically, we find that elastic deformation of NANPs in response to the applied electric field permits them to pass through nanopores smaller than the particle size, but only after the force on the particles in the nanopore exceeds a threshold value. Such deformation results in longer dwell times, which considerably improves NANP detection limits even at a high applied bias.

Furthermore, nanoparticle of different types, i.e., RNA rings and DNA cubes, produce distinct populations of ionic current blockade, and the type of individual particle transiting a nanopore from a particle mixture can be determined from a single current blockade. Such a tremendous distinguishability, combined with picomolar sensitivity, poises nanopore-based sensing of NANPs as an attractive system for a multiplexed detection platform for general biomarker sensing. Finally, nanopores are sensitive tools for investigation of the physical properties of multi-strand nano-assemblies, which are challenging to characterize otherwise, especially when several nanoparticle types of comparable sizes, charges, and molecular weights are simultaneously present in the mixture, even at pM concentrations.

Results: In this example, we explore nanopore transport of NANPs using two representative NA structures that are further referred to as DNA cubes and RNA rings. Each structure is composed entirely of either DNA or RNA strands, self-assembled according to the prescribed connectivity rules. The DNA cubes[47] are assembled through intermolecular canonical Watson-Crick base pairing, whereas the RNA rings[62] are formed via RNA-RNA tertiary interactions known as kissing loops.[63] To initiate the magnesium dependent kissing loop interactions, individual monomers of RNA rings must be pre-folded prior to assembly. In contrast, monomers entering the composition of DNA cubes were designed to avoid any internal secondary structures.

To assess the physical characteristics of these NANPs we used atomic force microscopy (FIG. 1A) and gel electrophoresis (FIG. 1B), both of which show the formation of monodisperse and highly regular structures. Our nanopore setup is schematically shown in FIG. 1C. The nanopore forms a solitary electrolyte contact between the cis and trans side of the membrane. Applying an electric field across the pore produces a steady-state ion current, as well as a localized electric field that captures and drives charged nanoparticles through the pore. Each time a nanoparticle interacts with the pore, the ion flux through the pore is reduced transiently, producing an electrical spike.

Previously, increasing the electric field was found to facilitate nanopore capture of biomolecules from the bulk solution and increase the signal-to-noise ratio of the produced electrical spikes[64-65] A major downside, however, was the shorter duration of the nanopore translocation process, which compromised detection efficiency. In the case of NANPs, however, we find that it is possible to increase the capture rate without compromising the detection efficiency. Employing pores with diameters in the range of 9-10 nm, just smaller than the size of a NANP, forces NANPs to reside at the nanopore entrance for a prolonged time before being squeezed through the nanopore by the electric field. As a result, every particle is detected with high signal-to-noise ratio using high-bandwidth electronics.[66]

Figure 2A:
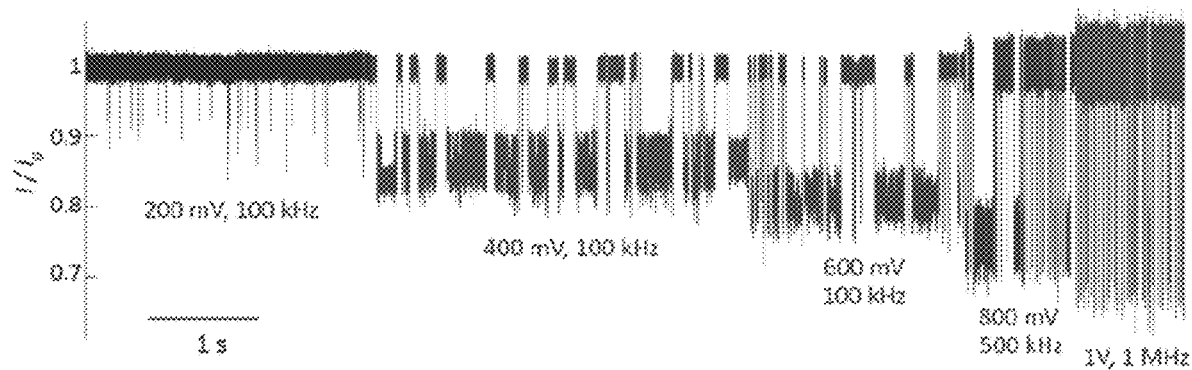
FIG. 2A. Deformation-controlled transport of NANPs. Normalized current traces obtained for RNA rings interacting with a 9 nm nanopore at 200, 400, 600, 800, and 1000 mV (for 400 mV and 600 mV data, open pore segments are excised to increase number of observed events).

Sample current traces for RNA rings through a 9 nm pore at different applied voltages are shown in FIG. 2A. The current is normalized by its open pore value to highlight changes in the fractional blockade. We find that the fractional current blockade increases with applied bias. Further, we observe a seemingly counterintuitive result of longer dwell times at 400 mV than at 200 mV bias, which defies the previously observed trends in translocation of DNA[64] and proteins[65] through nanopores. Increasing the applied bias beyond 400 mV reveals the trend expected with translocation, namely, faster dwell times with increasing voltage. We rationalize these results as follows: below a certain voltage threshold, the RNA rings only collide with the pore and do not translocate, because the electromotive force that drives the NANPs is insufficient for squeezing them through. As a result, the NANPs dwell in the pore entrance for durations that span orders of magnitude.

Beyond a certain threshold defined by the electric field strength, the NANPs can traverse the pore. A similar mechanism was previously suggested to govern transport of double-stranded DNA through very narrow pore in silicon nitride membranes,[67] as well as the docking-translocation of DNA origami nanoplates in 5-30 nm nanopores.[68] See also U.S. Pat. Nos. 8,748,091 and 8,394,584 for various nanopore and nucleotide characterization systems, including associated sensors, detectors and power controllers, which are specifically incorporated by reference herein. The deformation-controlled mechanism of NANPs translocation is also borne out by the observation of increasing fractional blockades with voltage, FIG. 2C, which reports on how deep the NANPs enter into the pore constriction.

Figure 2B:
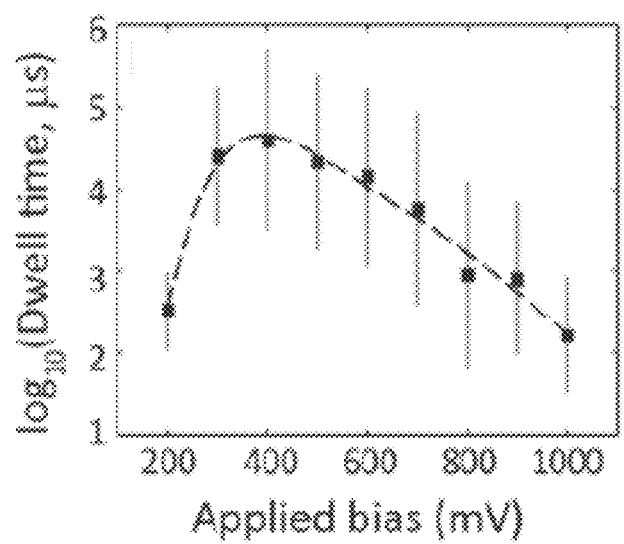
FIG. 2B. Mean dwell-time vs. applied bias for RNA rings (dashed line is a trend line fit to guide the eye). Vertical lines for each data point represent ±1 standard deviation in the corresponding dwell-time distributions.
Figure 2C:
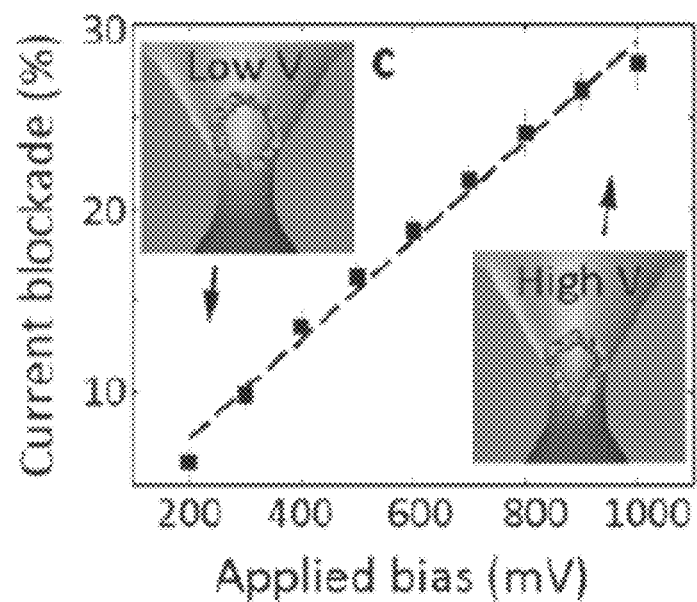
FIG. 2C. Mean fractional blockade versus applied bias (dashed line is a linear fit). Inset schematics illustrate the increasing fractional blockades with increasing voltage.
Figure 11:
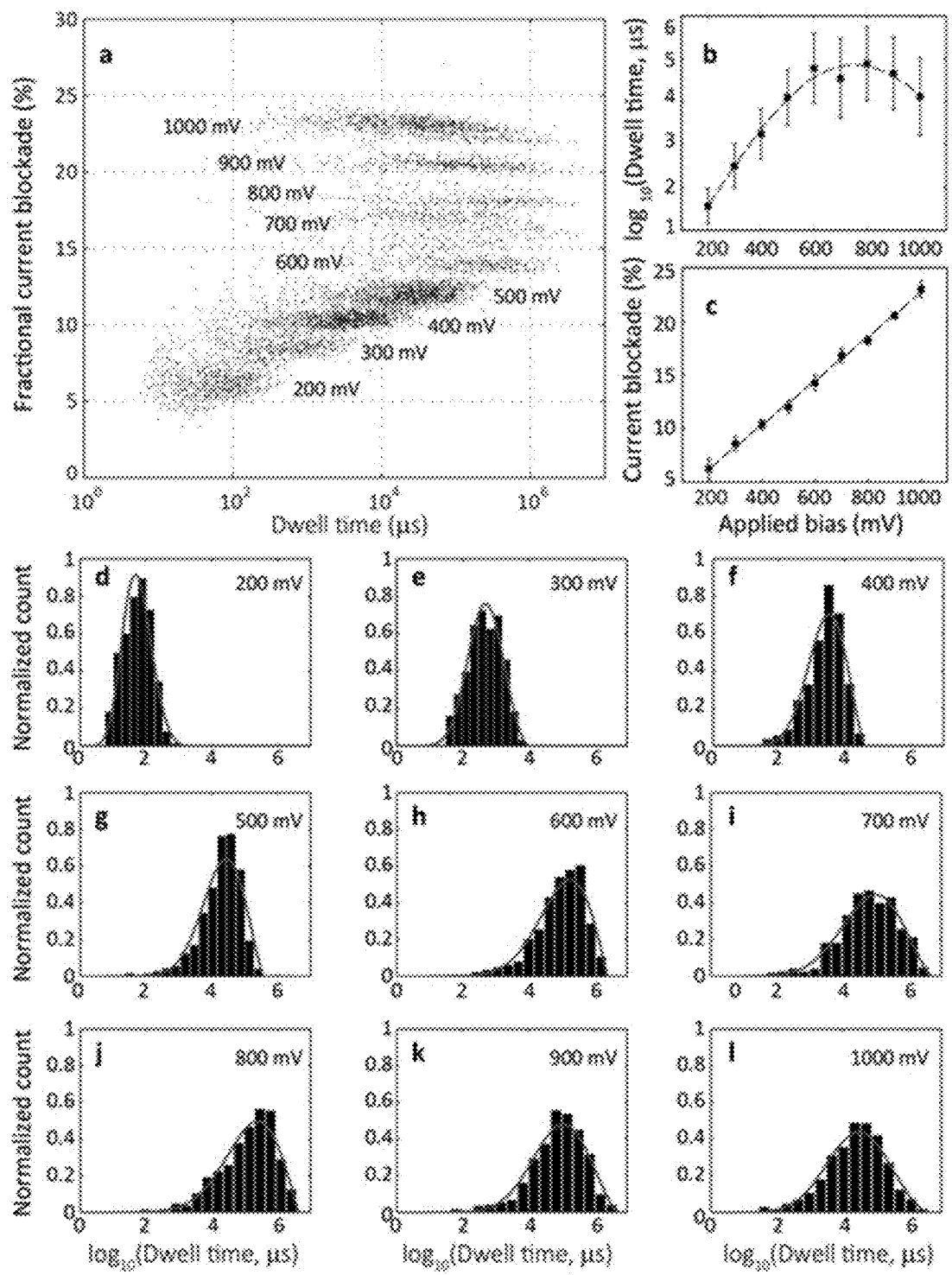
FIG. 11. The top left panel (labeled as "a") is a scatter plot of fractional current blockade and dwell time for translocation of the RNA rings through a 9 nm-diameter nanopore at different voltages. Top right panel (labeled as "b") is a plot of dwell time versus applied voltage with the panel immediately below (labeled as "c") a plot of fractional current blockade versus applied voltage. The remaining panels are plots of dwell time distribution at different applied voltages fitted with the generalized extreme value distributions. Experiments performed with 400 mM KCl (10 mM Tris, 2 mM $MgCl_2$, pH 7.9).

The transition from collisions to translocations manifests itself in FIG. 2B as a peak in the dwell times at ~400 mV; although we find the exact location of the peak to depend on the pore and particle geometry. Another example of dwell-time dependence is shown in FIG. 11, where the peak voltage is at ~700 mV. Note that the nanopore shape drawn in FIG. 1C is derived from the prior tomography-based studies of pores produced using a similar fabrication protocol.[69-70]

The results show that nanopore translocation of NANPs involves processes that occur at two separate timescales: the dwell timescale associated with NANPs residing at the nanopore entrance and the passage timescale associated with actual nanopore translocation of NANPs. Whereas the dwell times of the RNA rings span several orders of magnitudes (see FIG. 11 and FIG. 4), the passage times are expected to be much shorter than the dwell times, given that the nanopore translocation can only happen after deformation and/or buckling of the stalled nanoparticles. Thus, although we would expect to see deeper blockades when NANPs pass through the pores, we do not detect them presumably due to the passage timescales shorter than those detectable by our electronics (>1 s detection limits).

Figure 2D:
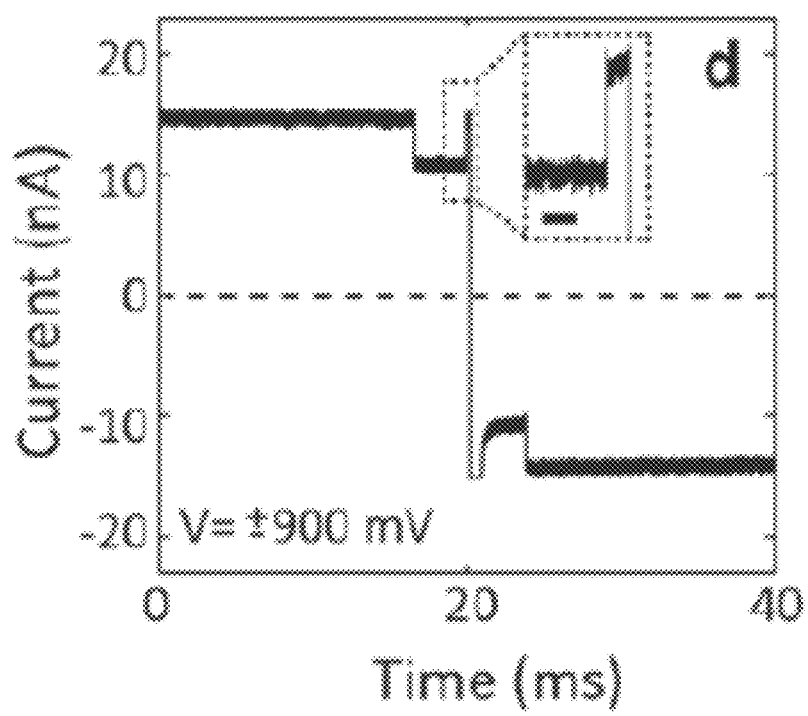
FIG. 2D. Recapture of an RNA ring. Switching polarity of the voltage bias immediately after a long ionic current blockade produces a similar-amplitude opposite-polarity blockade event, confirming nanopore translocation of NANPs and further suggesting that NANPs retain their structure after translocation (inset scale bar: 300 µs). Experiments performed with 400 mM KCl (10 mM Tris, 2 mM $MgCl_2$, pH 7.9).
Figure 12:
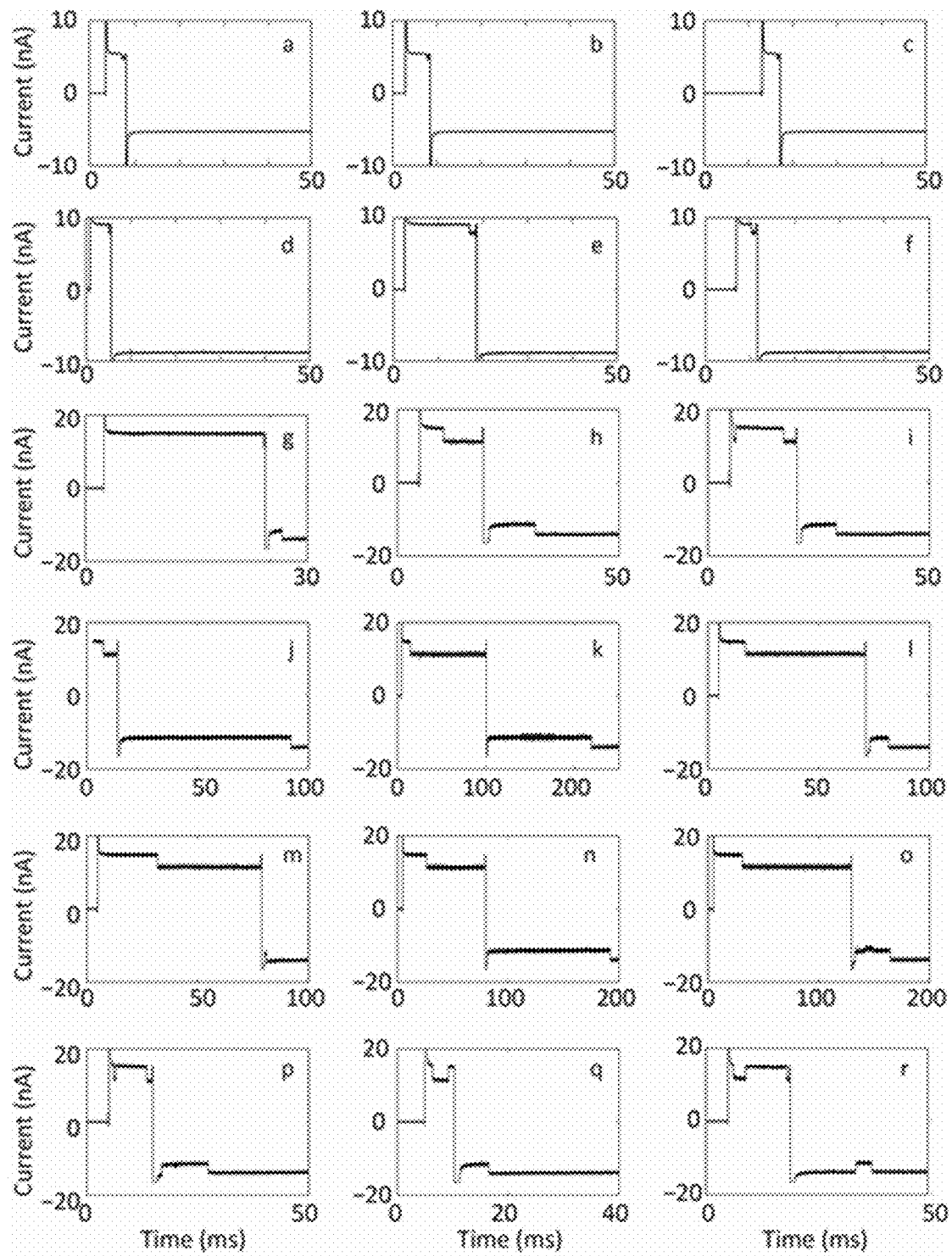
FIG. 12. RNA rings after capture at 300 mV (a-c) and 500 mV (d-f) cannot be recaptured after reversing the bias polarity, indicating that current blockade is only due to collision of the rings with the nanopore without translocation. (g-r) Capture and translocation of RNA rings at 900 mV and their recapture at −900 mV. Experiments performed with 400 mM KCl (10 mM Tris, 2 mM MgCl$_2$, pH 7.9).

In order to verify successful translocation of NANPs through the nanopore, we performed nanopore recapture experiments (see FIG. 2D).[71] In these experiments, a transition in the pore current level from the NANP-occupied state back to the open state triggers the hardware to reverse the bias polarity after a set delay, which we selected to be 200 µs. Such rapid switching of bias polarity results in recapture of the same NANP that just passed through the nanopore. Recapture of the rings, which occurs with a probability of ~10%, validates our interpretation of long-lasting blockades as NANP capture terminated by nanopore translocation. Furthermore, ionic current blockades produced by both translocation and recapture are very similar (more example events are shown below, FIG. 12), with slight variations in the exact signal amplitude and durations (<20%) that may be accounted for by the nanopore shape asymmetry. This finding suggests that nanopore translocation does not disrupt the structural integrity of the rings, as linear RNA molecules of similar mass are not expected to produce signals of similar amplitudes and durations given that the translocation kinetics of a NANP is conditioned by both the size of the ring and its mechanical compliance.

In a typical nanopore experiment, the voltage applied across the pore serves to facilitate the capture of analytes as well as to translocate them through the pore. Therefore, capture and translocation are coupled, which makes detection of trace amounts of analyte challenging. Indeed, although detection limits for a particular analyte can be increased by increasing the applied bias,[72] any increase in applied bias would also speed up the translocation process, which usually compromises detection. However, in contrast to free translocation of particles through nanopores that are larger than the analytes, in the regime of deformation-controlled transport, capture and translocation can be decoupled.

Figure 3:
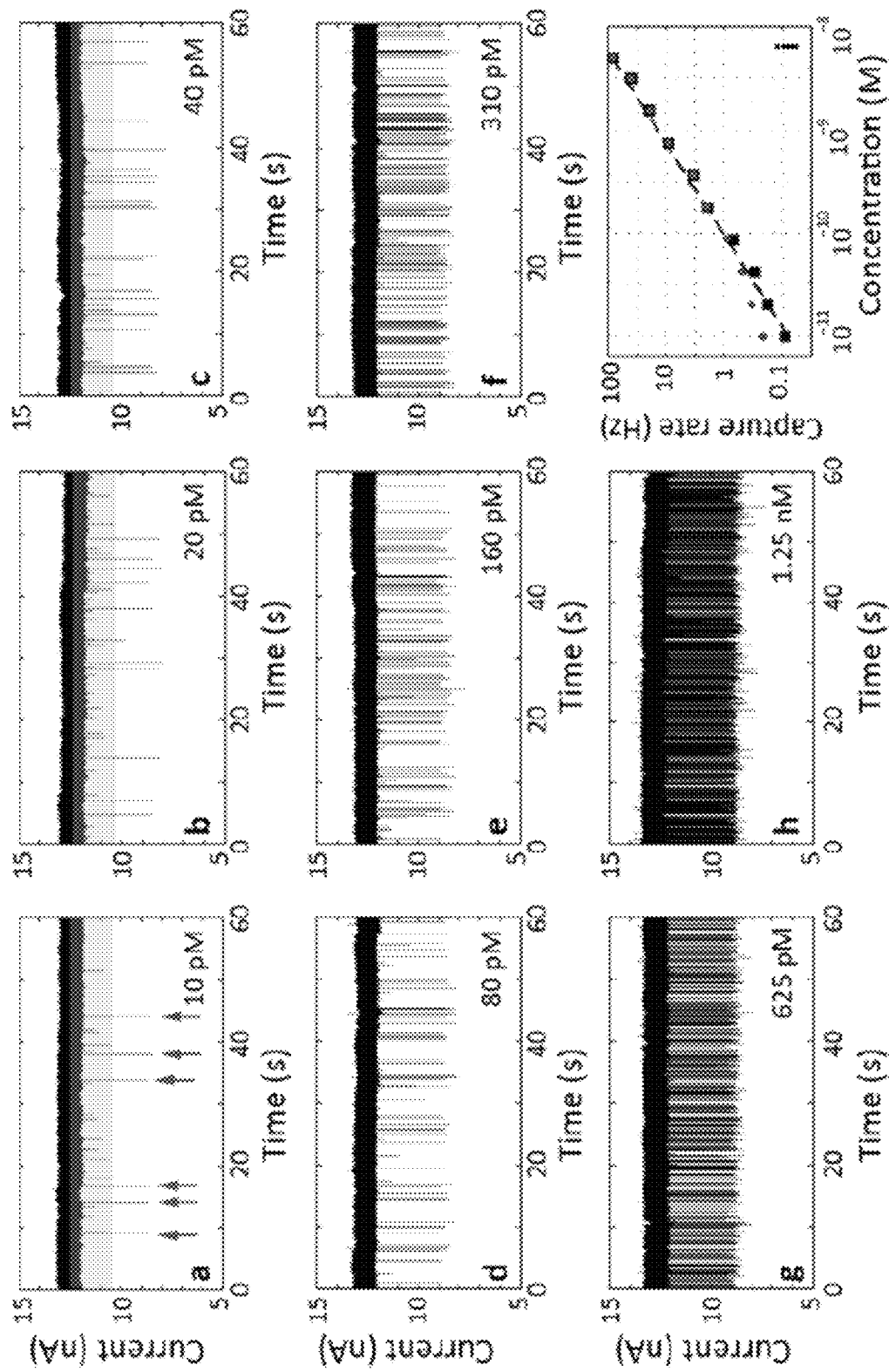
FIG. 3. Concentration limit of NANP detection. Referring to the inset labels a-i in each of the plots, Current traces recorded from samples containing RNA rings at different concentrations are provided in plots a-h. All measurements are carried out using a 9 nm pore at 1V applied bias; the data are low-pass filtered at 500 kHz. Shaded regions in plots a thru c highlight occurrence of shallow events. The lower rate plot (i) illustrates capture rate versus concentration of RNA rings. Red circle symbols: capture rate based on total number of events. Black square symbols: Capture rate after omission of the shallow events with fractional blockade less than 15%. Experiments performed with 400 mM KCl (10 mM Tris, 2 mM $MgCl_2$, pH 7.9).

In FIG. 3, we show example 60 s current traces for RNA rings at 1 V applied bias for concentrations ranging from 10 pM to 1.25 nM. The experiment was carried out by serial dilution (2×) of a 5 nM solution of RNA rings, followed by recording of ~150 s of data at each concentration for mean capture rate calculation.

The bottom right panel of FIG. 3 displays a log-log plot of the mean capture rate of the RNA rings as a function of their concentration. Red markers were obtained by calculating the capture rate based on the total number of recorded events, while the black markers represent capture rates for only events with amplitudes that are larger than 15% of the open pore current (mean blockades of rings ~30%). Omitting the shallow events, a power law fit to the log-log data yields a power of 1.12, which closely matches the expected linearity (1.0 power), the discrepancy either stemming from volume estimation error or from pipette miscalibration. However, it is noteworthy that omitting the random (and rare) shallow events that result either from pore surface contamination or from buffer contamination allows us to push detection limits to the pM levels. Finally, we have calculated the capture radius of the rings from the observed capture rates, yielding values of ~100 nm; the diffusion coefficient of an RNA ring was estimated to be 40 µm²/s using the nominal size of the ring and the Einstein-Stokes equation. We note that for a previous study of double-stranded DNA capture into small (4 nm diameter) nanopores,[72] the capture radius was found to be commensurate with the DNA radius of gyration. In contrast, the higher voltages used in our experiment, coupled to high efficiency detection that results from deformation-controlled transport, yields a capture radius for the deformable structure that is an order of magnitude larger than its radius of gyration.

After having characterized the nanopore transport of RNA rings, we have carried out similar measurement using DNA cubes, see FIGS. 1 and 13. Overall, DNA cubes exhibit very similar transport behavior, including very broad dwell-time distributions, increased fractional blockade with increasing voltage, and non-monotonous behavior of dwell-times with increasing voltage values. A simple theoretical estimate of the fractional blockade produced by a DNA cube is in good agreement with the results of our measurements.

Figure 4:
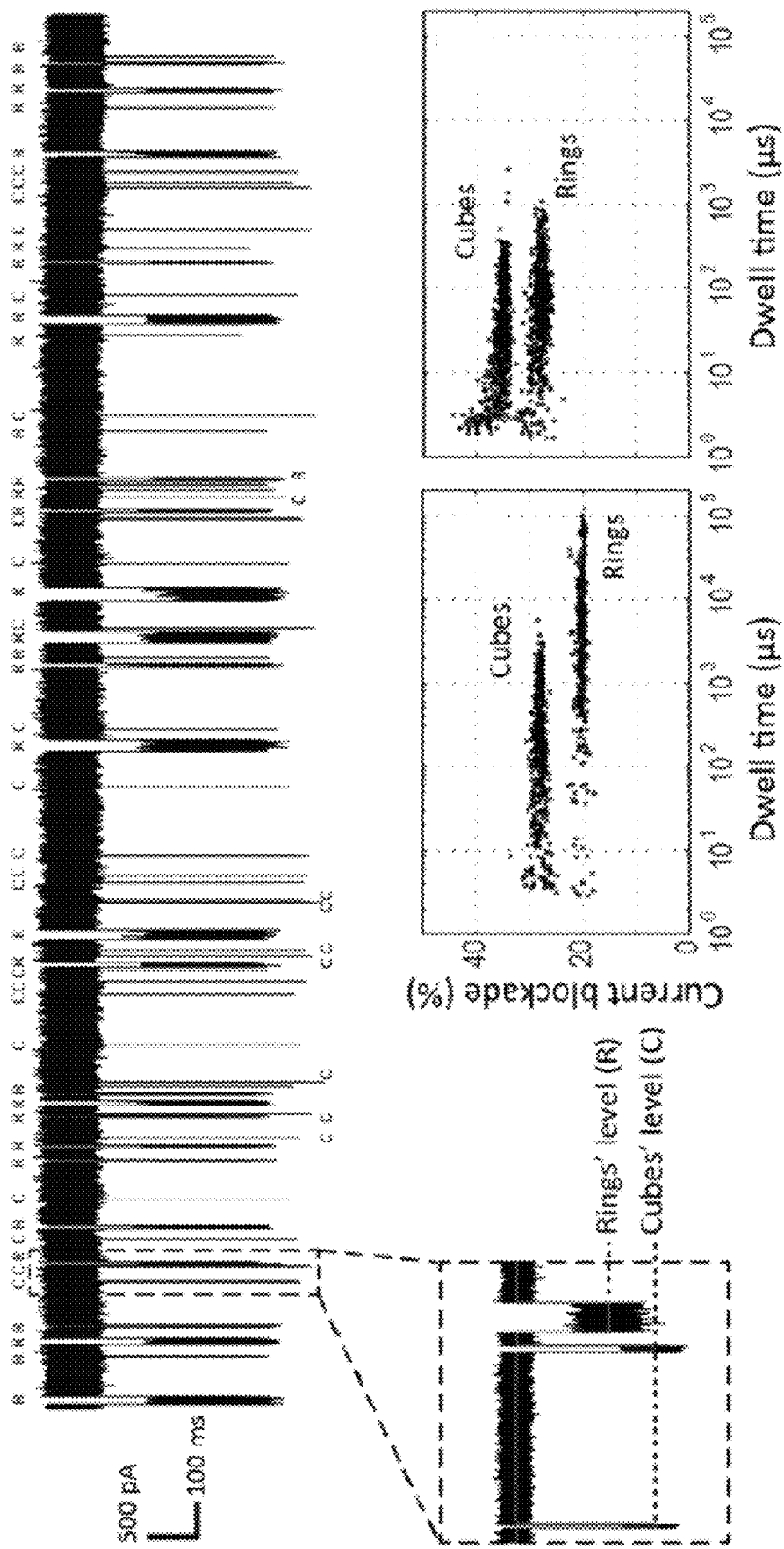
FIG. 4. Discrimination of RNA rings from DNA cubes. The top panel is a plot of current traces measured from a binary mixture of DNA cubes and RNA rings (1 nM ring: 1.4 nM cube). The translocation experiments are performed using a 9.5 nm diameter pore, with a 500 mV transmembrane voltage; data are low-pass filtered at 500 kHz. The bottom left panel is a magnified view of the current trace from the top panel, as indicated by the dashed portion of the current trace, indicating two distinct blockade levels associated with each nucleic acid nanoparticle. The two scatter plots at the bottom right illustrate the fractional blockade versus dwell time measured at 500 mV applied bias. The results show two distinct populations corresponding to the DNA cubes (n=422) and the RNA rings (n=376). The bottom right panel is under an applied bias of 800 mV. In this panel, data are processed using a 1 MHz low-pass filter ($n_{cube}$=573, $n_{ring}$=498). Experiments performed with 400 mM KCl (10 mM Tris, 2 mM $MgCl_2$, pH 7.9).

Owing to their 3D structure, DNA cubes can block a larger volume of the pore in its high electric field zone, hence causing larger current blockades. This permits the use of the same pore to discriminate DNA cubes from RNA rings. FIG. 4 top panel directly shows the possibility of such shape differentiation. Clearly, two distinct blockade levels are present in the trace, as further exemplified in the close-up of FIG. 4 (middle left panel). Experiments conducted with individual NANPs as well as their binary mixtures (1 nM ring: 1.4 nM cube) confirmed that the higher-level blockade belongs to the cubes (see FIG. 14). The scatter plot of the fractional blockade vs. dwell-time clearly demonstrates two mutually exclusive populations, indicating that cubes and rings can be differentiated based on single pulses with >99% efficiency (FIG. 4 middle center panel). In other words, each event in the scatter plot can be mapped to either a ring or a cube, based on its fractional blockade amplitude. Given that both particles deform as they enter the pore constriction, increasing the applied bias to 800 mV results in increased fractional current blockades for both NANPs while also reducing their corresponding mean dwell times (FIG. 4 middle right panel).

These results were reproduced using 15 different nanopores in the 9.5±1 nm range at different applied voltages despite small variabilities in the fractional current blockades and translocation threshold voltage that are related to the exact nanopore geometry. It is important to note that in the gel electrophoresis experiment performed using a ring-cube mixture, FIG. 1B, the two types of NANPs, despite being different in shape and size, migrate very similarly and hence are difficult to distinguish from one another. In contrast, the deformation-controlled transport through nanopores enables accurate differentiation of the two NANP species. An even more accurate quantification of a composition of a NANPs mixture, in addition to measuring the capture rate, would require accounting for the relative capture probability for each nanoparticle, which in practice would reduce to a calibration measurement for each particle type.

Figure 5A:
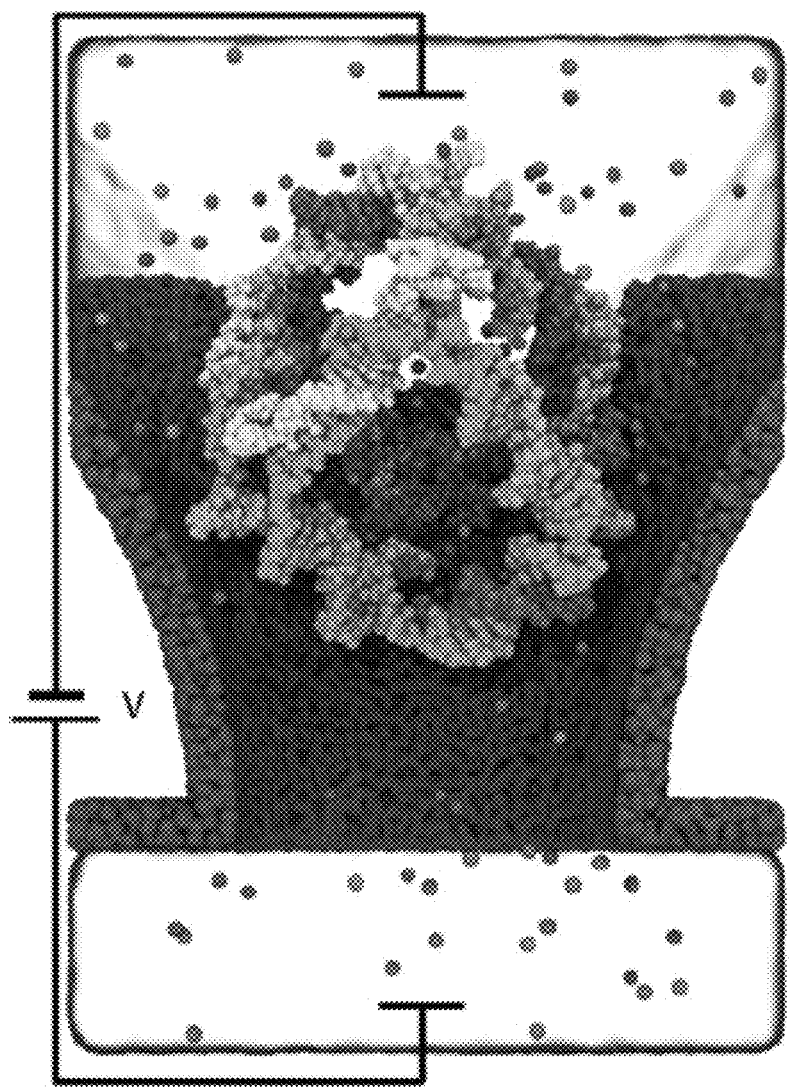
FIG. 5A. MD simulations of NANPs' translocation through a solid-state nanopore. Typical simulation system containing a nanopore (gray), a DNA cube (colors), water (semitransparent surface) and ions (spheres). The diameter of the nanopore constriction is 9 nm.

To elucidate the microscopic mechanism of NANP permeation through solid-state nanopores and to obtain an independent assessment of the ionic current blockade levels, we constructed several all-atom models of a nanopore system containing either a DNA cube or an RNA ring nanoparticle (FIG. 5A). To increase the computational efficiency of MD simulations, the nanopore shape was chosen to reproduce the cis half of the experimental nanopore system, with the trans side cut off at the membrane mid-plane. Prior to simulations of the nanopore transport, the nanoparticles were equilibrated for at least 60 ns in bulk 400 mM KCl solution until their root-mean square deviation (RMSD) from the idealized geometry had reached steady values of 1.2 and 0.6 nm for the DNA cube and the RNA ring, respectively (FIG. 18). Such rather large equilibrium RMSD values reflect considerable structural fluctuations that nevertheless do not affect integrity of the particles, Indeed, more than 90% of all basepairs remained intact during the free equilibration simulation (FIG. 18).

To simulate nanopore transport, equilibrated NANPs were placed at the opening of the nanopore, FIG. 5A, and, following short equilibration, were simulated under a transmembrane bias of either 200 or 500 mV. Several independent simulations were performed at each bias; Table 1 provides a summary of all MD runs. In some simulations performed at a 500 mV bias, the particles were observed to pass through the nanopore constriction, rapidly exiting on the trans side; one such trajectory is featured in FIG. 5B. Interestingly, the DNA cube maintained its integrity after the translocation (FIG. 19).

In the majority of the simulations, however, the particles became wedged at the cis entrance of the nanopore. Two such stable conformations are shown in FIGS. 5C-5D; FIGS. 20-24 illustrate representative simulation trajectories. Once the structures had reached an equilibrium conformation and their movement effectively ceased, see FIG. 17 and Table 1, we calculated the ionic current for each of the structures directly from the motion of the ions through the nanopore. For comparison, we also simulated the ionic current through the nanopore containing no nanoparticles. FIG. 5E plots the current blockade percentage $100 \cdot (I_o - I)/I_o$, where $I$ is the ionic current passing through the nanopore, and $I_o$ is the open-pore current. The DNA cube blocked a higher percentage of the current than the RNA ring in our simulations, at both biases, which is in agreement with our experimental data. Note that, because of the difference in the geometry of the simulated and experimental nanopore systems, the simulations systematically underestimate the fractional blockade levels.

Methods: Nanoparticle Synthesis and Characterization. All NANPs were assembled by combining individual monomer components at equimolar concentrations. The oligonucleotides encoding the composition of NANPs are listed below. DNA oligonucleotides were purchased from IDT (idtdna.com), and RNA strands were produced by in vitro run-off transcription using PCR-amplified DNA templates. For that, synthetic DNAs coding for the sequence of the designed RNA were amplified by PCR using primers containing the promoters for T7 RNA polymerase. PCR-amplified and purified (DNA Clean&Concentrator-5, Zymo Research) DNA templates (0.2 µM) were transcribed with "home-made" T7 RNA polymerase in 80 mM HEPES-KOH, pH 7.5; 2.5 mM spermidine; 50 mM DTT; 25 mM $MgCl_2$; 5 mM NTPs. Transcription was stopped with RQ1 DNase. Transcribed RNAs were purified with 8 M urea denaturing gel electrophoresis (PAGE, 15% acrylamide). The RNAs were eluted from gel slices overnight at 4° C. into 1×TBE buffer containing 300 mM NaCl and then precipitated in 2.5 volumes of 100% ethanol. Samples were then rinsed with 90% ethanol, vacuum dried, and dissolved in double-deionized water.

For assembly of DNA cubes, corresponding oligonucleotides (purchased from IDT) were mixed in doubly-deionized water, heated to 95° C. for 2 minutes, snap-cooled to 45° C. and incubated for 20 minutes. For assembly of RNA Rings, mixtures of RNAs (individually transcribed and purified) were heated to 95° C. for 2 minutes, followed by snap cooling on ice for 2 minutes, and incubation at 30° C. for 30 minutes. An assembly buffer (lx concentration: 89 mM tris-borate (pH 8.3), 2 mM $MgCl_2$, 50 mM KCl) was added following the heating step to all assemblies.

All NANPs were characterized by the electrophoretic mobility shift assays carried out on 8% non-denaturing native PAGE (37.5:1, 2 mM $MgCl_2$) and visualized with a Bio-Rad ChemiDoc MP System using total staining with ethidium bromide (EtBr). All gels were run for 30 mins at 4° C., 300 Volts. NANPs were further visualized by atomic force microscopy (AFM). For that, 5 μL of 50 nM NANPs were deposited on APS modified mica, incubated for ~2 min and air dried, as described previously. AFM visualization was carried out in tapping mode on a MultiMode AFM Nanoscope IV system (Bruker Instruments, Santa Barbara, Calif.). The images were recorded with a 1.5 Hz scanning rate using a TESPA-300 probe from Bruker with a resonance frequency of 320 kHz and spring constant of about 40 N/m. Images were processed by the FemtoScan Online software package (Advanced Technologies Center, Moscow, Russia)[73-74].

Nanopore Fabrication and Measurement. The nanopores devices are 5×5 $mm^2$ chips with a 50-nm-thick freestanding silicon nitride membranes at the center. Nanopores were drilled using a JEOL 2010F Transmission Electron Microscope operating at 200 kV. After fabrication, nanopore chips were cleaned using hot Piranha (sulfuric acid:hydrogen peroxide, 2:1), rinsed first by hot DI water and then by stream of DI water, and finally dried under a gentle stream of nitrogen. Next, the chips were mounted in a custom PTFE cell and a fast-curing silicone elastomer was used to seal the edges, as well as to paint the exposed areas of the chips as close as possible to the membrane. This painting along with a 2-μm thick silicon oxide layer intermediating the silicon substrate and the silicon nitride layer reduced the capacitive noise of these chips and allowed for high bandwidth electrical measurement of the ionic current through the nanopore. The RMS noise of the chips after filtering with a 1 MHz low-pass filter was in the range of 180-220 pA. The fluidic cell is composed of two chambers (cis and trans) that can only be connected through the nanopore. Experiments were performed with 400 mM KCl (10 mM Tris, 2 mM $MgCl_2$, pH 7.9). The small concentration of $Mg^{2+}$ ions was added to the buffer to help with preserving the nanoparticles. The silver/silver chloride electrodes interface the fluidics with the electronics. The ionic current was recorded using a Chimera VC100 amplifier (Chimera Instruments LLC), digitized at 4.17 Msample/s and digitally low-pass filtered.

Before each experiment the conductance of the nanopores were measured and compared against the theoretical values to confirm the dimensions of the nanopores. Next, the nanoparticle were added to the cis chamber (grounded) and a positive bias was applied to the trans chamber. Upon applying the bias the charged nanoparticles were electrophoretically driven through the nanopore and the translocation events were observed in the form of spikes in the DC current. The height and width of these events, i.e, current blockade by a nanoparticle and the dwell time of a nanoparticle in the nanopore contain information about the structure of the nanoparticles and their interactions with the nanopore. Additionally, the inter-event time distribution (the time interval between two successive events) was used to determine the capture rate which was then correlated with the concentration of nanoparticles. Pyth-lon, a nanopore data analysis package was used to extract such data from the recordings. Further analysis and distribution fittings were performed with MATLAB R2014.

Molecular Dynamics Simulations. All MD simulations of the NANPs/nanopore systems were carried out using NAMD2,[75] periodic boundary conditions, the CHARMM36 force field,[76] a custom force field for silica,[77] and the CUFIX corrections for ions.[78] Multiple timestepping[79] was used: local interactions were computed every 2 fs whereas long-range interactions were computed every 6 fs. All short-range nonbonded interactions were cut off starting at 0.8 nm and completely cut off by 1.0 nm. Long-range electrostatic interactions were evaluated using the particle-mesh Ewald method[80] computed over a 0.1 nm-spaced grid. SETTLE[81] and RATTLE[82] algorithms were applied to water and nucleic acid hydrogen atoms, respectively. A Langevin thermostat of 1.0 $ps^{-1}$ damping constant was coupled to silica atoms to maintain constant temperature. Atoms of silica membrane were also harmonically restrained to their initial coordinates; the spring constant of the restraints was 200 kcal $mol^{-1}$ $Å^{-2}$. Constant pressure simulations employed a Nose-Hoover Langevin piston.[83]

The atomic-scale model of a solid-state nanopore was obtained by annealing high-temperature (7000K) silica melt in the presence of a grid-based potential that defined the shape of the nanopore. During the annealing simulation, the temperature of the system was set to 7000 K, 5000 K, 2000 K, and 300 K for 40,000 steps, 40,000 steps, 100,000 steps, and 100,000 steps, respectively. These simulations were performed in vacuum using the BKS force field.[84] The nanopore shape was chosen to match the nanopore geometry realized in experiment[70]: the nanopore had an hourglass shape with the middle section approximated by a 9 nm diameter cylinder and the nanopore entrances approximated by 30 degree angle cones. To reduce the cost of MD simulations, the nanopore shape was cut in half along the midplane of the membrane, resulting in an asymmetric system shown in FIG. 4a. After annealing, atoms located farther than 1 nm away from the nanopore surface were removed, further reducing the computational cost of the simulations.

Initial models of NA particles were built by arranging DNA and RNA strands according to the particle's idealized geometry. The cube and the ring particles were submerged in a cubic volume of 400 mM KCl electrolyte 14 and 18 nm on each side, respectively. The systems were equilibrated in the constant number of particles, pressure and temperature (NPT) ensemble for over 60 ns each (P=1 atm; T=295 K). The equilibrated systems were then merged with the all-atom model of the nanopore, placing each NANP at the entrance of the nanopore with its center of mass initially located at the nanopore axis. The ring particle was initially oriented normal to the silica membrane. Three versions of the cube/nanopore system were built differing by the orientation of the cube with respect to the nanopore, SI Figure S6. Water and ions that clashed with the membrane were removed; additional volumes of 400 mM KCl solution were added to fully wet the nanopore and to form water-filled compartments on either side of the membrane. The final systems measured 16×16×23 $nm^3$ and contained approximately 470,000 atoms. The systems were equilibrated in the NPT ensemble for approximately 5 ns. Following the equilibration, the simulations were run in the constant number of particles, volume and temperature (NVT) ensemble. An external electric field $E=-V/L_Z$ was applied along the nanopore axis to produce the target drop of the electric potential, V, over the system's dimension in the direction of the applied field, $L_Z$.[85] In all simulations, a short-range repulsive potential was applied to atoms of NANPs to prevent their permanent binding to the nanopore surface.[86]

Compositions of nanoparticles used in this example:

```
RNA ring 5'→3'
(SEQ ID NO: 1) nrA:
GGGAACCGUCCACUGGUUCCCGCUACGAGAGCCUGCCUCGUAGC (SEQ ID NO: 2) nrB:
GGGAACCGCAGGCUGGUUCCCGCUACGAGAGAACGCCUCGUAGC (SEQ ID NO: 3) nrC:
GGGAACCGCGUUCUGGUUCCCGCUACGAGACGUCUCCUCGUAGC (SEQ ID NO: 4) nrD:
GGGAACCGAGACGUGGUUCCCGCUACGAGUCGUGGUCUCGUAGC (SEQ ID NO: 5) nrE:
GGGAACCACCACGAGGUUCCCGCUACGAGAACCAUCCUCGUAGC (SEQ ID NO: 6) nrF:
GGGAACCGAUGGUUGGUUCCCGCUACGAGAGUGGACCUCGUAGC DNA cube with three Ts at each corner 5'→3'
(SEQ ID NO: 7) dA:
GGCAACTTTGATCCCTCGGTTTAGCGCCGGCCTTTTCTCCCACA
CTTTCACG (SEQ ID NO: 8) dB:
GGGAAATTTCGTGGTAGGTTTTGTTGCCCGTGTTTCTACGATTA
CTTTGGTC (SEQ ID NO: 9) dC:
GGACATTTTCGAGACAGCATTTTTTCCCGACCTTTGCGGATTGT
ATTTTAGG (SEQ ID NO: 10) dD:
GGCGCTTTTGACCTTCTGCTTTATGTCCCCTATTTCTTAATGAC
TTTTGGCC (SEQ ID NO: 11) dE:
GGGAGATTTAGTCATTAAGTTTTACAATCCGCTTTGTAATCGTA
GTTTGTGT (SEQ ID NO: 12) dF:
GGGATCTTTACCTACCACGTTTTGCTGTCTCGTTTGCAGAAGGT
CTTTCCGA
```

Estimation of the Fractional Current Blockade

In working with the TEM-drilled nanopores usually an equivalent cylindrical pore with an effective pore length equal to one-third of the membrane thickness is used.[1] The fractional current blockade when a spherical analyte traverses a cylindrical pore can be calculated as $$i = 1 - \frac{R_0}{R_b} \quad (S1)$$

wherein $R_0$ is the open pore resistance, $$R_0 = \frac{1}{\sigma D} + 4L/\sigma \pi D^2,$$

and $R_b$ is the resistance of the pore partially blocked by the analyte:

$$R_b = \frac{1}{\sigma D} + \frac{1}{\sigma} \int_0^L \frac{dx}{A(x)} = \frac{1}{\sigma D} + 4\frac{L-d}{\sigma \pi D^2} + 4\frac{\operatorname{atan}\left(\frac{d}{\sqrt{D^2 - d^2}}\right)}{\sigma \pi \sqrt{D^2 - d^2}} \quad (S2)$$

L and D are the pore length and diameter, d is the analyte diameter, σ is the salt conductivity, and the equation is derived for the case of L >d. Moreover, the $$\frac{1}{\sigma D}$$

term accounts for the access resistance of the pore. This equation is plotted in FIG. 15 for a 9 nm-diameter nanopore with different lengths. It can be seen that when the analyte diameter to nanopore diameter ratio (d/D) is 0.5, only ~4% fractional blockade is obtained. This value reaches 20% when the size ratio increases to 0.8 (for L=20 nm). For the DNA cubes with a globular structure and the radius of gyration of ~4.4 nm (d=8.8 nm) obtained from the MD simulations (FIG. 15), equation S2 yields 43% blockade (D=9.5 nm, L=20 nm) which is consistent with the experimental results presented in FIG. 4, i.e., 35% blockade at 800 mV. Use of the radius of gyration for the RNA rings to estimate the fractional blockade is not justified, as the RNA rings have a planar structure. It's worthy of attention that although this calculation provides a rough estimate of the fractional blockade of the cubes in the nanopores, it cannot explain the monotonic increase of the fractional blockade with the applied bias. In fact this equation is based on the assumptions of a fixed shape for the analyte and uniform distribution of the electric field in the nanopore, which is not accurate for the TEM-drilled hourglass-shaped nanopores.

Example: Guidance Particles

Picomolar detection of DNA and RNA binding proteins. The ability to detect and quantify the presence of a variety of DNA and RNA binding proteins can provide the most direct information about the biological state of a cell and transform the study of gene regulation [73]. Current methods of measuring protein concentrations are indirect and hampered by a complicated setup process, lack of quantitative output, or a low sensitivity [73-76]. We have already demonstrated a nanopore method for the detection and differentiation of small amounts of nucleic acid nanoparticles (NANPs) [77]. In our method, an electric field is used to drive NANPs through a solid-state nanopore that is slightly smaller in size than the NANPs, which results in the NANPs being trapped in the nanopore for extended periods of time. The mismatch between the nanopore and NANP's dimensions makes it possible to carry out the measurement at high electric fields and thereby detect nanoparticles at picomolar concentration [77]. The same principle can be employed for picomolar detection of DNA and RNA binding proteins, FIG. 28. By engineering NANPs to contain targets for DNA or RNA binding proteins, one can directly count the number of nanoparticles having DNA or RNA protein bound to quantify their concentration in the sample solution.

Using a guiding particle to increase fidelity of nanopore sensing. A necessary condition for the success of this approach is the placement of the protein-NANP assembly within the nanopore in a reproducible conformation to guarantee that highly specific ionic current blockades are produced by protein-bound NANPs. Toward this goal, we have developed a method for guiding a protein-NANP complex toward a nanopore in a pre-determined conformation. To make the capture of a NANP-protein complex more reproducible a guidance particle 400 or a "parachute" particle is added to and bound to the NANPs to orient the protein-NANP complex in an external electric field E as it approaches the nanopore, see FIG. 28. In our MD simulations, we used a previously characterized atomic model of a DNA cube [77] because of its relatively small size and the abundance of potential protein binding sites. As a model parachute particle, we will use streptavidin covalently linked to the DNA cube via a nucleic acid linker 410. In order to test the parachute's effectiveness at stabilizing the NANP orientation, we simulated NANP-parachute complex in electric field that switched direction by 90 degrees. Upon changing the direction of the applied electric field, the NAMP-parachute complex was observed to orientate itself along the new field direction in less than 20 ns, proving the ability to use a guidance particle to reliably and repeatedly control the orientation of a NANP, thereby further increasing sensitivity. An example of use of a parachute particle or guiding particle to provide reliable alignment of the NANP under an applied electric field is illustrated in FIG. 29, where the NANP with parachute assembly aligns along the electric field direction on the order of nanoseconds. This demonstrates the relevance of using such guiding particles or parachute assemblies to ensure uniform NANP particle orientation with respect to the nanopore, thereby increasing system sensitivity by minimizing NANP electrical parameter variability during nanopore transit.

FIG. 28 further illustrates direct binding of analyte 420 to the NANP core structure, including by an analyte target sequence that is a part of the NANP core structure.

REFERENCES FOR EXAMPLE

[73] T. S. Furey. ChIP-seq and beyond: new and improved methodologies to detect and characterize protein-DNA interactions. Nature Reviews Genetics, 13:840-852, 2012.

[74] M. M. Garner and A. Revzin. A gel electrophoresis method for quantifying the binding of proteins to specific DNA regions: application to components of the *Escherichia coli* lactose operon regulatory system. Nucleic Acids Research, 9:3047-3060, 1981.

[75] D. J. Galas and A. Schmitz. DNAase footprinting: a simple method for the detection of protein-DNA binding specificity. Nucleic Acids Research, 5:3157-3170, 1978.

[76] P. Renard, I. Ernest, A. Houbion, M. Art, H. Le Calvez, M. Raes, and J. Remacle. Development of a sensitive multi-well colorimetric assay for active nfkb. Nucleic acids research, 29:E21, 2001.

[77] M. A. Alibakhshi, J. R. Halman, J. Wilson, A. Aksimentiev, K. A. Afonin, and M. Wanunu. Picomolar fingerprinting of nucleic acid nanoparticles using solid-state nanopores. ACS Nano, 11:9701-9710, 2017.

STATEMENTS REGARDING INCORPORATION BY REFERENCE AND VARIATIONS

All references throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention. The specific embodiments provided herein are examples of useful embodiments of the present invention and it will be apparent to one skilled in the art that the present invention may be carried out using a large number of variations of the devices, device components, methods and steps set forth in the present description. As will be obvious to one of skill in the art, methods and devices useful for the present embodiments can include a large number of optional device components, compositions, materials, combinations and processing elements and steps.

Every device, system, combination of components or method described or exemplified herein can be used to practice the invention, unless otherwise stated.

When a group of substituents is disclosed herein, it is understood that all individual members of that group and all subgroups, including any device components, combinations, materials and/or compositions of the group members, are disclosed separately. When a Markush group or other grouping is used herein, all individual members of the group and all combinations and subcombinations possible of the group are intended to be individually included in the disclosure.

Whenever a range is given in the specification, for example, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that compositions, materials, components, methods and/or processing steps other than those specifically exemplified can be employed in the practice of the invention without resort to undue experimentation. All art-known functional equivalents, of any such compositions, materials, components, methods and/or processing steps are intended to be included in this invention. The terms and expressions which have been employed are used as terms of description and not of limitation, and there is no intention in the use of such terms and expressions of excluding any equivalents of the features shown and described or portions thereof, but it is recognized that various modifications are within the scope of the invention claimed. Thus, it should be understood that although the present invention has been specifically disclosed by examplary embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a NANP" includes a plurality of NANPs and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

REFERENCES

1. Dekker, C., Solid-State Nanopores. Nat. Nanotechnol. 2007, 2, 209-215.
2. Bayley, H., Nanopore Sequencing: From Imagination to Reality. Clin. Chem. 2015, 61, 25-31.
3. Kasianowicz, J. J.; Robertson, J. W.; Chan, E. R.; Reiner, J. E.; Stanford, V. M., Nanoscopic Porous Sensors. Annu. Rev. Anal. Chem. 2008, 1, 737-766.
4. Howorka, S.; Siwy, Z., Nanopore Analytics: Sensing of Single Molecules. Chem. Soc. Rev. 2009, 38, 2360-2384.
5. Haque, F.; Li, J.; Wu, H.-C.; Liang, X.-J.; Guo, P., Solid-State and Biological Nanopore for Real-Time Sensing of Single Chemical and Sequencing of DNA. Nano today 2013, 8, 56-74.
6. Fennouri, A.; Przybylski, C. d.; Pastoriza-Gallego, M.; Bacri, L.; Auvray, L. c.; Daniel, R. g., Single Molecule Detection of Glycosaminoglycan Hyaluronic Acid Oligosaccharides and Depolymerization Enzyme Activity Using a Protein Nanopore. ACS nano 2012, 6, 9672-9678.
7. Bacri, L.; Oukhaled, A.; Hemon, E.; Bassafoula, F. B.; Auvray, L.; Daniel, R., Discrimination of Neutral Oligosaccharides through a Nanopore. Biochem. Biophys. Res. Commun. 2011, 412, 561-564.
8. Waduge, P.; Hu, R.; Bandrakar, P.; Yamazaki, H.; Cressiot, B.; Zhao, Q.; Whitford, P.; Wanunu, M., Nanopore-Based Measurements of Protein Size, Fluctuations, and Conformational Changes. ACS nano 2017, 11, 5706-5716.
9. Li, J.; Fologea, D.; Rollings, R.; Ledden, B., Characterization of Protein Unfolding with Solid-State Nanopores. Protein Pept. Lett. 2014, 21, 256-265.
10. Fologea, D.; Ledden, B.; McNabb, D. S.; Li, J., Electrical Characterization of Protein Molecules by a Solid-State Nanopore. Appl. Phys. Lett. 2007, 91, 053901.
11. Firnkes, M.; Pedone, D.; Knezevic, J.; Doblinger, M.; Rant, U., Electrically Facilitated Translocations of Proteins through Silicon Nitride Nanopores: Conjoint and Competitive Action of Diffusion, Electrophoresis, and Electroosmosis. Nano Lett. 2010, 10, 2162-2167.
12. Talaga, D. S.; Li, J., Single-Molecule Protein Unfolding in Solid State Nanopores. J. Am. Chem. Soc. 2009, 131, 9287-9297.
13. Wanunu, M.; Bhattacharya, S.; Xie, Y.; Tor, Y.; Aksimentiev, A.; Drndic, M., Nanopore Analysis of Individual Rna/Antibiotic Complexes. Acs Nano 2011, 5, 9345-9353.
14. Wanunu, M.; Sutin, J.; McNally, B.; Chow, A.; Meller, A., DNA Translocation Governed by Interactions with Solid-State Nanopores. Biophys. J. 2008, 95, 4716-4725.
15. Squires, A.; Gilboa, T.; Torfstein, C.; Varongchayakul, N.; Meller, A., Chapter Fourteen-Single-Molecule Characterization of DNA-Protein Interactions Using Nanopore Biosensors. Methods Enzymol. 2017, 582, 353-385.
16. Wang, S.; Haque, F.; Rychahou, P. G.; Evers, B. M.; Guo, P., Engineered Nanopore of Phi29 DNA-Packaging Motor for Real-Time Detection of Single Colon Cancer Specific Antibody in Serum. ACS nano 2013, 7, 9814-9822.
17. Reiner, J. E.; Balijepalli, A.; Robertson, J. W.; Campbell, J.; Suehle, J.; Kasianowicz, J. J., Disease Detection and Management Via Single Nanopore-Based Sensors. Chem. Rev. 2012, 112, 6431-6451.
18. Wanunu, M.; Dadosh, T.; Ray, V.; Jin, J.; McReynolds, L.; Drndic, M., Rapid Electronic Detection of Probe-Specific Micrornas Using Thin Nanopore Sensors. Nat. Nanotechnol. 2010, 5, 807-814.
19. Wang, Y.; Zheng, D.; Tan, Q.; Wang, M. X.; Gu, L.-Q., Nanopore-Based Detection of Circulating Micrornas in Lung Cancer Patients. Nat. Nanotechnol. 2011, 6, 668-674.
20. Branton, D.; Deamer, D. W.; Marziali, A.; Bayley, H.; Benner, S. A.; Butler, T.; Di Ventra, M.; Garaj, S.; Hibbs, A.; Huang, X., The Potential and Challenges of Nanopore Sequencing. Nat. Biotechnol. 2008, 26, 1146-1153.
21. Carson, S.; Wanunu, M., Challenges in DNA Motion Control and Sequence Readout Using Nanopore Devices. Nanotechnology 2015, 26, 074004.
22. Venkatesan, B. M.; Bashir, R., Nanopore Sensors for Nucleic Acid Analysis. Nat. Nanotechnol. 2011, 6, 615-624.
23. Wanunu, M., Nanopores: A Journey Towards DNA Sequencing. Phys. Life Rev. 2012, 9, 125-158.
24. Guo, P., The Emerging Field of Rna Nanotechnology. Nat Nanotechnol 2010, 5, 833-42.
25. Osada, E.; Suzuki, Y.; Hidaka, K.; Ohno, H.; Sugiyama, H.; Endo, M.; Saito, H., Engineering Rna-Protein Complexes with Different Shapes for Imaging and Therapeutic Applications. ACS nano 2014, 8, 8130-8140.
26. Ohno, H.; Kobayashi, T.; Kabata, R.; Endo, K.; Iwasa, T.; Yoshimura, S. H.; Takeyasu, K.; Inoue, T.; Saito, H., Synthetic Rna-Protein Complex Shaped Like an Equilateral Triangle. Nat. Nanotechnol. 2011, 6, 116-120.
27. Afonin, K. A.; Bindewald, E.; Yaghoubian, A. J.; Voss, N.; Jacovetty, E.; Shapiro, B. A.; Jaeger, L., In Vitro Assembly of Cubic Rna-Based Scaffolds Designed in Silico. Nat. Nanotechnol. 2010, 5, 676-682.
28. Afonin, K. A.; Cieply, D. J.; Leontis, N. B., Specific Rna Self-Assembly with Minimal Paranemic Motifs. J. Am. Chem. Soc. 2008, 130, 93-102.
29. Afonin, K. A.; Grabow, W. W.; Walker, F. M.; Bindewald, E.; Dobrovolskaia, M. A.; Shapiro, B. A.; Jaeger, L., Design and Self-Assembly of Sirna-Functionalized Rna Nanoparticles for Use in Automated Nanomedicine. Nat. Protoc. 2011, 6, 2022-2034.
30. Afonin, K. A.; Kasprzak, W.; Bindewald, E.; Puppala, P. S.; Diehl, A. R.; Hall, K. T.; Kim, T. J.; Zimmermann, M. T.; Jernigan, R. L.; Jaeger, L.; Shapiro, B. A., Computational and Experimental Characterization of Rna Cubic Nanoscaffolds. Methods 2014, 67, 256-265.
31. Afonin, K. A.; Kasprzak, W. K.; Bindewald, E.; Kireeva, M.; Viard, M.; Kashlev, M.; Shapiro, B. A., In Silico Design and Enzymatic Synthesis of Functional Rna Nanoparticles. Acc. Chem. Res. 2014, 47, 1731-1741.
32. Afonin, K. A.; Lindsay, B.; Shapiro, B. A., Engineered Rna Nanodesigns for Applications in Rna Nanotechnology. DNA RNA Nanotechnol. 2013, 1-15.
33. Bui, M. N.; Brittany Johnson, M.; Viard, M.; Satterwhite, E.; Martins, A. N.; Li, Z.; Marriott, I.; Afonin, K. A.; Khisamutdinov, E. F., Versatile Rna Tetra-U Helix Linking Motif as a Toolkit for Nucleic Acid Nanotechnology. Nanomedicine 2017.
34. Dibrov, S. M.; McLean, J.; Parsons, J.; Hermann, T., Self-Assembling Rna Square. Proc. Natl. Acad. Sci. U.S.A 2011, 108, 6405-8.
35. Guo, P.; Haque, F.; Hallahan, B.; Reif, R.; Li, H., Uniqueness, Advantages, Challenges, Solutions, and Perspectives in Therapeutics Applying Rna Nanotechnology. Nucleic Acid Ther. 2012, 22, 226-45.
36. Guo, P.; Zhang, C.; Chen, C.; Garver, K.; Trottier, M., Inter-Rna Interaction of Phage Phi29 Prna to Form a Hexameric Complex for Viral DNA Transportation. Mol. Cell 1998, 2, 149-55.
37. Guo, S.; Huang, F.; Guo, P., Construction of Folate-Conjugated Prna of Bacteriophage Phi29 DNA Packaging Motor for Delivery of Chimeric Sirna to Nasopharyngeal Carcinoma Cells. Gene Ther. 2006, 13, 814-20.
38. Bhatia, D.; Arumugam, S.; Nasilowski, M.; Joshi, H.; Wunder, C.; Chambon, V.; Prakash, V.; Grazon, C.; Nadal, B.; Maiti, P. K., Quantum Dot-Loaded Monofunctionalized DNA Icosahedra for Single-Particle Tracking of Endocytic Pathways. Nat. Nanotechnol. 2016, 11, 1112-1119.
39. Bhatia, D.; Mehtab, S.; Krishnan, R.; Indi, S. S.; Basu, A.; Krishnan, Y., Icosahedral DNA Nanocapsules by Modular Assembly. Angew. Chem. Int. Ed. 2009, 48, 4134-4137.
40. He, Y.; Ye, T.; Su, M.; Zhang, C.; Ribbe, A. E.; Jiang, W.; Mao, C., Hierarchical Self-Assembly of DNA into Symmetric Supramolecular Polyhedra. Nature 2008, 452, 198-201.
41. Andersen, E. S.; Dong, M.; Nielsen, M. M.; Jahn, K.; Subramani, R.; Mamdouh, W.; Golas, M. M.; Sander, B.; Stark, H.; Oliveira, C. L.; Pedersen, J. S.; Birkedal, V.; Besenbacher, F.; Gothelf, K. V.; Kjems, J., Self-Assembly of a Nanoscale DNA Box with a Controllable Lid. Nature 2009, 459, 73-6.
42. Bujold, K. E.; Hsu, J. C.; Sleiman, H. F., Optimized DNA "Nanosuitcases" for Encapsulation and Conditional Release of Sirna. J. Am. Chem. Soc. 2016, 138, 14030-14038.
43. Chidchob, P.; Edwardson, T. G.; Serpell, C. J.; Sleiman, H. F., Synergy of Two Assembly Languages in DNA Nanostructures: Self-Assembly of Sequence-Defined Polymers on DNA Cages. J. Am. Chem. Soc. 2016, 138, 4416-4425.
44. Liu, Z.; Tian, C.; Yu, J.; Li, Y.; Jiang, W.; Mao, C., Self-Assembly of Responsive Multilayered DNA Nanocages. J. Am. Chem. Soc. 2015, 137, 1730-1733.
45. Yu, J.; Liu, Z.; Jiang, W.; Wang, G.; Mao, C., De Novo Design of an Rna Tile That Self-Assembles into a Homo-Octameric Nanoprism. Nat. Commun. 2015, 6, 5724.
46. Goodman, R. P.; Schaap, I. A.; Tardin, C. F.; Erben, C. M.; Berry, R. M.; Schmidt, C. F.; Turberfield, A. J., Rapid Chiral Assembly of Rigid DNA Building Blocks for Molecular Nanofabrication. Science 2005, 310, 1661-1665.
47. Halman, J. R.; Satterwhite, E.; Roark, B.; Chandler, M.; Viard, M.; Ivanina, A.; Bindewald, E.; Kasprzak, W. K.; Panigaj, M.; Bui, M. N.; Lu, J. S.; Miller, J.; Khisamutdinov, E. F.; Shapiro, B. A.; Dobrovolskaia, M. A.; Afonin, K. A., Functionally-Interdependent Shape-Switching Nanoparticles with Controllable Properties. Nucleic Acids Res. 2017, 45, 2210-2220.
48. Afonin, K. A.; Viard, M.; Koyfman, A. Y.; Martins, A. N.; Kasprzak, W. K.; Panigaj, M.; Desai, R.; Santhanam, A.; Grabow, W. W.; Jaeger, L.; Heldman, E.; Reiser, J.; Chiu, W.; Freed, E. O.; Shapiro, B. A., Multifunctional Rna Nanoparticles. Nano Lett. 2014, 14, 5662-71.
49. Dao, B. N.; Viard, M.; Martins, A. N.; Kasprzak, W. K.; Shapiro, B. A.; Afonin, K. A., Triggering Rnai with Multifunctional Rna Nanoparticles and Their Delivery. DNA RNA Nanotechnol. 2015, 1, 27-38.
50. Guo, S.; Tschammer, N.; Mohammed, S.; Guo, P., Specific Delivery of Therapeutic Rnas to Cancer Cells Via the Dimerization Mechanism of Phi29 Motor Prna. Hum. Gene Ther. 2005, 16, 1097-1109.
51. Li, H.; Zhang, K. M.; Pi, F. M.; Guo, S. J.; Shlyakhtenko, L.; Chiu, W.; Shu, D.; Guo, P. X., Controllable Self-Assembly of Rna Tetrahedrons with Precise Shape and Size for Cancer Targeting. Adv. Mater. 2016, 28, 7501-7507.
52. Cassinelli, V.; Oberleitner, B.; Sobotta, J.; Nickels, P.; Grossi, G.; Kempter, S.; Frischmuth, T.; Liedl, T.; Manetto, A., One-Step Formation of "Chain-Armor"-Stabilized DNA Nanostructures. Angew. Chem. Int. Ed. 2015, 54, 7795-7798.
53. Kim, H.; Lee, J. S.; Lee, J. B., Generation of Sirna Nanosheets for Efficient Rna Interference. Sci. Rep. 2016, 6.
54. Stewart, J. M.; Viard, M.; Subramanian, H. K. K.; Roark, B. K.; Afonin, K. A.; Franco, E., Programmable Rna Microstructures for Coordinated Delivery of Sirnas. Nanoscale 2016, 8, 17542-17550.
55. Saleh, O. A.; Sohn, L. L., Direct Detection of Antibody-Antigen Binding Using an on-Chip Artificial Pore. Proc. Natl. Acad. Sci. U.S.A. 2003, 100, 820-824.
56. Wu, H.; Liu, H.; Tan, S.; Yu, J.; Zhao, W.; Wang, L.; Liu, Q., The Estimation of Field-Dependent Conductance Change of Nanopore by Field-Induced Charge in the Translocations of Aunps-DNA Conjugates. J. Phys. Chem. C 2014, 118, 26825-26835.
57. Cai, H.; Wang, Y.; Yu, Y.; Mirkin, M. V.; Bhakta, S.; Bishop, G. W.; Joshi, A. A.; Rusling, J. F., Resistive-Pulse Measurements with Nanopipettes: Detection of Vascular Endothelial Growth Factor C (Vegf-C) Using Antibody-Decorated Nanoparticles. Anal. Chem. 2015, 87, 6403-6410.
58. Wang, Y.; Kececi, K.; Mirkin, M. V.; Mani, V.; Sardesai, N.; Rusling, J. F., Resistive-Pulse Measurements with Nanopipettes: Detection of Au Nanoparticles and Nanoparticle-Bound Anti-Peanut Igy. Chem. Sci. 2013, 4, 655-663.
59. Pevarnik, M.; Schiel, M.; Yoshimatsu, K.; Vlassiouk, I. V.; Kwon, J. S.; Shea, K. J.; Siwy, Z. S., Particle Deformation and Concentration Polarization in Electroosmotic Transport of Hydrogels through Pores. ACS nano 2013, 7, 3720-3728.
60. Holden, D. A.; Hendrickson, G. R.; Lan, W.-J.; Lyon, L. A.; White, H. S., Electrical Signature of the Deformation and Dehydration of Microgels During Translocation through Nanopores. Soft Matter 2011, 7, 803 5-8040.
61. Holden, D. A.; Hendrickson, G.; Lyon, L. A.; White, H. S., Resistive Pulse Analysis of Microgel Deformation During Nanopore Translocation. J. Phys. Chem. C 2011, 115, 2999-3004.
62. Yingling, Y. G.; Shapiro, B. A., Computational Design of an Rna Hexagonal Nanoring and an Rna Nanotube. Nano Lett. 2007, 7, 2328-2334.
63. Grabow, W. W.; Zakrevsky, P.; Afonin, K. A.; Chworos, A.; Shapiro, B. A.; Jaeger, L., Self-Assembling Rna Nanorings Based on Rnai/Ii Inverse Kissing Complexes. Nano Lett. 2011, 11, 878-887.
64. Li, J.; Talaga, D. S., The Distribution of DNA Translocation Times in Solid-State Nanopores. J. Phys.: Condens. Matter 2010, 22, 454129.
65. Larkin, J.; Henley, R. Y.; Muthukumar, M.; Rosenstein, J. K.; Wanunu, M., High-Bandwidth Protein Analysis Using Solid-State Nanopores. Biophys. J. 2014, 106, 696-704.
66. Rosenstein, J. K.; Wanunu, M.; Merchant, C. A.; Drndic, M.; Shepard, K. L., Integrated Nanopore Sensing Platform with Sub-Microsecond Temporal Resolution. Nat. Methods 2012, 9, 487-492.
67. Heng, J. B.; Aksimentiev, A.; Ho, C.; Marks, P.; Grinkova, Y. V.; Sligar, S.; Schulten, K.; Timp, G., Stretching DNA Using the Electric Field in a Synthetic Nanopore. Nano Lett. 2005, 5, 1883-1888.
68. Plesa, C.; Ananth, A. N.; Linko, V.; Gilcher, C.; Katan, A. J.; Dietz, H.; Dekker, C., Ionic Permeability and Mechanical Properties of DNA Origami Nanoplates on Solid-State Nanopores. ACS nano 2013, 8, 35-43.
69. Kim, M. J.; McNally, B.; Murata, K.; Meller, A., Characteristics of Solid-State Nanometre Pores Fabricated Using a Transmission Electron Microscope. Nanotechnology 2007, 18, 205302.
70. Kim, M. J.; Wanunu, M.; Bell, D. C.; Meller, A., Rapid Fabrication of Uniformly Sized Nanopores and Nanopore Arrays for Parallel DNA Analysis. Adv. Mater. 2006, 18, 3149-3153.
71. Gershow, M.; Golovchenko, J. A., Recapturing and Trapping Single Molecules with a Solid-State Nanopore. Nat. Nanotechnol. 2007, 2, 775-779.
72. Wanunu, M.; Morrison, W.; Rabin, Y.; Grosberg, A. Y.; Meller, A., Electrostatic Focusing of Unlabelled DNA into Nanoscale Pores Using a Salt Gradient. Nat. Nanotechnol. 2010, 5, 160-165.
73. Shlyakhtenko, L. S.; Gall, A. A.; Lyubchenko, Y. L., Mica Functionalization for Imaging of DNA and Protein-DNA Complexes with Atomic Force Microscopy. Methods Mol. Biol. 2013, 931, 295-312.
74. Shlyakhtenko, L. S.; Gall, A. A.; Filonov, A.; Cerovac, Z.; Lushnikov, A.; Lyubchenko, Y. L., Silatrane-Based Surface Chemistry for Immobilization of DNA, Protein-DNA Complexes and Other Biological Materials. Ultramicroscopy 2003, 97, 279-87.
75. Phillips, J. C.; Braun, R.; Wang, W.; Gumbart, J.; Tajkhorshid, E.; Villa, E.; Chipot, C.; Skeel, R. D.; Kale, L.; Schulten, K., Scalable Molecular Dynamics with Namd. J. Comput. Chem. 2005, 26, 1781-1802.
76. Best, R. B.; Zhu, X.; Shim, J.; Lopes, P. E.; Mittal, J.; Feig, M.; MacKerell Jr, A. D., Optimization of the Additive Charmm All-Atom Protein Force Field Targeting Improved Sampling of the Backbone $\phi$, $\Psi$ and Side-Chain X1 and X2 Dihedral Angles. J. Chem. Theory Comput. 2012, 8, 3257-3273.
77. Cruz-Chu, E. R.; Aksimentiev, A.; Schulten, K., Water-Silica Force Field for Simulating Nanodevices. J. Phys. Chem. B 2006, 110, 21497-21508.
78. Yoo, J.; Aksimentiev, A., Competitive Binding of Cations to Duplex DNA Revealed through Molecular Dynamics Simulations. J. Phys. Chem. B 2012, 116, 12946-12954.
79. Batcho, P. F.; Case, D. A.; Schlick, T., Optimized Particle-Mesh Ewald/Multiple-Time Step Integration for Molecular Dynamics Simulations. J. Chem. Phys. 2001, 115, 4003-4018.
80. Darden, T.; York, D.; Pedersen, L., Particle Mesh Ewald: An N. Log (N) Method for Ewald Sums in Large Systems. J. Chem. Phys. 1993, 98, 10089-10092.
81. Miyamoto, S.; Kollman, P. A., Settle: An Analytical Version of the Shake and Rattle Algorithm for Rigid Water Models. J. Comput. Chem. 1992, 13, 952-962.
82. Andersen, H. C., Rattle: A "Velocity" Version of the Shake Algorithm for Molecular Dynamics Calculations. J. Comput. Phys. 1983, 52, 24-34.
83. Martyna, G. J.; Tobias, D. J.; Klein, M. L., Constant Pressure Molecular Dynamics Algorithms. J. Chem. Phys. 1994, 101, 4177-4189.
84. Van Beest, B.; Kramer, G. J.; Van Santen, R., Force Fields for Silicas and Aluminophosphates Based on Ab Initio Calculations. Phys. Rev. Lett. 1990, 64, 1955.
85. Aksimentiev, A.; Heng, J. B.; Timp, G.; Schulten, K., Microscopic Kinetics of DNA Translocation through Synthetic Nanopores. Biophys. J. 2004, 87, 2086-2097.
86. Comer, J.; Dimitrov, V.; Zhao, Q.; Timp, G.; Aksimentiev, A., Microscopic Mechanics of Hairpin DNA Translocation through Synthetic Nanopores. Biophys. J. 2009, 96, 593-608.

TABLE 1

Summary of in silico experiments. Two NANPs were simulated: the DNA cube and the RNA ring, as well as an empty pore. The cubes were simulated starting from three orientations differing by the part of the cube that was closest to the nanopore constriction (FIG. 15). The blockade current was measured after the particles reached a stable position within the nanopore; the time elapsed from the beginning of the simulation before each particle reached such stable position is specified in the table as ts.

| NA Particle | Voltage | Simulation time | Orientation | $t_S$ (ns) | Current (nA) |
|---|---|---|---|---|---|
| Cube | 200 mV | 98 ns | Flat | 20 ns | 5.32 ± 0.08 |
| Cube | 200 mV | 97 ns | Corner | 20 ns | 5.71 ± 0.06 |
| Cube | 200 mV | 99 ns | Edge | 35 ns | 5.85 ± 0.07 |
| Cube | 500 mV | 70 ns | Flat | 25 ns | 13.53 ± 0.11 |
| Cube | 500 mV | 70 ns | Edge | 25 ns | 14.94 ± 0.09 |
| Cube | 500 mV | 70 ns | Corner | N/A | N/A |
| Ring | 200 mV | 116 ns | Vertical | 60 ns | 7.04 ± 0.07 |
| Ring | 200 mV | 88 ns | Vertical | 20 ns | 6.34 ± 0.08 |
| Ring | 500 mV | 109 ns | Vertical | 25 ns | 16.43 ± 0.08 |
| Ring | 500 mV | 84 ns | Vertical | 12 ns | 16.61 ± 0.09 |
| Empty | 200 mV | 57 ns | N/A | 20 ns | 7.14 ± 0.10 |
| Empty | 500 mV | 48 ns | N/A | 10 ns | 17.33 ± 0.11 |

The invention claimed is:

1. A plurality of analyte-linkable nucleic acid nanoparticle (NANP) populations for detecting one or more analytes in a sample, each member of an NANP population comprising:
   a plurality of nucleic acid sequences that forms a core NANP structure;
   a first analyte target sequence configured to specifically bind to a first analyte;
   a second analyte target sequence configured to specifically bind to a second analyte;
   a population-unique NANP electronic signature;
   wherein the first analyte binds to a first population of NANPs at a first analyte binding site and to a second population of NANPs at a second analyte binding site to form a linear chain of NANPs with a sequence dependent on the analytes in the sample;
   wherein each core NANP structure has a preselected shape, size, charge and/or composition configured to provide an ionic current blockade, impedance, resistance or time course thereof that is different from a next closest NANP ionic current blockade, impedance, resistance or time course thereof as the linear chain of NANPs transit a solid-state nanopore under an applied electric field.

2. The NANPs of claim 1, wherein the analyte target sequence extends from the core NANP structure.

3. The NANPs of claim 1, wherein the analyte target sequence is a part of the core NANP structure.

4. The NANPs of claim 1, wherein each NANP comprises a plurality of analyte target sequences.

5. The NANPs of claim 4, wherein the plurality of analyte target sequences are each unique to thereby target a plurality of unique analytes.

6. The NANPs of claim 1, wherein the core NANP structure has a controllable shape, density, and/or effective size, to provide the unique NANP electronic signature.

7. The NANPs of claim 1, having a biomarker-linked linear chain formed of a plurality of NANP populations of the sequence comprising:
$NANP_1$-BiomarkerA-$NANP_2$-BiomarkerB-$NANP_3$.

8. The NANPs of claim 1, wherein at least one NANP population comprises a mixture of RNA and DNA.

9. The NANPs of claim 1, wherein the NANPs have an effective diameter that is matched to a diameter of the solid state nanopore so that the NANP deforms under an applied electric field to transit the solid-state nanopore.

10. The NANPs of claim 1, wherein:
the first and second analyte target sequences each have a length selected from the range of 4 to 100 nucleotides;
the first and second analyte target sequences each have a complementary sequence of at least 80%, to a binding region of the analyte, for an analyte that is a nucleotide sequence;
the first and second analyte target sequences are each an aptamer that bind to an analyte that is a polypeptide or a portion of a protein sequence;
the first and second analyte target sequences are each selected to specifically bind to an analyte that is a biomarker indicative of a disease state or infection;
the first analyte target sequence comprises a plurality of unique biomarker target sequences spatially distributed over the NANP surface for multiplexed combinatorial analysis of a plurality of biomarkers; and/or
the first and second analyte target sequences each comprise a protector strand to inhibit unwanted secondary structure in the analyte target sequence.

11. The NANPs of claim 10, wherein each of the unique biomarker target sequences have a complementary sequence of at least 90% to a target sequence of said biomarker.

12. The NANPs of claim 1 provided as a kit for detection of a health condition.

13. The NANPs of claim 1, further comprising a guidance particle connected to the NANP core structure to provide controlled alignment of the NANP during movement toward a nanopore.

14. A system for multiplex detection of biomarkers from a biological sample comprising:
the plurality of biomarker-linkable nucleic acid nanoparticles (NANP) populations of claim 1;
a membrane comprising:
a first surface and a second surface opposite said first surface, wherein said membrane separates a first fluid compartment comprising said first surface from a second fluid compartment comprising said second surface;
a nanopore through said membrane that fluidically connects said first fluid compartment and said second fluid compartment;
a power supply in electrical contact with said membrane to provide an electric potential difference between said first fluid compartment and said second fluid compartment; and
a detector to detect a time-varying electrical current through said nanopore as a linear chain of NANPs with a biomarker that links adjacent NANPs in the linear chain of NANPs transits said nanopore under an applied electric potential difference.

15. The system of claim 14, wherein the nanopore has an average nanopore diameter of between 5 nm to 100 nm.

16. The NANP of claim 1, wherein said population-unique NANP electronic signature is an ionic current blockade that is at least 1% different from a next closest NANP ionic current blockade.

17. A method of detecting a plurality of biomarkers in a sample, the method comprising the steps of:
mixing a sample with a plurality of unique NANPs of claim 1;
incubating the sample-NANPs mixture for an incubation time to form a chain of biomarker-linked NANPs;
introducing the linear chain of biomarker-linked NANPs to a first chamber formed by a first side of a nanopore-containing membrane, wherein the nanopore-fluidically connects the first chamber to a second chamber formed by a second side of the nanopore-containing membrane;
electrically energizing the nanopore-containing membrane to drive the chain of biomarker-linked NANPs through the nanopore from the first chamber to the second chamber; and
measuring an ionic current blockade as a function of time as the chain of biomarker-linked NANPs transit the nanopore, wherein the ionic current blockade signature identifies the NANP sequence of the chain of biomarker-linked NANPs, thereby detecting the plurality of biomarkers in the sample.

18. The method of claim 17, wherein the measuring the ionic current blockade comprises measuring the magnitude and/or duration of the current blockade.

19. The method of claim 17, wherein the NANPs are made by the steps of:
providing a fixed number of DNA and/or RNA strands; and
assembling the DNA and/or RNA strands in a prescribed shape so that each unique nanoparticle produces an ionic current blockade when passed through a nanopore that is different from every other unique NANP.

20. The method of claim 17, wherein each NANP has a plurality of unique analyte target sequences for targeting a plurality of different analytes so that a single set of NANP populations can detect a variety of health conditions.

21. The method of claim 20, wherein the analytes comprise one or more of:
a cancer marker;
an autoimmune marker;
a cardiac marker;
an infectious marker;
a genetic marker;
a metabolite,
a protein; and
nucleic acids.

22. The method of claim 21, wherein between two and ten NANP populations are used to detect between one and fifty unique analytes.

23. An analyte-linkable nucleic acid nanoparticle (NANP) comprising:
   a plurality of nucleic acid sequences that forms a core NANP structure having an NANP electronic signature during transit through a nanopore;
   an analyte target sequence configured to specifically bind to an analyte;
   a guidance particle connected to the core NANP structure to provide a reproducible orientation as the NANP approaches the nanopore under an applied electric field.

24. The NANP of claim 23, wherein the guidance particle is connected to the core NANP structure by a linker.

25. The NANP of claim 23, wherein the analyte target sequence specifically binds to a nucleic acid binding protein.

26. The NANP of claim 25, wherein the nucleic acid binding protein is a transcription factor.

27. The NANP of claim 23, wherein the guidance particle comprises a biomolecule, including a streptavidin protein, connected to the core NANP structure through a peptide nucleic acid linker.

28. The NANP of claim 23, wherein the guidance particle comprises a plurality of particles connected to the core NANP structure.

* * * * *

SEQUENCE LISTING

<160> NUMBER OF SEQ ID NOS: 12

<210> SEQ ID NO 1
<211> LENGTH: 44
<212> TYPE: RNA
<213> ORGANISM: Artificial Sequence
<220> FEATURE:
<223> OTHER INFORMATION: synthetic construct

<400> SEQUENCE: 1
gggaaccguc cacugguucc cgcuacgaga gccugccucg uagc         44

<210> SEQ ID NO 2
<211> LENGTH: 44
<212> TYPE: RNA
<213> ORGANISM: Artificial Sequence
<220> FEATURE:
<223> OTHER INFORMATION: synthetic construct

<400> SEQUENCE: 2
gggaaccgca ggcugguucc cgcuacgaga gaacgccucg uagc         44

<210> SEQ ID NO 3
<211> LENGTH: 44
<212> TYPE: RNA
<213> ORGANISM: Artificial Sequence
<220> FEATURE:
<223> OTHER INFORMATION: synthetic construct

<400> SEQUENCE: 3
gggaaccgcg uucugguucc cgcuacgaga cgucccucg uagc          44

<210> SEQ ID NO 4
<211> LENGTH: 44
<212> TYPE: RNA
<213> ORGANISM: Artificial Sequence
<220> FEATURE:
<223> OTHER INFORMATION: synthetic construct

<400> SEQUENCE: 4
gggaaccgag acgugguucc cgcuacgagu cguggucucg uagc         44

<210> SEQ ID NO 5
<211> LENGTH: 44
<212> TYPE: RNA
<213> ORGANISM: Artificial Sequence
<220> FEATURE:
<223> OTHER INFORMATION: synthetic construct

<400> SEQUENCE: 5
gggaaccacc acgagguucc cgcuacgaga accauccucg uagc         44

<210> SEQ ID NO 6
<211> LENGTH: 44
<212> TYPE: RNA
<213> ORGANISM: Artificial Sequence
<220> FEATURE:
<223> OTHER INFORMATION: synthetic construct

<400> SEQUENCE: 6
gggaaccgau ggugguucc cgcuacgaga guggaccucg uagc          44

<210> SEQ ID NO 7
<211> LENGTH: 52
<212> TYPE: DNA
<213> ORGANISM: Artificial Sequence

```
<220> FEATURE:
<223> OTHER INFORMATION: synthetic construct

<400> SEQUENCE: 7
ggcaactttg atccctcggt ttagcgccgg cctttctcc cacactttca cg            52

<210> SEQ ID NO 8
<211> LENGTH: 52
<212> TYPE: DNA
<213> ORGANISM: Artificial Sequence
<220> FEATURE:
<223> OTHER INFORMATION: synthetic construct

<400> SEQUENCE: 8
gggaaatttc gtggtaggtt ttgttgcccg tgtttctacg attactttgg tc            52

<210> SEQ ID NO 9
<211> LENGTH: 52
<212> TYPE: DNA
<213> ORGANISM: Artificial Sequence
<220> FEATURE:
<223> OTHER INFORMATION: synthetic construct

<400> SEQUENCE: 9
ggacattttc gagacagcat tttttcccga cctttgcgga ttgtatttta gg            52

<210> SEQ ID NO 10
<211> LENGTH: 52
<212> TYPE: DNA
<213> ORGANISM: Artificial Sequence
<220> FEATURE:
<223> OTHER INFORMATION: synthetic construct

<400> SEQUENCE: 10
ggcgcttttg accttctgct ttatgtcccc tatttcttaa tgactttggg cc            52

<210> SEQ ID NO 11
<211> LENGTH: 52
<212> TYPE: DNA
<213> ORGANISM: Artificial Sequence
<220> FEATURE:
<223> OTHER INFORMATION: synthetic construct

<400> SEQUENCE: 11
gggagattta gtcattaagt tttacaatcc gctttgtaat cgtagtttgt gt            52

<210> SEQ ID NO 12
<211> LENGTH: 52
<212> TYPE: DNA
<213> ORGANISM: Artificial Sequence
<220> FEATURE:
<223> OTHER INFORMATION: synthetic construct

<400> SEQUENCE: 12
gggatcttta cctaccacgt tttgctgtct cgtttgcaga aggtctttcc ga            52
```